(12) United States Patent
Wardle et al.

(10) Patent No.: US 12,076,273 B2
(45) Date of Patent: Sep. 3, 2024

(54) DELIVERING OCULAR IMPLANTS INTO THE EYE

(71) Applicant: Alcon Inc., Fribourg (CH)

(72) Inventors: John Wardle, San Clemente, CA (US); Andrew T. Schieber, Tustin, CA (US)

(73) Assignee: Alcon Inc., Fribourg (CH)

( * ) Notice: Subject to any disclaimer, the term of this patent is extended or adjusted under 35 U.S.C. 154(b) by 439 days.

(21) Appl. No.: 17/389,968

(22) Filed: Jul. 30, 2021

(65) Prior Publication Data

US 2021/0361479 A1 Nov. 25, 2021

Related U.S. Application Data

(63) Continuation of application No. 14/363,409, filed as application No. PCT/US2012/070626 on Dec. 19, (Continued)

(51) Int. Cl.
| | |
|---|---|
| *A61F 9/007* | (2006.01) |
| *A61B 17/34* | (2006.01) |
| *A61F 9/00* | (2006.01) |

(52) U.S. Cl.
CPC ........ *A61F 9/0026* (2013.01); *A61B 17/3421* (2013.01); *A61F 9/0017* (2013.01); (Continued)

(58) Field of Classification Search
CPC .... A61F 9/00781; A61F 9/0017; A61F 9/007; A61F 9/0026; A61F 2/95; (Continued)

(56) References Cited

U.S. PATENT DOCUMENTS

| | | |
|---|---|---|
| 703,296 A | 6/1902 | Arnold |
| 1,601,709 A | 10/1926 | Windom |
| (Continued) | | |

FOREIGN PATENT DOCUMENTS

| | | |
|---|---|---|
| AU | 1998/76197 B2 | 2/1999 |
| DE | 4226476 C1 | 8/1993 |
| (Continued) | | |

OTHER PUBLICATIONS

Noda et al.; U.S. Appl. No. 17/572,064 entitled "Systems and methods for viscoelastic delivery," filed Jan. 10, 2022.
(Continued)

*Primary Examiner* — Ariana Zimbouski

(57) ABSTRACT

A method of deploying an ocular implant into Schlemm's canal of an eye. The method includes the steps of inserting a distal end of a cannula through a cornea of the eye and into an anterior chamber of the eye, the cannula having a distal opening extending from the distal end and through a side wall; placing the distal opening of the cannula into fluid communication with Schlemm's canal; advancing the ocular implant distally through the cannula with a delivery tool engaged with the ocular implant, a proximal portion of the ocular implant engaging the delivery tool proximal to a distal portion of the delivery tool; and disengaging the ocular implant and the delivery tool when the proximal portion of the ocular implant reaches the cannula distal opening. The invention also includes a system for practicing the method.

3 Claims, 45 Drawing Sheets

Related U.S. Application Data 2012, now Pat. No. 11,135,088, which is a continuation of application No. 13/330,592, filed on Dec. 19, 2011, now Pat. No. 8,663,150.

(52) U.S. Cl.
CPC .. *A61F 9/00781* (2013.01); *A61B 2017/3454* (2013.01); *A61B 17/3468* (2013.01); *A61F 2220/0033* (2013.01)

(58) Field of Classification Search
CPC ....... A61F 2009/00891; A61M 27/002; A61M 2210/0612; A61B 17/3468
See application file for complete search history.

(56) References Cited

U.S. PATENT DOCUMENTS

| | | |
|---|---|---|
| 2,716,983 A | 9/1955 | George et al. |
| 3,071,135 A | 1/1963 | Baldwin et al. |
| 3,788,327 A | 1/1974 | Donowitz et al. |
| 3,811,442 A | 5/1974 | Maroth |
| 3,858,577 A | 1/1975 | Bass et al. |
| 3,884,236 A | 5/1975 | Krasnov |
| 3,948,271 A | 4/1976 | Akiyama |
| 3,982,541 A | 9/1976 | L'Esperance |
| 4,037,604 A | 7/1977 | Newkirk |
| 4,134,405 A | 1/1979 | Smit |
| 4,273,109 A | 6/1981 | Enderby |
| 4,391,275 A | 7/1983 | Fankhauser et al. |
| 4,428,746 A | 1/1984 | Mendez |
| 4,457,757 A | 7/1984 | Molteno |
| 4,461,294 A | 7/1984 | Baron |
| 4,470,407 A | 9/1984 | Hussein |
| 4,497,319 A | 2/1985 | Sekine et al. |
| 4,501,274 A | 2/1985 | Skjaerpe |
| 4,517,973 A | 5/1985 | Sunago et al. |
| 4,538,608 A | 9/1985 | L'Esperance |
| 4,548,205 A | 10/1985 | Armeniades et al. |
| 4,551,129 A | 11/1985 | Coleman et al. |
| 4,558,698 A | 12/1985 | O'Dell |
| 4,559,942 A | 12/1985 | Eisenberg |
| 4,566,438 A | 1/1986 | Liese et al. |
| 4,580,559 A | 4/1986 | L'Esperance |
| 4,583,539 A | 4/1986 | Karlin et al. |
| 4,601,713 A | 7/1986 | Fuquo |
| 4,604,087 A | 8/1986 | Joseph |
| 4,633,866 A | 1/1987 | Peyman et al. |
| 4,658,816 A | 4/1987 | Ector |
| 4,660,546 A | 4/1987 | Herrick et al. |
| 4,671,273 A | 6/1987 | Lindsey |
| 4,689,040 A | 8/1987 | Thompson |
| 4,699,140 A | 10/1987 | Holmes et al. |
| 4,706,669 A | 11/1987 | Schlegel |
| 4,722,350 A | 2/1988 | Armeniades et al. |
| 4,722,724 A | 2/1988 | Schocket |
| 4,729,373 A | 3/1988 | Peyman |
| 4,733,665 A | 3/1988 | Palmaz |
| 4,750,901 A | 6/1988 | Molteno |
| 4,770,654 A | 9/1988 | Rogers et al. |
| 4,791,927 A | 12/1988 | Menger |
| 4,826,478 A | 5/1989 | Schocket |
| 4,846,172 A | 7/1989 | Berlin |
| 4,861,341 A | 8/1989 | Woodburn |
| 4,876,250 A | 10/1989 | Clark |
| 4,880,000 A | 11/1989 | Holmes et al. |
| 4,886,488 A | 12/1989 | White |
| 4,919,130 A | 4/1990 | Stoy et al. |
| 4,925,299 A | 5/1990 | Meisberger et al. |
| 4,934,363 A | 6/1990 | Smith et al. |
| 4,934,809 A | 6/1990 | Volk |
| 4,936,825 A | 6/1990 | Ungerleider |
| 4,946,436 A | 8/1990 | Smith |
| 4,968,296 A | 11/1990 | Ritch et al. |
| 4,994,060 A | 2/1991 | Rink et al. |
| 5,034,010 A | 7/1991 | Kittrell et al. |
| 5,092,837 A | 3/1992 | Ritch et al. |
| 5,123,902 A | 6/1992 | Muller et al. |
| 5,127,901 A | 7/1992 | Odrich |
| 5,129,895 A | 7/1992 | Vassiliadis et al. |
| 5,178,604 A | 1/1993 | Baerveldt et al. |
| 5,180,362 A | 1/1993 | Worst |
| 5,190,552 A | 3/1993 | Kelman |
| 5,213,569 A | 5/1993 | Davis |
| 5,246,452 A | 9/1993 | Sinnott |
| 5,254,112 A | 10/1993 | Sinofsky et al. |
| 5,273,056 A | 12/1993 | McLaughlin et al. |
| 5,290,267 A | 3/1994 | Zimmermann |
| 5,300,020 A | 4/1994 | L'Esperance |
| 5,359,685 A | 10/1994 | Waynant et al. |
| 5,360,399 A | 11/1994 | Stegmann |
| 5,371,078 A | 12/1994 | Clark et al. |
| 5,372,577 A | 12/1994 | Ungerleider |
| 5,445,637 A | 8/1995 | Bretton |
| 5,454,796 A | 10/1995 | Krupin |
| 5,458,615 A | 10/1995 | Klemm et al. |
| 5,501,274 A | 3/1996 | Nguyen et al. |
| 5,536,259 A | 7/1996 | Utterberg |
| 5,575,780 A | 11/1996 | Saito |
| 5,591,223 A | 1/1997 | Lock et al. |
| 5,607,966 A | 3/1997 | Hellberg et al. |
| 5,613,972 A | 3/1997 | Lee et al. |
| 5,626,558 A | 5/1997 | Suson |
| 5,643,250 A | 7/1997 | O'Donnell |
| 5,653,753 A | 8/1997 | Brady et al. |
| 5,657,760 A | 8/1997 | Ying et al. |
| 5,676,669 A | 10/1997 | Colvard |
| 5,704,907 A | 1/1998 | Nordquist et al. |
| 5,713,844 A | 2/1998 | Peyman |
| 5,722,970 A | 3/1998 | Colvard et al. |
| 5,738,676 A | 4/1998 | Hammer et al. |
| 5,738,677 A | 4/1998 | Colvard et al. |
| 5,785,658 A | 7/1998 | Benaron et al. |
| 5,792,099 A | 8/1998 | DeCamp et al. |
| 5,792,103 A | 8/1998 | Schwartz et al. |
| 5,807,302 A | 9/1998 | Wandel |
| 5,811,453 A | 9/1998 | Yanni et al. |
| 5,865,831 A | 2/1999 | Cozean et al. |
| 5,868,697 A | 2/1999 | Richter et al. |
| 5,879,319 A | 3/1999 | Pynson et al. |
| 5,885,279 A | 3/1999 | Bretton |
| 5,893,837 A | 4/1999 | Eagles et al. |
| 5,895,831 A | 4/1999 | Brasier et al. |
| 5,919,171 A | 7/1999 | Kira et al. |
| 5,948,427 A | 9/1999 | Yamamoto et al. |
| 5,968,058 A | 10/1999 | Richter et al. |
| 5,984,963 A | 11/1999 | Ryan et al. |
| 5,990,099 A | 11/1999 | Clark |
| 5,993,438 A | 11/1999 | Juhasz et al. |
| 5,997,531 A | 12/1999 | Loeb et al. |
| 6,002,480 A | 12/1999 | Izatt et al. |
| 6,007,511 A | 12/1999 | Prywes |
| 6,050,970 A | 4/2000 | Baerveldt |
| 6,083,193 A | 7/2000 | Kadziauskas et al. |
| 6,099,521 A | 8/2000 | Shadduck |
| 6,102,045 A | 8/2000 | Nordquist et al. |
| 6,142,990 A | 11/2000 | Burk |
| 6,146,375 A | 11/2000 | Juhasz et al. |
| 6,177,544 B1 | 1/2001 | Kanal et al. |
| 6,186,974 B1 | 2/2001 | Allan et al. |
| 6,217,584 B1 | 4/2001 | Nun |
| 6,221,078 B1 | 4/2001 | Bylsma |
| 6,238,409 B1 | 5/2001 | Hojeibane |
| 6,241,721 B1 | 6/2001 | Cozean et al. |
| D444,874 S | 7/2001 | Haffner et al. |
| 6,297,228 B1 | 10/2001 | Clark |
| 6,319,274 B1 | 11/2001 | Shadduck |
| 6,328,747 B1 | 12/2001 | Nun |
| 6,375,642 B1 | 4/2002 | Grieshaber et al. |
| 6,398,809 B1 | 6/2002 | Hoffmann et al. |
| 6,409,752 B1 | 6/2002 | Boatman et al. |
| 6,450,984 B1 | 9/2002 | Lynch et al. |
| 6,464,724 B1 | 10/2002 | Lynch et al. |
| 6,471,666 B1 | 10/2002 | Odrich |

(56) References Cited

U.S. PATENT DOCUMENTS

| | | |
|---|---|---|
| 6,494,857 B1 | 12/2002 | Neuhann |
| 6,508,779 B1 | 1/2003 | Suson |
| 6,517,523 B1 | 2/2003 | Kaneko et al. |
| 6,524,275 B1 | 2/2003 | Lynch et al. |
| 6,533,764 B1 | 3/2003 | Haffner et al. |
| 6,533,768 B1 | 3/2003 | Hill |
| 6,544,208 B2 | 4/2003 | Ethier et al. |
| 6,544,249 B1 | 4/2003 | Yu et al. |
| 6,551,289 B1 | 4/2003 | Higuchi et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,699,210 B2 | 3/2004 | Williams et al. |
| 6,699,211 B2 | 3/2004 | Savage |
| 6,702,790 B1 | 3/2004 | Ross |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,198 B2 | 4/2005 | Brown |
| 6,899,717 B2 | 5/2005 | Weber et al. |
| 6,939,298 B2 | 9/2005 | Brown et al. |
| 6,955,656 B2 | 10/2005 | Bergheim et al. |
| 6,962,573 B1 | 11/2005 | Wilcox |
| 6,981,958 B1 | 1/2006 | Gharib et al. |
| 6,989,007 B2 | 1/2006 | Shadduck |
| 7,018,376 B2 | 3/2006 | Webb et al. |
| 7,094,225 B2 | 8/2006 | Tu et al. |
| 7,125,119 B2 | 10/2006 | Farberov |
| 7,133,137 B2 | 11/2006 | Shimmick |
| 7,135,009 B2 | 11/2006 | Tu et al. |
| 7,147,650 B2 | 12/2006 | Lee |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,207,980 B2 | 4/2007 | Christian et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,488,303 B1 | 2/2009 | Haffner et al. |
| 7,699,882 B2 | 4/2010 | Stamper et al. |
| 7,740,604 B2 | 6/2010 | Schieber et al. |
| 7,931,596 B2 | 4/2011 | Rachlin et al. |
| 7,967,772 B2 | 6/2011 | McKenzie et al. |
| 8,012,115 B2 | 9/2011 | Karageozian |
| 8,123,729 B2 | 2/2012 | Yamamoto et al. |
| 8,172,899 B2 | 5/2012 | Silvestrini et al. |
| 8,267,882 B2 | 9/2012 | Euteneuer et al. |
| 8,282,592 B2 | 10/2012 | Schieber et al. |
| 8,308,701 B2 | 11/2012 | Horvath et al. |
| 8,337,509 B2 | 12/2012 | Schieber et al. |
| 8,372,026 B2 | 2/2013 | Schieber et al. |
| 8,414,518 B2 | 4/2013 | Schieber et al. |
| 8,425,449 B2 | 4/2013 | Wardle et al. |
| 8,475,374 B2 | 7/2013 | Irazoqui et al. |
| 8,512,404 B2 | 8/2013 | Frion et al. |
| 8,529,494 B2 | 9/2013 | Euteneuer et al. |
| 8,540,659 B2 | 9/2013 | Berlin |
| 8,551,166 B2 | 10/2013 | Schieber et al. |
| 8,629,161 B2 | 1/2014 | Mizuno et al. |
| 8,636,647 B2 | 1/2014 | Silvestrini et al. |
| 8,647,659 B2 | 2/2014 | Robinson et al. |
| 8,657,776 B2 | 2/2014 | Wardle et al. |
| 8,663,150 B2 | 3/2014 | Wardle et al. |
| 8,663,303 B2 | 3/2014 | Horvath et al. |
| 8,734,377 B2 | 5/2014 | Schieber et al. |
| 8,808,222 B2 | 8/2014 | Schieber et al. |
| 8,939,948 B2 | 1/2015 | De Juan, Jr. et al. |
| 8,945,038 B2 | 2/2015 | Yablonski |
| 8,951,221 B2 | 2/2015 | Stegmann et al. |
| 8,961,447 B2 | 2/2015 | Schieber et al. |
| 8,974,511 B2 | 3/2015 | Horvath et al. |
| 9,039,650 B2 | 5/2015 | Schieber et al. |
| 9,050,169 B2 | 6/2015 | Schieber et al. |
| 9,066,750 B2 | 6/2015 | Wardle et al. |
| 9,066,783 B2 | 6/2015 | Euteneuer et al. |
| 9,155,655 B2 | 10/2015 | Wardle et al. |
| 9,211,213 B2 | 12/2015 | Wardle et al. |
| 9,226,852 B2 | 1/2016 | Schieber et al. |
| 9,301,875 B2 | 4/2016 | Tu et al. |
| 9,351,874 B2 | 5/2016 | Schieber et al. |
| 9,358,156 B2 | 6/2016 | Wardle et al. |
| 9,402,767 B2 | 8/2016 | Schieber et al. |
| 9,510,973 B2 | 12/2016 | Wardle |
| 9,579,234 B2 | 2/2017 | Wardle et al. |
| 9,603,741 B2 | 3/2017 | Berlin |
| 9,610,196 B2 | 4/2017 | Schieber et al. |
| 9,636,254 B2 | 5/2017 | Yu et al. |
| 9,642,746 B2 | 5/2017 | Berlin |
| 9,693,899 B2 | 7/2017 | Wardle et al. |
| 9,693,901 B2 | 7/2017 | Horvath et al. |
| 9,693,902 B2 | 7/2017 | Euteneuer et al. |
| 9,757,276 B2 | 9/2017 | Penhasi |
| 9,775,729 B2 | 10/2017 | McClain et al. |
| 9,820,883 B2 | 11/2017 | Berlin |
| 9,833,357 B2 | 12/2017 | Berlin |
| 9,931,243 B2 | 4/2018 | Wardle et al. |
| 10,159,601 B2 | 12/2018 | Berlin |
| 10,335,314 B2 | 7/2019 | Berlin |
| 10,363,168 B2 | 7/2019 | Schieber et al. |
| 10,390,993 B1 | 8/2019 | Berlin |
| 10,406,025 B2 | 9/2019 | Wardle et al. |
| 10,492,949 B2 | 12/2019 | Wardle et al. |
| 10,537,474 B2 | 1/2020 | Euteneuer et al. |
| 10,617,558 B2 | 4/2020 | Schieber et al. |
| 10,687,978 B2 | 6/2020 | Berlin |
| 10,709,547 B2 | 7/2020 | Schieber |
| 11,026,836 B2 | 6/2021 | Wardle et al. |
| 11,135,088 B2 | 10/2021 | Wardle et al. |
| 2001/0002438 A1 | 5/2001 | Sepetka et al. |
| 2001/0021835 A1 | 9/2001 | Mitchell et al. |
| 2002/0003546 A1 | 1/2002 | Mochimaru et al. |
| 2002/0013546 A1 | 1/2002 | Grieshaber et al. |
| 2002/0013572 A1 | 1/2002 | Berlin |
| 2002/0052653 A1 | 5/2002 | Durgin |
| 2002/0072673 A1 | 6/2002 | Yamamoto et al. |
| 2002/0082591 A1 | 6/2002 | Haefliger |
| 2002/0133168 A1 | 9/2002 | Smedley et al. |
| 2002/0143284 A1 | 10/2002 | Tu et al. |
| 2002/0165504 A1 | 11/2002 | Sharp et al. |
| 2002/0165522 A1 | 11/2002 | Holmen |
| 2002/0193805 A1 | 12/2002 | Ott et al. |
| 2003/0004457 A1 | 1/2003 | Andersson |
| 2003/0014092 A1 | 1/2003 | Neuhann |
| 2003/0040754 A1 | 2/2003 | Mitchell et al. |
| 2003/0055372 A1 | 3/2003 | Lynch et al. |
| 2003/0060748 A1 | 3/2003 | Baikoff |
| 2003/0060752 A1 | 3/2003 | Bergheim et al. |
| 2003/0060784 A1 | 3/2003 | Hilgers et al. |
| 2003/0093084 A1 | 5/2003 | Nissan et al. |
| 2003/0097151 A1 | 5/2003 | Smedley et al. |
| 2003/0105456 A1 | 6/2003 | Lin |
| 2003/0125351 A1 | 7/2003 | Azuma et al. |
| 2003/0175324 A1 | 9/2003 | Robinson et al. |
| 2003/0181848 A1 | 9/2003 | Bergheim et al. |
| 2003/0187384 A1 | 10/2003 | Bergheim et al. |
| 2003/0212387 A1 | 11/2003 | Kurtz et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0024453 A1 | 2/2004 | Castillejos |
| 2004/0030302 A1 | 2/2004 | Kamata et al. |
| 2004/0070761 A1 | 4/2004 | Horvath et al. |
| 2004/0082939 A1 | 4/2004 | Berlin |
| 2004/0088048 A1 | 5/2004 | Richter et al. |
| 2004/0092856 A1 | 5/2004 | Dahan |
| 2004/0098124 A1 | 5/2004 | Freeman et al. |

(56) References Cited

U.S. PATENT DOCUMENTS

| | | |
|---|---|---|
| 2004/0102729 A1 | 5/2004 | Haffner et al. |
| 2004/0106975 A1 | 6/2004 | Solovay et al. |
| 2004/0111050 A1 | 6/2004 | Smedley et al. |
| 2004/0116909 A1 | 6/2004 | Neuberger et al. |
| 2004/0122380 A1 | 6/2004 | Utterberg |
| 2004/0127843 A1 | 7/2004 | Tu et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0199149 A1 | 10/2004 | Myers et al. |
| 2004/0199171 A1 | 10/2004 | Akahoshi |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225357 A1 | 11/2004 | Worst et al. |
| 2004/0228013 A1 | 11/2004 | Goldstein et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0260228 A1 | 12/2004 | Lynch et al. |
| 2005/0041200 A1 | 2/2005 | Rich |
| 2005/0043722 A1 | 2/2005 | Lin |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0125003 A1 | 6/2005 | Pinchuk et al. |
| 2005/0131514 A1 | 6/2005 | Hijlkema et al. |
| 2005/0149114 A1 | 7/2005 | Cartledge et al. |
| 2005/0154443 A1 | 7/2005 | Linder et al. |
| 2005/0165385 A1 | 7/2005 | Simon |
| 2005/0192527 A1 | 9/2005 | Gharib et al. |
| 2005/0197667 A1 | 9/2005 | Chan et al. |
| 2005/0203542 A1 | 9/2005 | Weber et al. |
| 2005/0209549 A1 | 9/2005 | Bergheim et al. |
| 2005/0209550 A1 | 9/2005 | Bergheim et al. |
| 2005/0240168 A1 | 10/2005 | Neuberger et al. |
| 2005/0244464 A1 | 11/2005 | Hughes |
| 2005/0245916 A1 | 11/2005 | Connor |
| 2005/0250788 A1 | 11/2005 | Tu et al. |
| 2005/0260186 A1 | 11/2005 | Bookbinder et al. |
| 2005/0266047 A1 | 12/2005 | Tu et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0279369 A1 | 12/2005 | Lin |
| 2005/0288619 A1 | 12/2005 | Gharib et al. |
| 2005/0288745 A1 | 12/2005 | Andersen et al. |
| 2006/0020247 A1 | 1/2006 | Kagan et al. |
| 2006/0021623 A1 | 2/2006 | Miller et al. |
| 2006/0032507 A1 | 2/2006 | Tu |
| 2006/0052879 A1 | 3/2006 | Kolb |
| 2006/0069340 A1 | 3/2006 | Simon |
| 2006/0074375 A1 | 4/2006 | Bergheim et al. |
| 2006/0079828 A1 | 4/2006 | Brown |
| 2006/0084907 A1 | 4/2006 | Bergheim et al. |
| 2006/0084954 A1 | 4/2006 | Zadoyan et al. |
| 2006/0106370 A1 | 5/2006 | Baerveldt et al. |
| 2006/0110428 A1 | 5/2006 | deJuan et al. |
| 2006/0116626 A1 | 6/2006 | Smedley et al. |
| 2006/0129141 A1 | 6/2006 | Lin |
| 2006/0149194 A1 | 7/2006 | Conston et al. |
| 2006/0154981 A1 | 7/2006 | Klimko et al. |
| 2006/0155238 A1 | 7/2006 | Shields |
| 2006/0155265 A1 | 7/2006 | Juhasz et al. |
| 2006/0155300 A1 | 7/2006 | Stamper et al. |
| 2006/0167421 A1 | 7/2006 | Quinn |
| 2006/0167466 A1 | 7/2006 | Dusek |
| 2006/0173397 A1 | 8/2006 | Tu et al. |
| 2006/0173399 A1 | 8/2006 | Rodgers et al. |
| 2006/0178674 A1 | 8/2006 | McIntyre |
| 2006/0189915 A1 | 8/2006 | Camras et al. |
| 2006/0189916 A1 | 8/2006 | Bas et al. |
| 2006/0189917 A1 | 8/2006 | Mayr et al. |
| 2006/0195055 A1 | 8/2006 | Bergheim et al. |
| 2006/0195056 A1 | 8/2006 | Bergheim et al. |
| 2006/0195187 A1 | 8/2006 | Stegmann et al. |
| 2006/0200113 A1 | 9/2006 | Haffner et al. |
| 2006/0224146 A1 | 10/2006 | Lin |
| 2006/0241749 A1 | 10/2006 | Tu et al. |
| 2006/0259021 A1 | 11/2006 | Lin |
| 2006/0264971 A1 | 11/2006 | Akahoshi |
| 2006/0276759 A1 | 12/2006 | Kinast et al. |
| 2007/0010827 A1 | 1/2007 | Tu et al. |
| 2007/0021725 A1 | 1/2007 | Villette |
| 2007/0027452 A1 | 2/2007 | Varner et al. |
| 2007/0073275 A1 | 3/2007 | Conston et al. |
| 2007/0088432 A1 | 4/2007 | Solovay et al. |
| 2007/0093794 A1 | 4/2007 | Wang et al. |
| 2007/0093796 A1 | 4/2007 | Raksi et al. |
| 2007/0106200 A1 | 5/2007 | Levy |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0121120 A1 | 5/2007 | Schachar |
| 2007/0135681 A1 | 6/2007 | Chin et al. |
| 2007/0173791 A1 | 7/2007 | Raksi |
| 2007/0179520 A1 | 8/2007 | West |
| 2007/0191863 A1 | 8/2007 | De Juan, Jr. et al. |
| 2007/0202186 A1 | 8/2007 | Yamamoto et al. |
| 2007/0208325 A1 | 9/2007 | Kurtz |
| 2007/0219509 A1 | 9/2007 | Tashiro et al. |
| 2007/0219541 A1 | 9/2007 | Kurtz |
| 2007/0235543 A1 | 10/2007 | Zadoyan et al. |
| 2007/0236771 A1 | 10/2007 | Zadoyan et al. |
| 2007/0265582 A1 | 11/2007 | Kaplan et al. |
| 2007/0270945 A1 | 11/2007 | Kobayashi et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2007/0293872 A1 | 12/2007 | Peyman |
| 2007/0298068 A1 | 12/2007 | Badawi et al. |
| 2008/0015488 A1 | 1/2008 | Tu et al. |
| 2008/0027519 A1 | 1/2008 | Guerrero |
| 2008/0045878 A1 | 2/2008 | Bergheim et al. |
| 2008/0058704 A1 | 3/2008 | Hee et al. |
| 2008/0058777 A1 | 3/2008 | Kurtz et al. |
| 2008/0082088 A1 | 4/2008 | Kurtz et al. |
| 2008/0091224 A1 | 4/2008 | Griffis et al. |
| 2008/0119827 A1 | 5/2008 | Kurtz et al. |
| 2008/0228127 A1 | 9/2008 | Burns et al. |
| 2008/0278687 A1 | 11/2008 | Somani |
| 2008/0288082 A1 | 11/2008 | Deal |
| 2008/0312661 A1 | 12/2008 | Downer et al. |
| 2009/0005852 A1 | 1/2009 | Gittings et al. |
| 2009/0028953 A1 | 1/2009 | Yamamoto et al. |
| 2009/0030363 A1 | 1/2009 | Gellman |
| 2009/0030381 A1 | 1/2009 | Lind et al. |
| 2009/0036843 A1 | 2/2009 | Erskine |
| 2009/0043321 A1 | 2/2009 | Conston et al. |
| 2009/0054723 A1 | 2/2009 | Khairkhahan et al. |
| 2009/0069786 A1 | 3/2009 | Vesely et al. |
| 2009/0082862 A1 | 3/2009 | Schieber et al. |
| 2009/0104248 A1 | 4/2009 | Rapacki et al. |
| 2009/0118716 A1 | 5/2009 | Brownell |
| 2009/0118717 A1 | 5/2009 | Brownell et al. |
| 2009/0118718 A1 | 5/2009 | Raksi et al. |
| 2009/0131921 A1 | 5/2009 | Kurtz et al. |
| 2009/0132040 A1 | 5/2009 | Frion |
| 2009/0137988 A1 | 5/2009 | Kurtz |
| 2009/0138081 A1 | 5/2009 | Bergheim et al. |
| 2009/0157062 A1 | 6/2009 | Hauger et al. |
| 2009/0171327 A1 | 7/2009 | Kurtz et al. |
| 2009/0182421 A1 | 7/2009 | Silvestrini et al. |
| 2009/0198248 A1 | 8/2009 | Yeung et al. |
| 2009/0204053 A1 | 8/2009 | Nissan et al. |
| 2009/0247955 A1 | 10/2009 | Yamamoto et al. |
| 2009/0259126 A1 | 10/2009 | Saal et al. |

(56) References Cited

U.S. PATENT DOCUMENTS

| | | |
|---|---|---|
| 2009/0281520 A1 | 11/2009 | Highley et al. |
| 2009/0281530 A1 | 11/2009 | Korn |
| 2009/0291423 A1 | 11/2009 | Hara |
| 2010/0004580 A1 | 1/2010 | Lynch et al. |
| 2010/0036488 A1 | 2/2010 | de Juan et al. |
| 2010/0057072 A1 | 3/2010 | Roman et al. |
| 2010/0114309 A1 | 5/2010 | de Juan et al. |
| 2010/0121342 A1* | 5/2010 | Schieber ............... A61M 31/00 606/108 |
| 2010/0137981 A1 | 6/2010 | Silvestrini et al. |
| 2010/0173866 A1 | 7/2010 | Hee et al. |
| 2010/0191176 A1 | 7/2010 | Ho et al. |
| 2010/0191177 A1 | 7/2010 | Chang et al. |
| 2010/0234726 A1 | 9/2010 | Sirimanne et al. |
| 2010/0234790 A1 | 9/2010 | Tu et al. |
| 2010/0262174 A1 | 10/2010 | Sretavan et al. |
| 2010/0324543 A1 | 12/2010 | Kurtz et al. |
| 2010/0331858 A1 | 12/2010 | Simaan et al. |
| 2011/0028948 A1 | 2/2011 | Raksi et al. |
| 2011/0028949 A1 | 2/2011 | Raksi et al. |
| 2011/0028950 A1 | 2/2011 | Raksi et al. |
| 2011/0028951 A1 | 2/2011 | Raksi et al. |
| 2011/0028952 A1 | 2/2011 | Raksi et al. |
| 2011/0028953 A1 | 2/2011 | Raksi et al. |
| 2011/0028954 A1 | 2/2011 | Raksi et al. |
| 2011/0028955 A1 | 2/2011 | Raksi |
| 2011/0028957 A1 | 2/2011 | Raksi et al. |
| 2011/0028958 A1 | 2/2011 | Raksi et al. |
| 2011/0098809 A1 | 4/2011 | Wardle et al. |
| 2011/0196487 A1 | 8/2011 | Badawi et al. |
| 2011/0218523 A1 | 9/2011 | Robl |
| 2011/0224597 A1 | 9/2011 | Stegmann et al. |
| 2012/0010702 A1 | 1/2012 | Stegmann et al. |
| 2012/0021397 A1 | 1/2012 | Van Dalen et al. |
| 2012/0022424 A1 | 1/2012 | Yamamoto et al. |
| 2012/0035524 A1 | 2/2012 | Silvestrini |
| 2012/0191064 A1 | 7/2012 | Conston et al. |
| 2012/0271272 A1 | 10/2012 | Hammack et al. |
| 2012/0283557 A1 | 11/2012 | Berlin |
| 2012/0302861 A1 | 11/2012 | Marshall et al. |
| 2013/0023837 A1 | 1/2013 | Becker |
| 2013/0182223 A1 | 7/2013 | Wardle et al. |
| 2013/0267887 A1 | 10/2013 | Kahook et al. |
| 2014/0018720 A1 | 1/2014 | Horvath et al. |
| 2014/0066821 A1 | 3/2014 | Freidland et al. |
| 2014/0066831 A1 | 3/2014 | Silvestrini et al. |
| 2015/0022780 A1 | 1/2015 | John et al. |
| 2015/0045714 A1 | 2/2015 | Horvath et al. |
| 2015/0057591 A1 | 2/2015 | Horvath et al. |
| 2015/0305939 A1 | 10/2015 | Vera et al. |
| 2015/0305940 A1 | 10/2015 | Vera et al. |
| 2015/0313759 A1 | 11/2015 | Vera et al. |
| 2017/0143541 A1 | 5/2017 | Badawi et al. |
| 2017/0172794 A1 | 6/2017 | Vamer et al. |
| 2017/0172800 A1 | 6/2017 | Romoda et al. |
| 2017/0202708 A1 | 7/2017 | Berlin |
| 2017/0239272 A1 | 8/2017 | Ambati et al. |
| 2017/0281409 A1 | 10/2017 | Haffner et al. |
| 2017/0360609 A9 | 12/2017 | Schieber et al. |
| 2018/0369017 A1 | 12/2018 | Schieber et al. |
| 2019/0076296 A1 | 3/2019 | Van Meter et al. |
| 2019/0343679 A1 | 11/2019 | Wardle et al. |
| 2019/0380874 A1 | 12/2019 | Schieber et al. |
| 2020/0060876 A1 | 2/2020 | Wardle et al. |
| 2020/0085620 A1 | 3/2020 | Euteneuer |
| 2020/0197221 A1 | 6/2020 | Schieber et al. |
| 2020/0222238 A1 | 7/2020 | Schieber et al. |
| 2020/0261270 A1 | 8/2020 | Berlin |
| 2021/0030590 A1 | 2/2021 | Blanda et al. |
| 2022/0054314 A1 | 2/2022 | Van Meter et al. |
| 2022/0096271 A1 | 3/2022 | Wardle et al. |

FOREIGN PATENT DOCUMENTS

| | | |
|---|---|---|
| EP | 0168201 B1 | 6/1988 |
| EP | 0957949 A1 | 11/1996 |
| EP | 0766544 B1 | 5/1998 |
| EP | 1615604 B1 | 8/2009 |
| EP | 2193821 A1 | 6/2010 |
| EP | 1715827 B1 | 12/2010 |
| EP | 2380622 A1 | 10/2011 |
| EP | 2468327 A1 | 6/2012 |
| EP | 2471563 A1 | 7/2012 |
| EP | 1833440 B1 | 8/2012 |
| EP | 1732484 B1 | 8/2017 |
| EP | 1740153 B2 | 8/2017 |
| EP | 3205333 A1 | 8/2017 |
| JP | 10504978 A | 5/1998 |
| JP | 11123205 A | 5/1999 |
| JP | 2002542872 A | 12/2002 |
| JP | 2006517848 A | 8/2006 |
| JP | 2006289075 A | 10/2006 |
| JP | 2009523545 A | 6/2009 |
| JP | 2010509003 A | 3/2010 |
| JP | 2011502649 A | 1/2011 |
| JP | 2012527318 A | 11/2012 |
| WO | WO96/20742 A1 | 7/1996 |
| WO | WO99/01063 A1 | 1/1999 |
| WO | WO99/45868 A1 | 9/1999 |
| WO | WO00/07525 A1 | 2/2000 |
| WO | WO00/64389 A1 | 11/2000 |
| WO | WO00/64393 A1 | 11/2000 |
| WO | WO00/67687 A1 | 11/2000 |
| WO | WO01/89437 A2 | 11/2001 |
| WO | WO01/97727 A1 | 12/2001 |
| WO | WO02/36052 A1 | 5/2002 |
| WO | WO02/074052 A2 | 9/2002 |
| WO | WO02/080811 A2 | 10/2002 |
| WO | WO03/015659 A2 | 2/2003 |
| WO | WO03/045290 A1 | 6/2003 |
| WO | WO2004/054643 A1 | 7/2004 |
| WO | WO2004/093761 A1 | 11/2004 |
| WO | WO2005/105197 A1 | 11/2005 |
| WO | WO2006/066103 A2 | 6/2006 |
| WO | WO2007/035356 A2 | 3/2007 |
| WO | WO2007/047744 A2 | 4/2007 |
| WO | WO2007/087061 A2 | 8/2007 |
| WO | WO2008/002377 A1 | 1/2008 |
| WO | WO2008/005873 A2 | 1/2008 |
| WO | WO2009/120960 A2 | 10/2009 |
| WO | WO2011/053512 A1 | 5/2011 |
| WO | WO2011/057283 A1 | 5/2011 |
| WO | WO2011/106781 A1 | 9/2011 |
| WO | WO2011/150045 A1 | 12/2011 |
| WO | WO2012/051575 A2 | 4/2012 |
| WO | 2012083143 A1 | 6/2012 |

OTHER PUBLICATIONS

Bahler, et al.; Trabecular bypass stents decrease intraocular pressure in cultured human anterior segments; Amer. Journal of Ophthalmology; vol. 138, No. 6; pp. 988-994.e2; Dec. 2004.

Cambridge Dictionary; Sensor (definition); 2 pages; retrived from the internet (http://dictionary.cambridge.org/define.asp?dict=CALD &key=71811 >) on Aug. 14, 2018.

D'Ermo, et al.; Our results with the operation of ab externo trabeculotomy; Ophthalmologica; vol. 163; pp. 347-355; Feb. 1971.

Dietlein et al.; Morphological variability of the trabecular meshwork in glaucoma patients: implications for non-perforating glaucoma surgery; British Journal of Ophthalmology; 84(12); pp. 1354-1359; Dec. 2000.

Ellingsen et al.; Trabeculotomy and sinusotomy in enucleated human eyes; Investigative Ophthalmology; vol. 11; pp. 21-28; Jan. 1972.

Grant; Experimental aqueous perfusion in enucleated human eyes; Archives of Ophthalmology; vol. 69; pp. 783-801; Jun. 1963.

Huang et al.; Optical coherence tomography; Science; 254(5035); pp. 1178-1181; 12 pages (Author Manuscript); Nov. 1991.

(56) References Cited

OTHER PUBLICATIONS

Johnstone et al.; "Microsurgery of Schlemm's Canal and the Human Aqueous Outflow System;" American Journal of Ophthalmology, vol. 76 (6): 906-917; Dec. 1973.
Johnstone; Aqueous humor outflow system overview; Becker-Shaffer's Diagnosis and Therapy of the Glaucomas; Part 2 Aqueous Humor Dynamics; Chapter 3; pp. 25-46; Mosby Elseveir; (year of pub. sufficiently earlier than effective US filing date and any foreign priority date) 2009.
Kirkness et al.; The Use of Silicone Drainage Tubing to Control Post-Keratoplasty Glaucoma; Eye; 2 (pt 5); pp. 583-590; Apr. 1988.
Lee et al.; Aqueous-venous shunt and intraocular pressure. Preliminary report of animal studies; Investigative Ophthalmology; vol. 5; No. 1; pp. 59-64; Feb. 1966.
Lee et al.; Short-pulsed neodymium-YAG laser trabeculotomy. An in vivo morphological study in the human eye; Investigative Ophthalmology and Visual Science; 29(11); pp. 1698-1707; Nov. 1988.
Lynch, Mary G.; U.S. Appl. No. 60/131,030 entitled "Devices and methods for treating glaucoma by enhancing aqueous outflow through schlemm's canal and anterior chamber angle," filed Apr. 26, 1999.
Macmilla Online Dictionary; Detector (definition); Macmilla On Line Dictionary; 2 pages; retrived from the internet (https://www.macmillandictionary.com/dictionary/british/detector) on Aug. 14, 2018.
Mäepea et al.; The pressures in the episcleral veins, schlemm's canal and the trabecular meshwork in monkeys: effects of changes in intraocular pressure; Exp. Eye Res .; vol. 49; pp. 645-663; Oct. 1989.
Molteno et al.; Long Tube Implants in the Management of Glaucoma; SA Medical Journal: 26; pp. 1062-1066; Jun. 1976.
Molteno; New implant for drainage in glaucoma; Brit. J. Ophthal; 53; pp. 606-615; Sep. 1969.
Moses, Robert; The effect of intraocular pressure on resistance to outflow; Survey of Ophthalmology; vol. 22; No. 2; pp. 88-100; Sep.-Oct. 1977.
Nakamura et al.; Femtosecond laser photodisruption of primate trabecular meshwork: an ex vivo study; Investigative Ophthalmology and Visual Science; 50(3); pp. 1198-1204; Mar. 2009.
Owen; A moving-mirror gonioscope for retinal surgery; British Journal of Ophthalmology; 61(3); pp. 246-247; Mar. 1977 .
Oxford Dictionaries; Detector (definition); 1 page; retrieved from the internet (https://en.oxforddictionaries.com/definition/detector) on Aug. 14, 2018.
Oxford Dictionaries; Sensor (definition); 1 page; retrieved from te internet (http://www.askoxford.com/concise_oed/sensor?view=uk>) on Aug. 14, 2018.
Radhakrishnan et al.; Real-time optical coherence tomography of the anterior segment at 1310 nm; Archives of Opthhalmology; 119(8); pp. 1179-1185; Aug. 2001.
Rosenquist et al.; Outflow resistance of enucleated human eyes at two different perfusion pressures and different extents of trabeculotomy; Current Eye Res .; vol. 8; No. 12; pp. 1233-1240; Dec. 1989.
Savage, James; Gonioscopy in the management of glaucoma; Am. Academy of Ophthalmology; Focal Points; vol. XXIV; No. 3; pp. 1-14; Mar. 2006.
Schocket et al.; Anterior Chamber Tube Shunt to an Encircling Band in the Treatment of Neovascular Glaucoma and other Refractory Glaucomas; Ophthalmology; 92; pp. 553-562; Apr. 1985.
Schultz, Jared; Canaloplasty procedure shows promise for open-angle glaucoma in European study; Ocular Surgery News; vol. 34; Mar. 1, 2007.
Smit et al.; Effects of viscoelastic injection into schlemm's canal in primate and human eyes; J. Am. Academy of Ophthalmology; vol. 109; No. 4; pp. 786-792; Apr. 2002.
Spiegel et al.; Schlemm's canal implant: a new method to lower intraocular pressure in patients with POAG ?; Ophthalmic Surgery and Lasers; vol. 30; No. 6; pp. 492-494; Jun. 1999.
Sugiyama et al.; Micro-Diaphragm Pressure Sensor; 1986 International Electron Devices Meeting; pp. 184-187; Dec. 7, 1986.
Toyran et al.; Femtosecond laser photodisruption of human trabecular meshwork: an in vitro study; Experimental Eye Research; 81(3); pp. 298-305; Sep. 2005.
Wilcox et al.; Hypothesis for Improving Accessory Filtration by Using Geometry; Journal of Glaucoma; 3; pp. 244-247; Fall 1994.
Wardle et al.; U.S. Appl. No. 17/314,699 entitled "Ocular implants for delivery into an anterior chamber of the eye," filed May 7, 2021.

\* cited by examiner

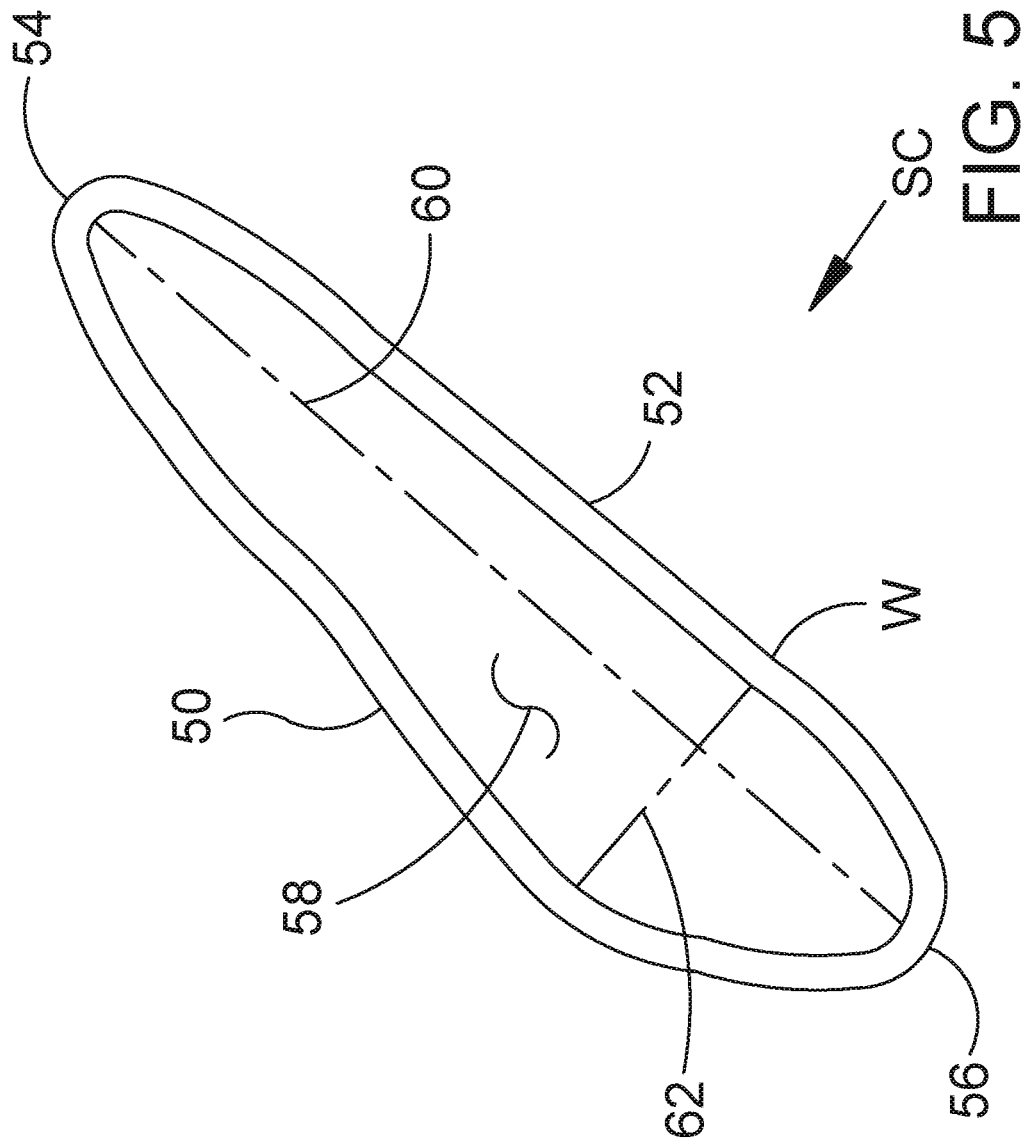

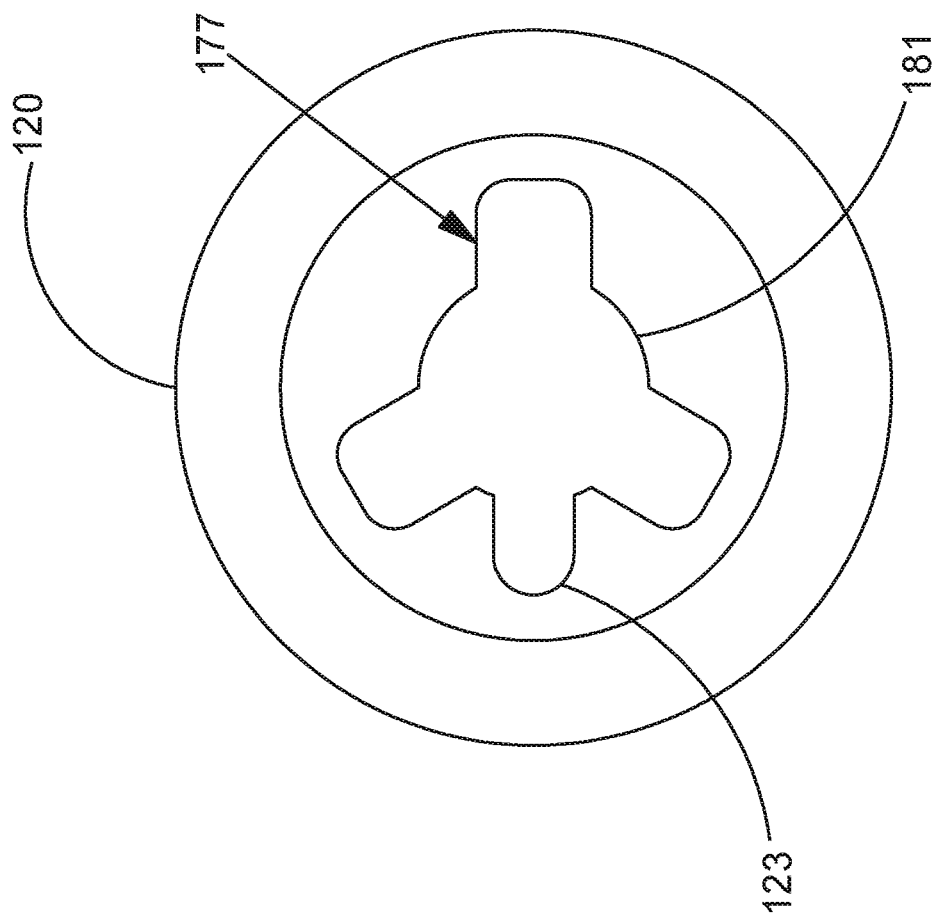

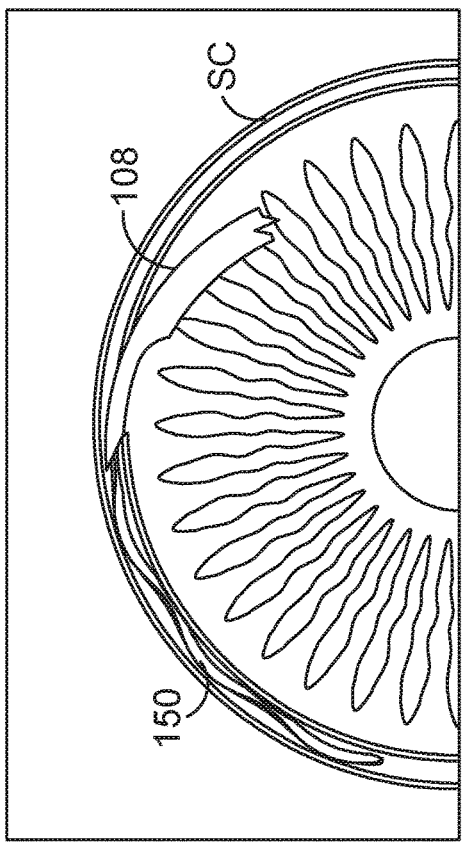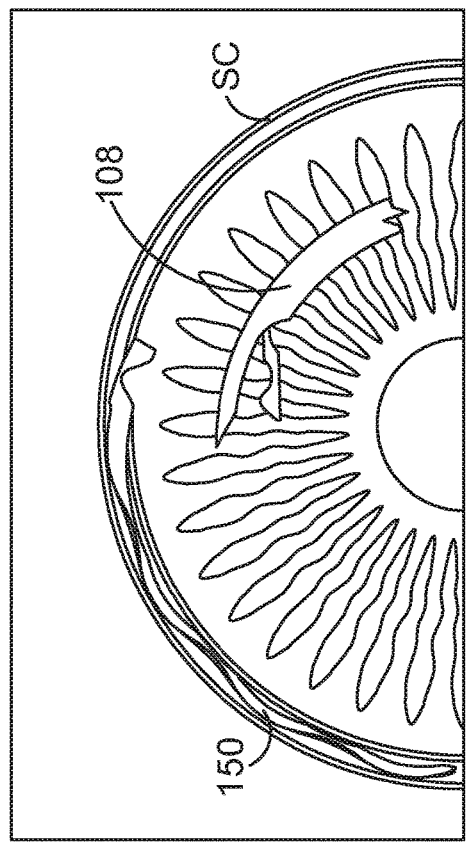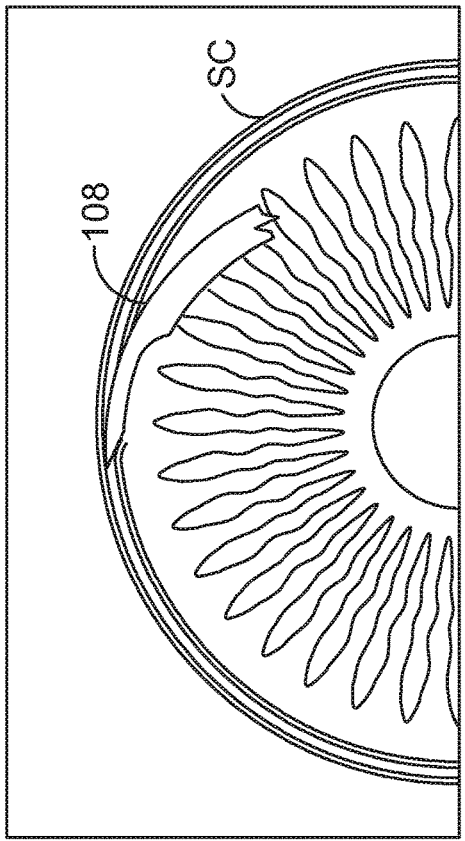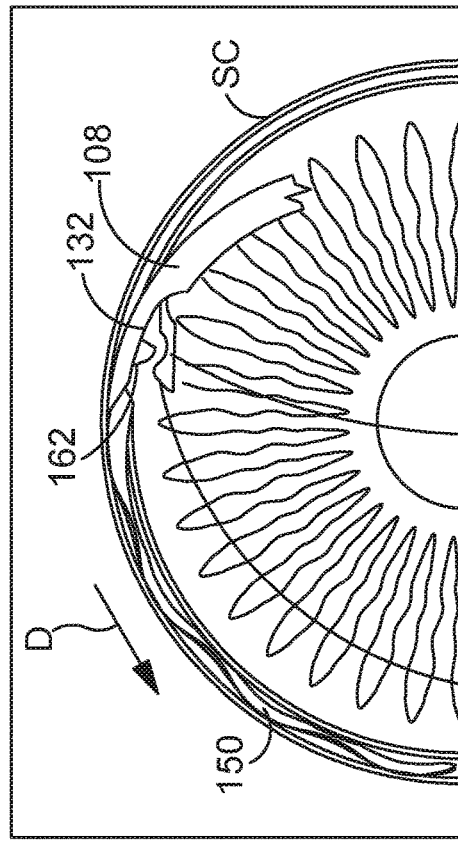

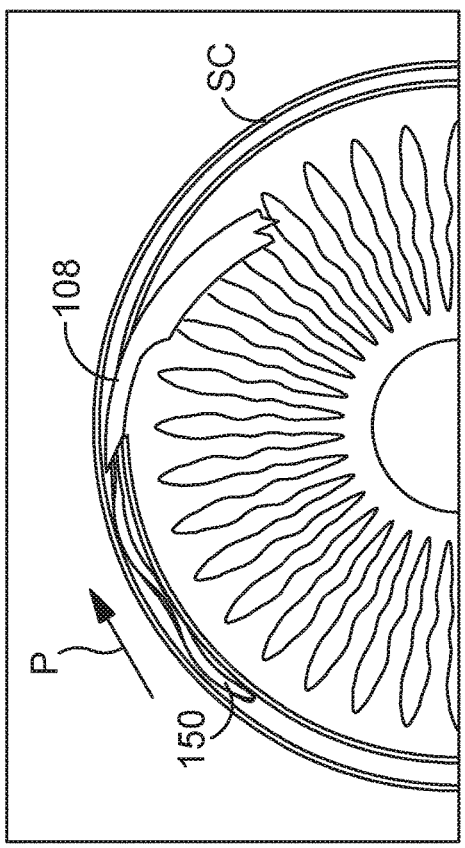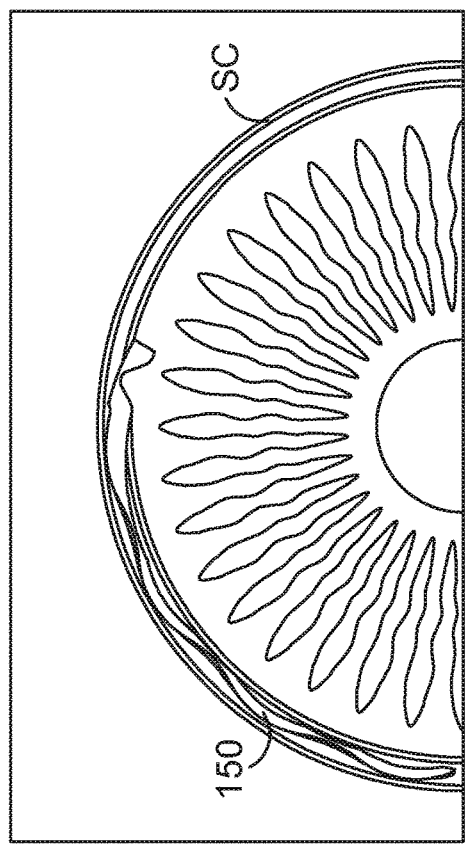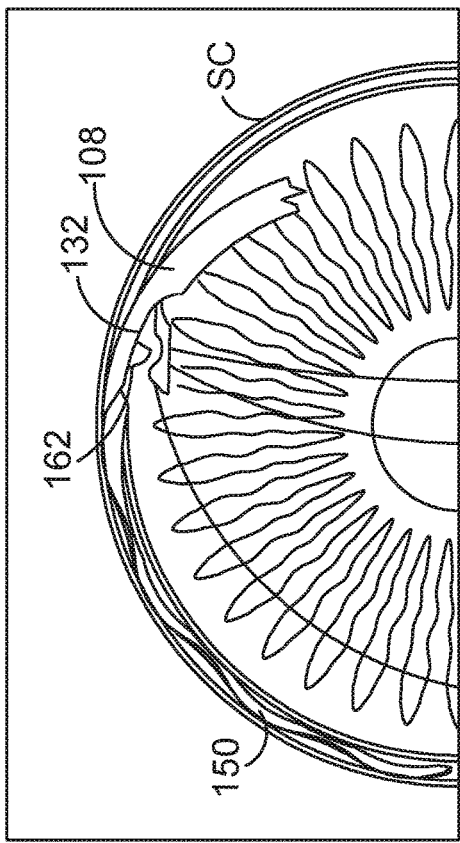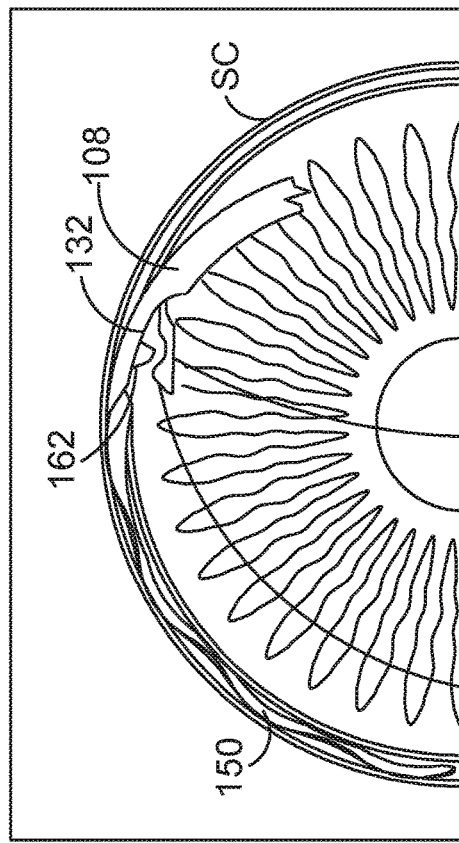

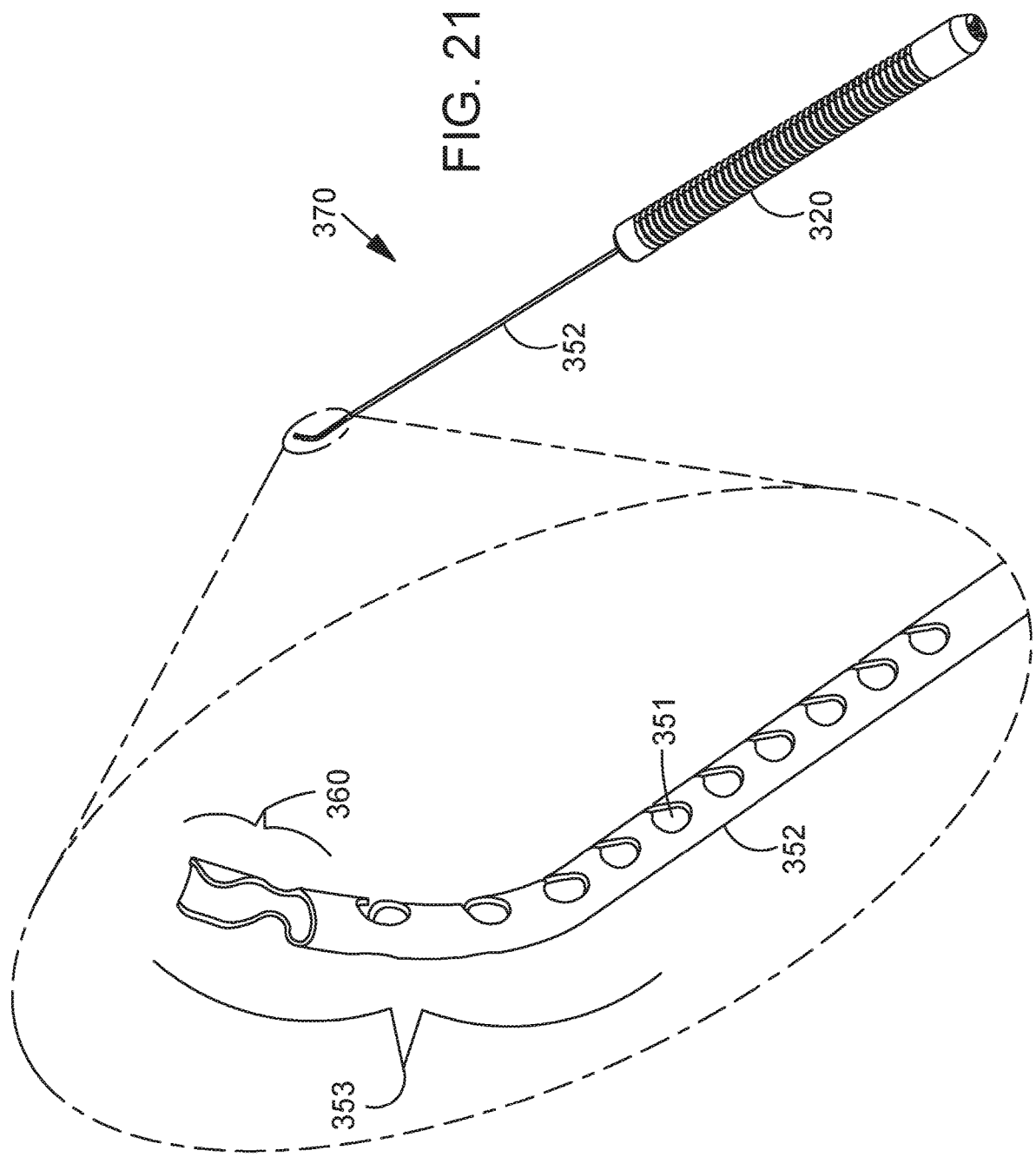

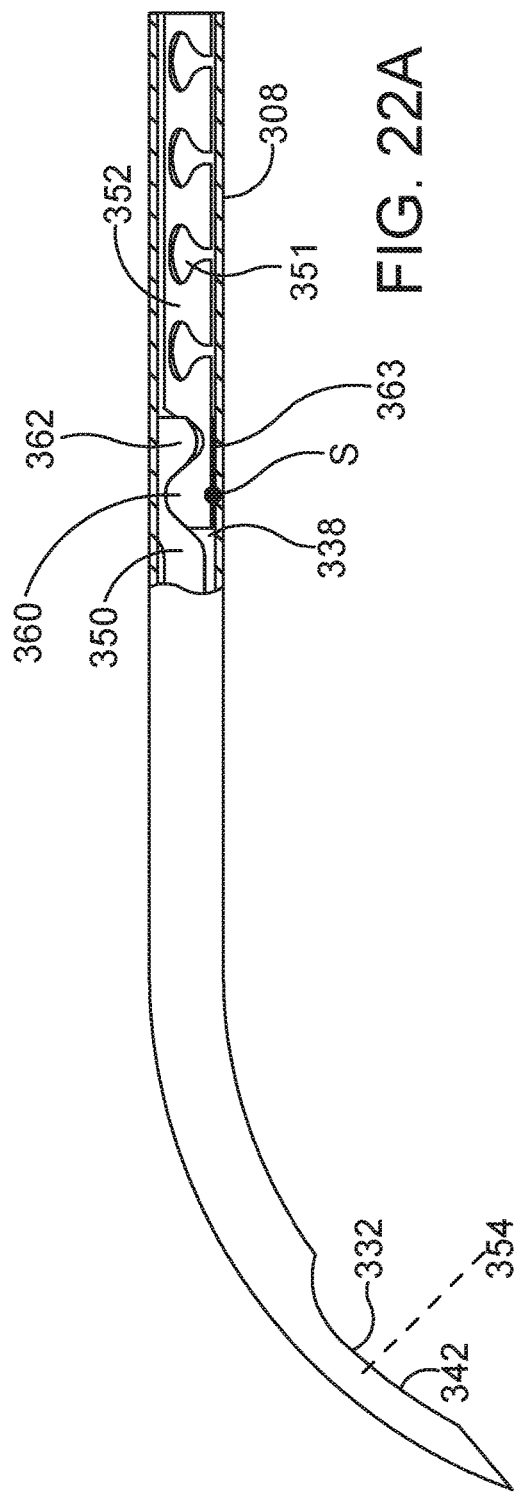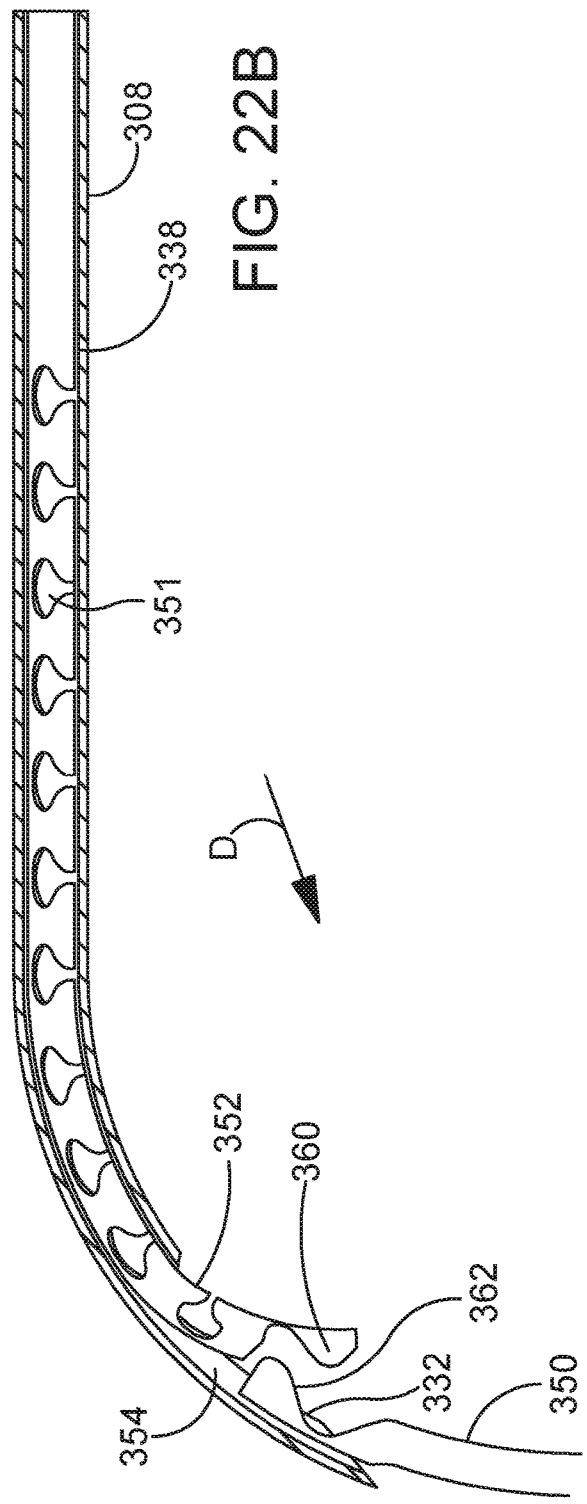

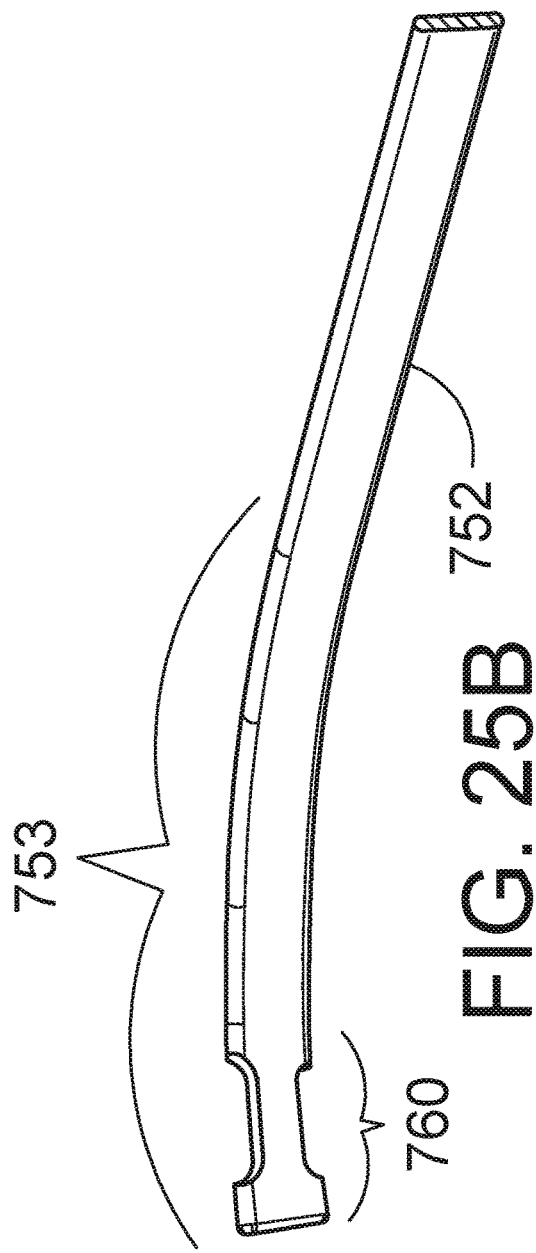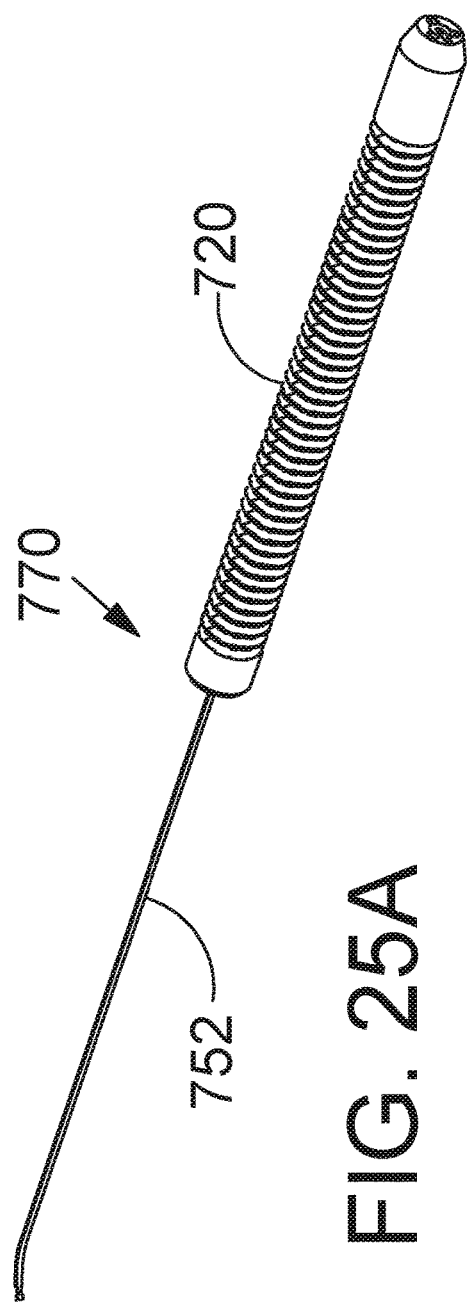

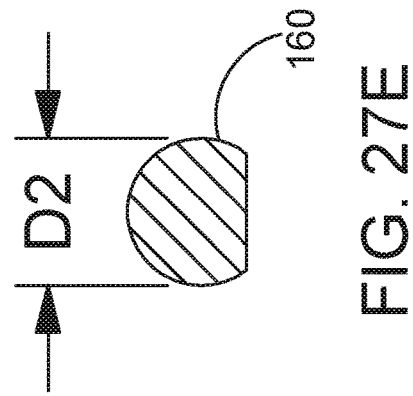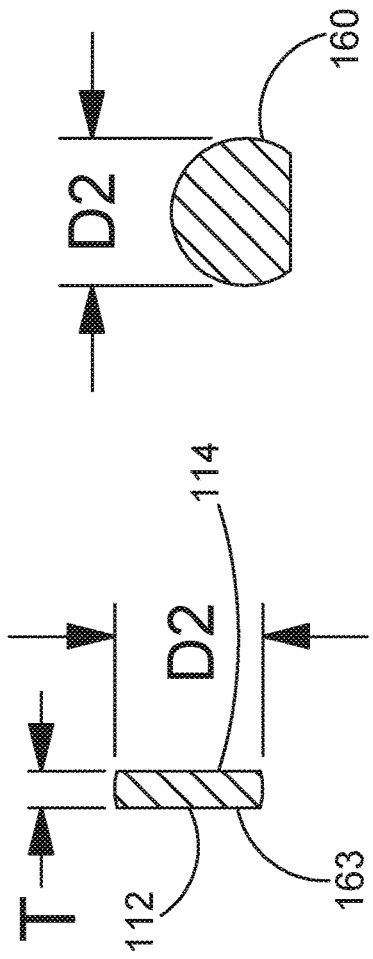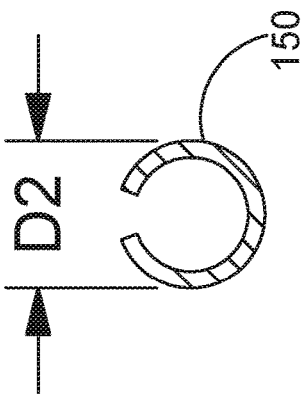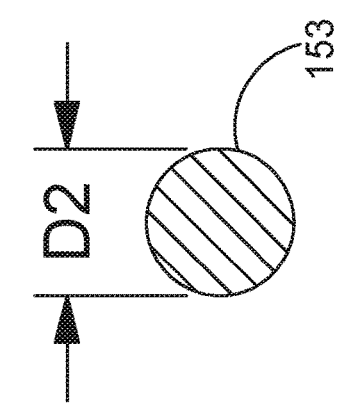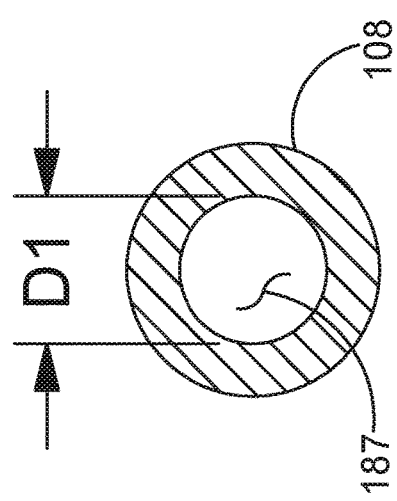

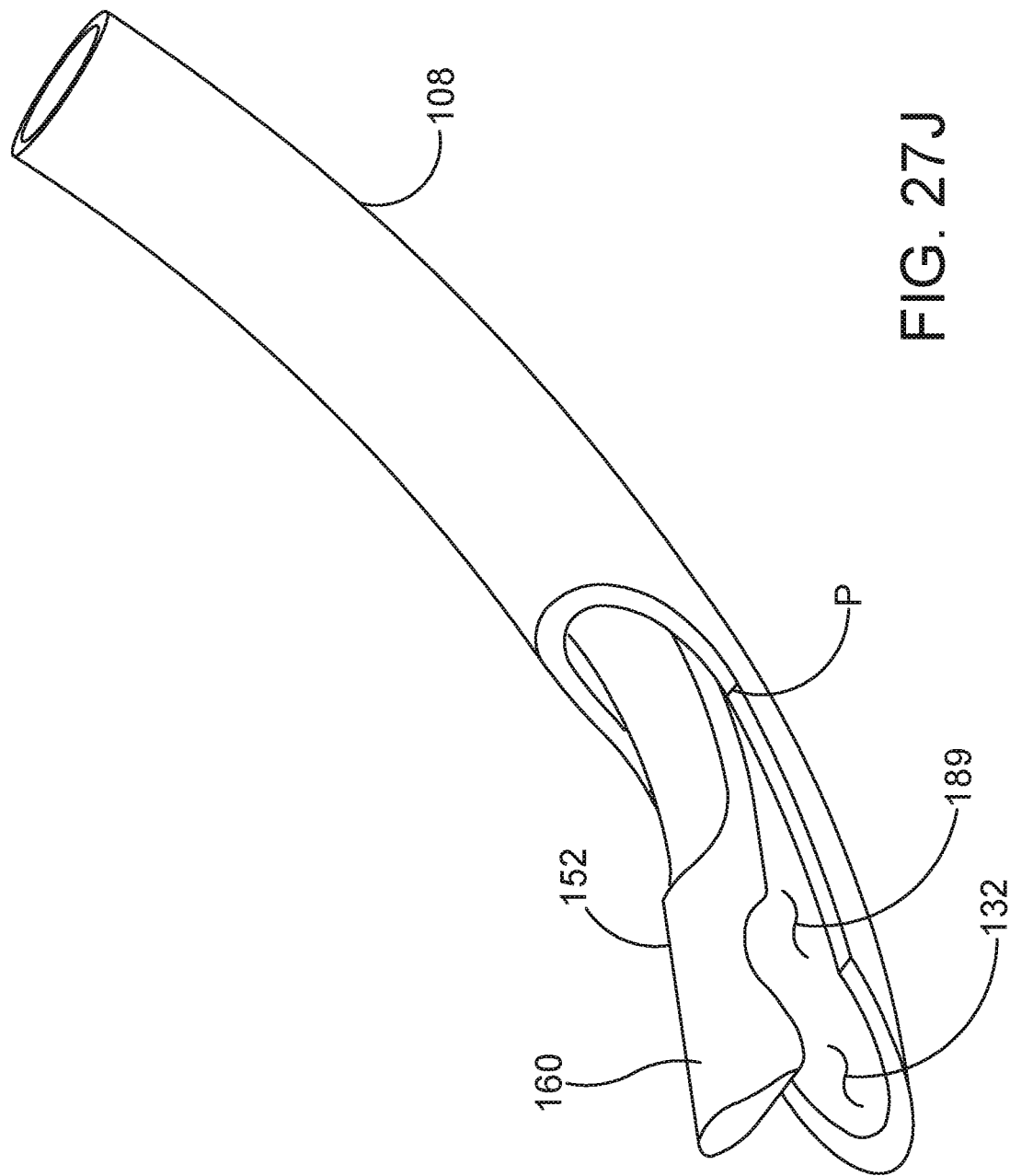

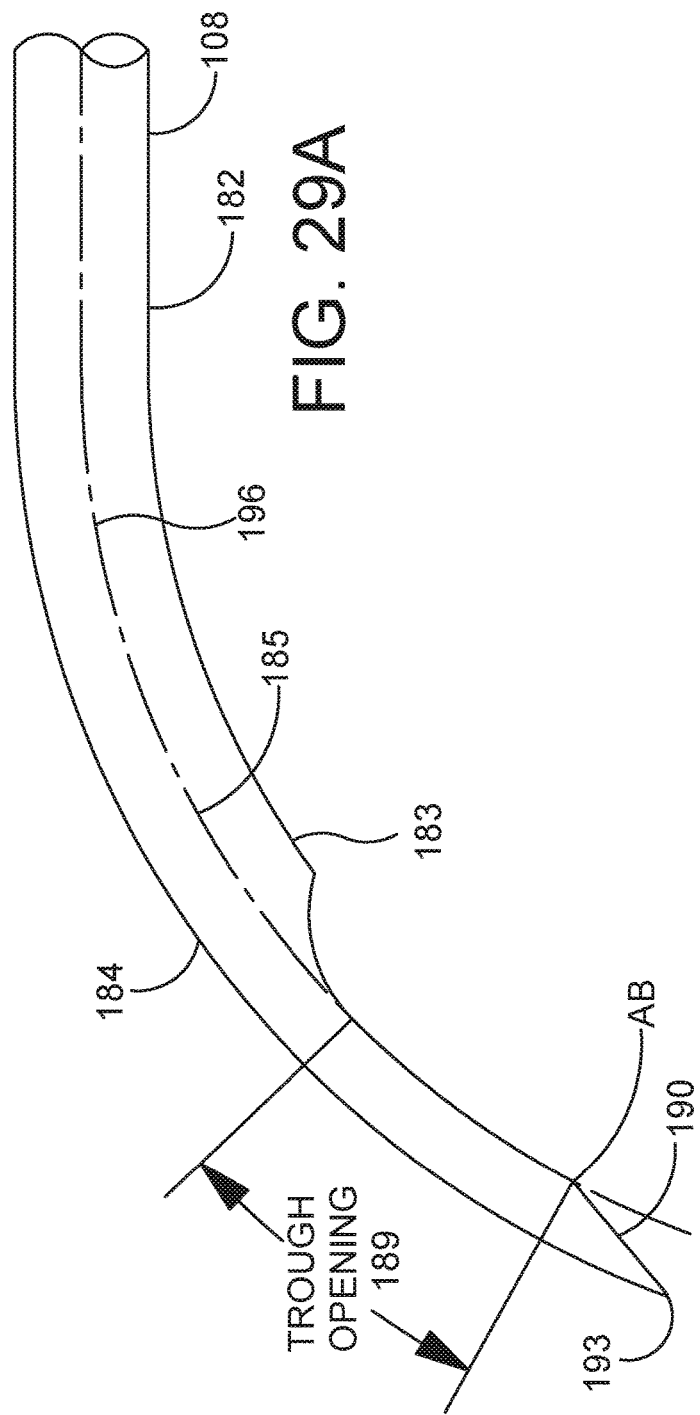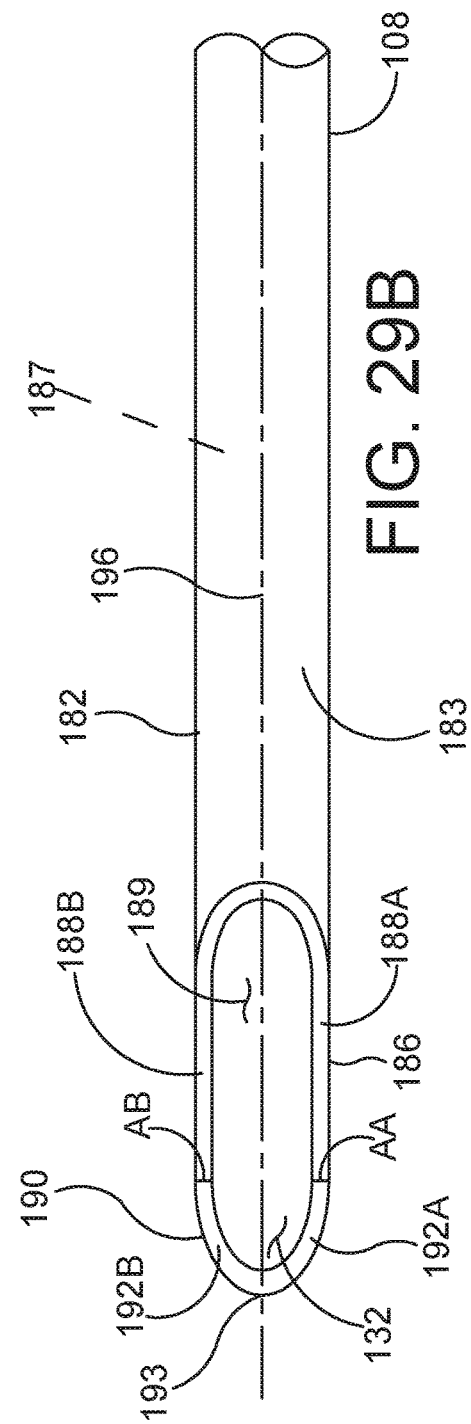

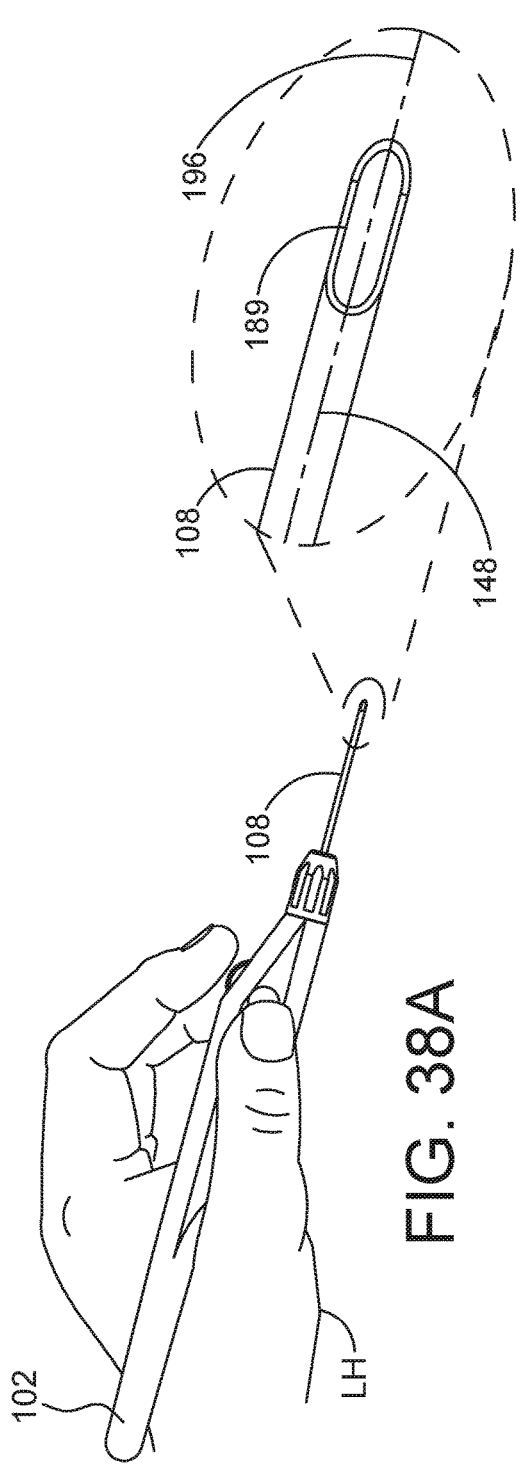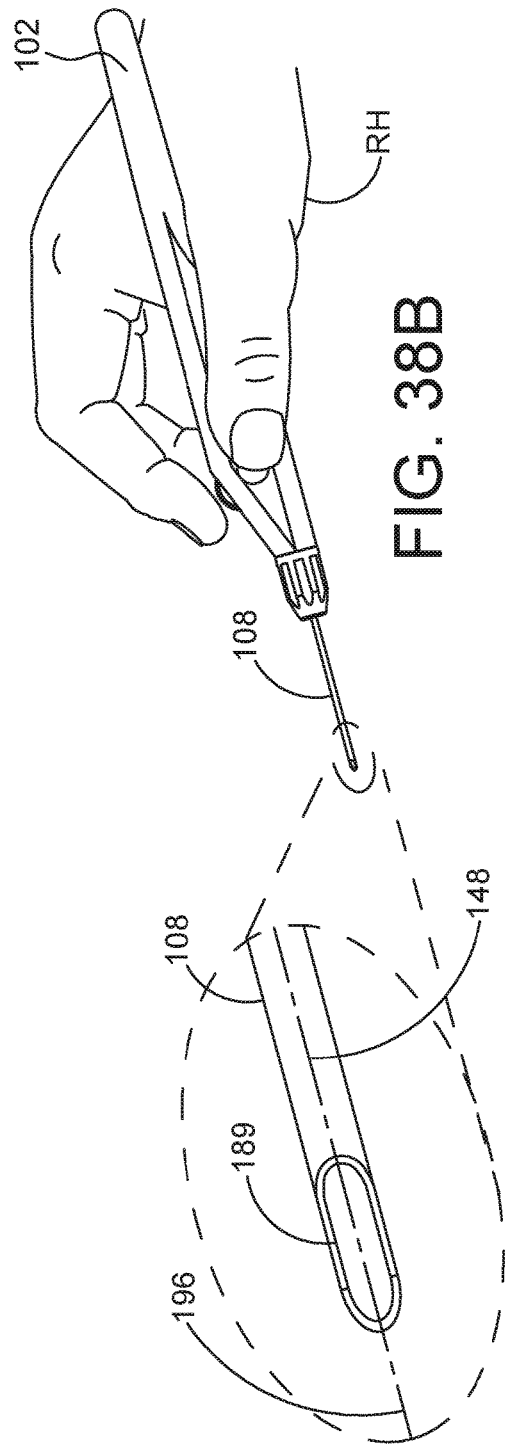

DELIVERING OCULAR IMPLANTS INTO THE EYE

CROSS-REFERENCE

This application is a continuation of U.S. application Ser. No. 14/363,409, filed Jun. 6, 2014, which is a national stage application under 35 U.S.C. 371, of International Application No. PCT/US2012/070626, filed Dec. 19, 2012, which is a continuation of U.S. application Ser. No. 13/330,592, filed Dec. 19, 2011, now U.S. Pat. No. 8,663,150, which applications are incorporated by reference in their entirety.

FIELD

The present invention relates generally to the medical devices and treatments for the eye. More particularly, the present invention relates to systems, devices and methods for delivering ocular implants into the eye for treating glaucoma.

INCORPORATION BY REFERENCE

All publications and patent applications mentioned in this specification are herein incorporated by reference to the same extent as if each individual publication or patent application was specifically and individually indicated to be incorporated by reference.

BACKGROUND

According to a draft report by The National Eye Institute (NEI) at The United States National Institutes of Health (NIH), glaucoma is now the leading cause of irreversible blindness worldwide and the second leading cause of blindness, behind cataract, in the world. Thus, the NEI draft report concludes, "it is critical that significant emphasis and resources continue to be devoted to determining the pathophysiology and management of this disease." Glaucoma researchers have found a strong correlation between high intraocular pressure and glaucoma. For this reason, eye care professionals routinely screen patients for glaucoma by measuring intraocular pressure using a device known as a tonometer. Many modern tonometers make this measurement by blowing a sudden puff of air against the outer surface of the eye.

The eye can be conceptualized as a ball filled with fluid. There are two types of fluid inside the eye. The cavity behind the lens is filled with a viscous fluid known as vitreous humor. The cavities in front of the lens are filled with a fluid known as aqueous humor. Whenever a person views an object, he or she is viewing that object through both the vitreous humor and the aqueous humor.

Whenever a person views an object, he or she is also viewing that object through the cornea and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the anterior chamber of the eye through the trabecular meshwork and into Schlemm's canal as new aqueous humor is secreted by the epithelial cells of the ciliary body. This excess aqueous humor enters the venous blood stream from Schlemm's canal and is carried along with the venous blood leaving the eye.

When the natural drainage mechanisms of the eye stop functioning properly, the pressure inside the eye begins to rise. Researchers have theorized prolonged exposure to high intraocular pressure causes damage to the optic nerve that transmits sensory information from the eye to the brain. This damage to the optic nerve results in loss of peripheral vision. As glaucoma progresses, more and more of the visual field is lost until the patient is completely blind.

In addition to drug treatments, a variety of surgical treatments for glaucoma have been performed. For example, shunts were implanted to direct aqueous humor from the anterior chamber to the extraocular vein (Lee and Scheppens, "Aqueous-venous shunt and intraocular pressure," Investigative Ophthalmology (February 1966)). Other early glaucoma treatment implants led from the anterior chamber to a sub-conjunctival bleb (e.g., U.S. Pat. Nos. 4,968,296 and 5,180,362). Still others were shunts leading from the anterior chamber to a point just inside Schlemm's canal (Spiegel et al., "Schlemm's canal implant: a new method to lower intraocular pressure in patients with POAG?" Ophthalmic Surgery and Lasers (June 1999); U.S. Pat. Nos. 6,450,984; 6,450,984).

SUMMARY OF THE DISCLOSURE

One aspect of the invention provides a method of deploying an ocular implant into Schlemm's canal of an eye. In some embodiments, the method includes the steps of inserting a distal end of a cannula through a cornea of the eye and into an anterior chamber of the eye, the cannula having a distal opening extending from the distal end and through a side wall; placing the distal opening of the cannula into fluid communication with Schlemm's canal; advancing the ocular implant distally through the cannula with a delivery tool engaged with the ocular implant, a proximal portion of the ocular implant engaging the delivery tool proximal to a distal portion of the delivery tool; and disengaging the ocular implant and the delivery tool when the proximal portion of the ocular implant reaches the cannula distal opening.

In some embodiments, the disengaging step includes the step of separating the distal portion of the delivery tool and the ocular implant from each other when the distal portion of the delivery tool passes through the distal opening of the cannula. In some such embodiments, the separating step is performed before the distal portion of the delivery tool reaches the distal end of the cannula. The separating step may include the step of maintaining contact between the ocular implant and the cannula and moving the distal portion of the delivery tool away from the cannula. In embodiments in which the distal portion of the delivery tool has an at-rest shape (such as, e.g., a curve having a smaller radius of curvature than a distal portion of the cannula), the separating step may also include the step of permitting the distal portion of the delivery tool to assume its at-rest shape.

In some embodiments, the inserting step includes the step of placing the distal end of the cannula in Schlemm's canal and a portion of the cannula distal opening outside of Schlemm's canal, the disengaging step including the step of disengaging the ocular implant and the delivery tool while the proximal portion of the ocular implant is disposed outside of Schlemm's canal. The disengaging step may also include the step of disengaging the ocular implant and the delivery tool while the proximal portion of the ocular implant is disposed inside the anterior chamber of the eye.

Some embodiments include the step of, after the disengaging step: re-engaging the delivery tool and the ocular implant; moving the delivery tool and the ocular implant in a proximal direction to withdraw at least a portion of the ocular implant from Schlemm's canal; advancing the ocular implant and delivery tool distally into Schlemm's canal; and disengaging the ocular implant and the delivery tool.

The method's disengaging step may also include the step of disengaging an interlocking portion of the delivery tool from a complementary interlocking portion of the ocular implant.

Another aspect of the invention provides a system with a cannula having a side wall defining a passageway, the cannula including an opening extending through a distal end and the side wall, the opening fluidly communicating with the passageway; an ocular implant disposed inside the passageway defined by the cannula; a delivery tool having a distal interlocking portion engaging a complementary interlocking portion of the ocular implant to form a mechanically interlocking connection when the interlocking portion of the delivery tool is proximal to the trough portion of the cannula.

In some embodiments, the distal interlocking portion of the delivery tool has an at-rest shape different from the shape of the cannula (such as, e.g., a curve having a smaller radius of curvature than a radius of curvature of the cannula), the cannula side wall preventing the delivery tool from assuming its at-rest shape when the interlocking portion of the delivery tool is proximal to the trough portion of the cannula.

In some embodiments, the system also has a cannula subassembly including the cannula and a delivery tool subassembly including the delivery tool, the delivery tool subassembly and the cannula subassembly engaging one another at a keyed interface, the keyed interface being configured to permit the delivery tool to slide along the passageway defined by the cannula, and the keyed interface being configured to prohibit rotation of the delivery tool subassembly relative to the cannula subassembly so that a predetermined orientation between the delivery tool and the cannula is maintained.

In some embodiments, the delivery tool subassembly includes a rotating rack gear defining a shaped hole having a predetermined shape in lateral cross-section and the cannula subassembly including a shaped portion configured to cooperate with the shaped hole of the rotating rack gear so that the delivery tool is free to slide along the passageway defined by the cannula and rotation of the delivery tool relative to the cannula is prohibited.

In some embodiments, the opening extending through the distal end and the side wall of the cannula is dimensioned and positioned such that, when the ocular implant reaches a predefined location along the passageway, the delivery tool will move toward an undeformed shape in which the interlocking portion of the delivery tool disengages the complementary interlocking portion of the ocular implant to release the ocular implant. The delivery tool may also have a cannula wall engagement surface diametrically opposite the interlocking portion and a reduced diameter portion proximal to the interlocking portion.

In some embodiments, the mechanically interlocking connection is configured to preclude axial and/or movement of the ocular implant relative to the delivery tool. The mechanically interlocking connection may include a peak of the delivery tool that is received in a valley of the ocular implant or a peak of the ocular implant that is received in a valley of the delivery tool.

In some embodiments, the system also includes a motion control mechanism configured to be operated from a location outside of the eye to move the delivery tool and the ocular implant along the passageway defined by the cannula.

In some embodiments, a system configured to deliver an ocular implant into Schlemm's canal of an eye is provided, comprising a curved cannula sized and configured to be advanced partially inside Schlemm's canal, the cannula having a distal trough portion which defines an open groove and a lumen extending along a length of the cannula into the distal trough portion, and a delivery tool slidably insertable into the lumen of the cannula, the delivery tool having a distal interlocking portion configured to mechanically interlock with a proximal interlocking portion of the ocular implant, the delivery tool being biased to bend radially through the open groove of the distal trough portion to disengage from the ocular implant when the distal interlocking portion of the delivery tool is advanced into the distal trough portion of the cannula.

In one embodiment, the delivery tool further comprises a ribbon portion proximal to the distal interlocking portion that is biased to assume a curved resting shape when no external forces are acting thereon.

In some embodiments, the ribbon portion is sized and configured to track along the widest part of an interior of the lumen of the cannula.

In other embodiments, a thickness of the ribbon portion is selected so as to enable the ribbon portion to preferentially bend along a preferential bending plane.

In alternative embodiments, the delivery tool is oriented within the cannula so that the preferential bending plane of the ribbon portion is co-planar with a curvature plane of the cannula.

In some embodiments, the ocular implant and the distal interlocking portion of the delivery tool both have an outer diameter slightly smaller than an inner diameter of the lumen of the cannula so that the distal interlocking portion can form a mechanically interlocking connection with the proximal interlocking portion of the ocular implant, the mechanically interlocking connection being configured to prevent jamming and unintentional release of the ocular implant.

In another embodiment, the distal trough portion has a trough depth greater than a height of the ocular implant so that a distal end of the ocular implant will travel between an inner surface of the distal trough portion and tissue stretched over the distal trough portion as the ocular implant is advanced.

In alternative embodiments, the cannula has a radius of curvature that is smaller than a radius of curvature of the ocular implant.

In one embodiment, the ribbon portion of the delivery tool has a resting radius of curvature that is smaller than a radius of curvature of the cannula.

In another embodiment, an ocular implant and delivery system, comprising an ocular implant sized and configured to be implanted inside Schlemm's canal of an eye, the ocular implant comprising a proximal interlocking portion, a curved cannula sized and configured to be advanced partially inside Schlemm's canal, the cannula having a distal trough portion which defines an open groove and a lumen extending along a length of the cannula into the distal trough portion, and a delivery tool slidably insertable into the lumen of the cannula, the delivery tool having a distal interlocking portion configured to mechanically interlock with the proximal interlocking portion of the ocular implant, the delivery tool being biased to bend radially through the open groove of the distal trough portion to disengage from the ocular implant when the distal interlocking portion of the delivery tool is advanced into the distal trough portion of the cannula.

In one embodiment, the delivery tool further comprises a ribbon portion proximal to the distal interlocking portion that is biased to assume a curved resting shape when no external forces are acting thereon.

In some embodiments, the ribbon portion is sized and configured to track along the widest part of an interior of the lumen of the cannula.

In other embodiments, a thickness of the ribbon portion is selected so as to enable the ribbon portion to preferentially bend along a preferential bending plane.

In alternative embodiments, the delivery tool is oriented within the cannula so that the preferential bending plane of the ribbon portion is co-planar with a curvature plane of the cannula.

In some embodiments, the ocular implant and the distal interlocking portion of the delivery tool both have an outer diameter slightly smaller than an inner diameter of the lumen of the cannula so that the distal interlocking portion can form a mechanically interlocking connection with the proximal interlocking portion of the ocular implant, the mechanically interlocking connection being configured to prevent jamming and unintentional release of the ocular implant.

In another embodiment, the distal trough portion has a trough depth greater than a height of the ocular implant so that a distal end of the ocular implant will travel between an inner surface of the distal trough portion and tissue stretched over the distal trough portion as the ocular implant is advanced.

In alternative embodiments, the cannula has a radius of curvature that is smaller than a radius of curvature of the ocular implant.

In one embodiment, the ribbon portion of the delivery tool has a resting radius of curvature that is smaller than a radius of curvature of the cannula.

A system for delivering an ocular implant into Schlemm's canal of an eye, the ocular implant comprising a wall having a wall thickness is also provided, the system comprising a cannula comprising a cannula wall, the cannula wall including first portion and a second portion, both portions of the cannula wall extending along a longitudinal center axis having a curved portion, the first portion of the cannula wall being disposed on a radially inward side of the longitudinal center axis and the second portion of the cannula wall being disposed on radially outward side of the longitudinal center axis, the cannula wall defining a trough opening through the first portion of the cannula wall and a lumen extending from the trough to a proximal end of the cannula, the cannula wall being sized and configured so that the trough and the lumen define a pathway extending from a location outside of the eye to a location inside Schlemm's canal when a distal point of the cannula is inside Schlemm's canal of the eye, a delivery tool extending into the lumen of the cannula, the delivery tool comprising a proximal portion, a distal interlocking portion, and a ribbon portion extending between the proximal portion and the distal interlocking portion, the distal interlocking portion of the delivery tool forming a mechanically interlocking connection with a complementary interlocking portion of the ocular implant when disposed in the lumen of the cannula, and the distal interlocking portion of the delivery tool moving through the trough opening of the cannula when the distal interlocking portion of the delivery tool reaches a predetermine location along the pathway so that the mechanically interlocking connection is broken.

In some embodiments, the ribbon portion of the delivery tool is biased to assume a curved resting shape when no external forces are acting thereon, the ribbon portion the delivery tool moves toward the curved resting shape when the delivery tool reaches the predetermined location along the pathway, and the interlocking portion of the delivery tool disengages the complementary interlocking portion of the ocular implant when the delivery tool is free to move toward the curved resting shape.

In other embodiments, the ribbon portion has an outer diameter and a thickness extending between a first major side of the ribbon portion and a second major side of the ribbon portion, and the outer diameter of the ribbon portion is only slightly smaller than the inner diameter of the cannula so that the ribbon portion tracks along the widest part of the cannula lumen and so that support provided by the cannula wall makes it less likely that ribbon portion will buckle.

In another embodiment, the outer diameter of the ribbon portion is smaller than the inner diameter of the cannula by a clearance value. In one embodiment, the clearance value is less than two times the wall thickness of the ocular implant. In other embodiments, the clearance value is between about 0.0005 inches and about 0.0010 inches.

In some embodiments, the thickness of the ribbon portion is selected so that the ribbon portion preferentially bends along a preferential bending plane. In another embodiment, an aspect ratio of the diameter to the thickness is selected so that the ribbon portion preferentially bends along a preferential bending plane.

In some embodiments, the delivery tool is oriented within the cannula so that a preferential bending plane of the ribbon portion is co-planar with a curvature plane of the cannula, the curvature plane being defined by the central axis of the cannula.

In some embodiments, the ocular implant and the distal interlocking portion of the delivery tool both have an outer diameter slightly smaller than the inner diameter of the cannula so that the distal interlocking portion can form a mechanically interlocking connection with the complimentary interlocking portion of the ocular implant, the mechanically interlocking connection being configured to prevent jamming and unintentional release of the ocular implant.

In some embodiments, the outer diameter of both the ocular implant and the distal interlocking portion of the delivery tool is smaller than the inner diameter of the cannula by a clearance value. In another embodiment, the clearance value is less than two times the wall thickness of the ocular implant. In another embodiment, the clearance value is between about 0.0005 inches and about 0.0010 inches.

In some embodiments, the trough opening has a width that is substantially equal to an inner diameter of the cannula and both the ribbon portion and the distal interlocking portion of the delivery tool have an outer diameter slightly smaller than the inner diameter of the cannula so that so that a distal portion of the delivery tool can pass through the trough opening when the delivery tool reaches the predetermined location along the pathway defined by the cannula.

In another embodiment, the outer diameter of both the ribbon portion and the distal interlocking portion of the delivery tool is smaller than the inner diameter of the cannula by a clearance value. In some embodiments, the clearance value is less than two times the wall thickness of the ocular implant. In other embodiments, the clearance value is between about 0.0005 inches and about 0.0010 inches.

In one embodiment, the trough has a trough depth greater than a height of the implant so that the distal end of the ocular implant will travel between an inner surface of the cannula and tissue stretched over the trough as the ocular implant is advanced along the path defined by the lumen and the trough.

In other embodiments, the trough is symmetrical about a curvature plane of the cannula so that the cannula can be used by both left handed users and right handed users in substantially the same way.

In an additional embodiment, the curved portion of the longitudinal central axis of the cannula has a radius of curvature that is smaller than a radius of curvature of the ocular implant.

In some embodiments, the ribbon portion of the delivery tool has a resting radius of curvature that is smaller than a radius of curvature of the curved portion of the longitudinal central axis of the cannula.

In another embodiment, a delivery tool subassembly and a cannula subassembly of the system engage one another at a keyed interface, the keyed interface being configured to permit the delivery tool to slide along the passageway defined by the cannula and the keyed interface being configured to prohibit rotation of the delivery tool subassembly relative to the cannula subassembly so that a coplanar relationship between a bending plane of the ribbon portion and a curvature plane of the cannula is maintained.

In one embodiment, the distal interlocking portion of the delivery tool engages the complementary interlocking portion of the ocular implant to form a mechanically interlocking connection when the distal interlocking portion of the delivery tool is disposed in the lumen of the cannula.

In another embodiment, the cannula wall holds the ribbon portion of the delivery tool in a deformed shape when the distal interlocking portion of the delivery tool is disposed in the lumen of the cannula.

A cannula for delivering an ocular implant into Schlemm's canal of an eye, the ocular implant having an implant height is provided, the cannula comprising a body comprising a first side and a second side, both sides of the body extending along a longitudinal center axis having a curved portion, the first side of the body being disposed on a radially inward side of the longitudinal center axis and the second side of the body being disposed on radially outward side of the longitudinal center axis, a tapered distal tip extending distally from the second side of the body, the body defining a trough that opens through the first side of the body and a lumen that extends from the trough to a proximal end of the body, the body being sized and configured so that the trough and the lumen define a pathway extending from a location outside of the eye to a location inside Schlemm's canal when a distal point of the tapered distal tip is inside Schlemm's canal of the eye, the tapered distal tip being shaped and configured to stretch Schlemm's canal tissues over a portion of the trough as the tapered distal tip is advanced into Schlemm's canal, and the trough having a trough depth greater than the implant height so that the distal end of the ocular implant will travel between an inner surface of the cannula and the tissue stretched over the trough as the ocular implant is advanced along the path defined by the lumen and the trough.

In some embodiments, the curved portion of the longitudinal central axis defines a curvature plane.

In other embodiments, the trough is symmetrical about the curvature plane. In an additional embodiment, the distal tip is symmetrical about the curvature plane.

In some embodiments, the trough comprises a first trough edge, a second trough edge, and an intermediate portion extending between the first trough edge and the second trough edge, the intermediate portion having a semi-circular transverse cross-sectional shape.

In another embodiment, the tip portion comprises a first leading edge, a second leading edge, and a semi-circular transverse cross-section extending between the first leading edge and the second leading edge.

In one embodiment, a tip chord extending between the first leading edge and the second leading edge has a chord length that increases as the tip portion extends proximally from a distal point thereof.

In some embodiments, the first leading edge has a first length and the second leading edge has a second length that is substantially equal to the first length.

In other embodiments, the first leading edge and the second leading edge extend between an inside surface of the body and an outside surface of the body.

In another embodiment, the inside surface of the body comprises a concave surface and the outside surface of the body comprises a convex surface.

In some embodiments, the first leading edge and the second leading edge both distally converge toward the distal point so that the tapered distal tip is generally V-shaped when viewed in plan.

In an additional embodiment, the distal point of the tip portion is sufficiently blunt to slide along the outer major wall of Schlemm's canal without cutting scleral tissue underlying the outer major wall of Schlemm's canal.

In some embodiments, at least a portion of the body is tubular.

In another embodiment, a curved portion of the body is shaped and dimensioned to be received inside the anterior chamber while a tubular portion of the body is extending through an incision in the dome shaped wall and the distal point of the body is inside Schlemm's canal.

In some embodiments, the curved portion of the longitudinal central axis has a radius of curvature that is substantially constant along a length thereof.

In another embodiment, the curved portion of the longitudinal central axis has a radius of curvature that varies along a length thereof.

In another embodiment, the curved portion of the longitudinal central axis has a radius of curvature that is smaller than a radius of curvature of the ocular implant.

In some embodiments, the body has a curved portion extending to the distal tip.

In some embodiments, the curved portion of the body has an angular span greater than 90 degrees.

In another embodiment, the curved portion of the body has an angular span of about 140.

In an additional embodiment, the trough depth extends between an inner surface of the body and a chord extending between a first trough edge and a second trough edge.

BRIEF DESCRIPTION OF THE DRAWINGS

FIG. 5 is an enlarged cross-sectional view further illustrating Schlemm's canal SC shown in the previous figure.

FIG. 8A is an end view of the rotating rack gear shown in FIG. 8.

FIG. 20A-FIG. 20H are a series of stylized plan views illustrating example methods in accordance with the detailed description and associated apparatus used while performing those methods.

FIG. 21 is a perspective view showing a delivery tool subassembly 370 that may be part of a delivery system (e.g., the delivery system shown in FIG. 8).

FIG. 22A is a stylized plan view further illustrating the delivery tool shown in FIG. 21. FIG. 22B is an additional stylized plan view illustrating the cannula, ocular implant, and delivery tool shown in FIG. 22A.

FIG. 25A is a perspective view showing a delivery tool subassembly that may be part of a delivery system (e.g., the delivery system shown in FIG. 8). FIG. 25B is a perspective view of the distal end of the delivery tool of this embodiment.

FIG. 27B is a cross-sectional view of cannula taken along section line B-B shown in FIG. 27A.

FIG. 27C, FIG. 27D and FIG. 27E are cross-sectional views of delivery tool shown in the previous figure.

FIG. 27F is a cross-sectional view of an ocular implant taken along section line F-F shown in FIG. 27A.

FIG. 27J is a perspective view showing an assembly including a cannula and a distal portion of a delivery tool.

FIG. 29A and FIG. 29B are plan views of the cannula shown in the previous figure.

FIG. 38A is a plan view showing a delivery system housing held in a left hand LH.

FIG. 38B is a plan view showing a delivery system housing held in a right hand RH.

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

Figure 1:
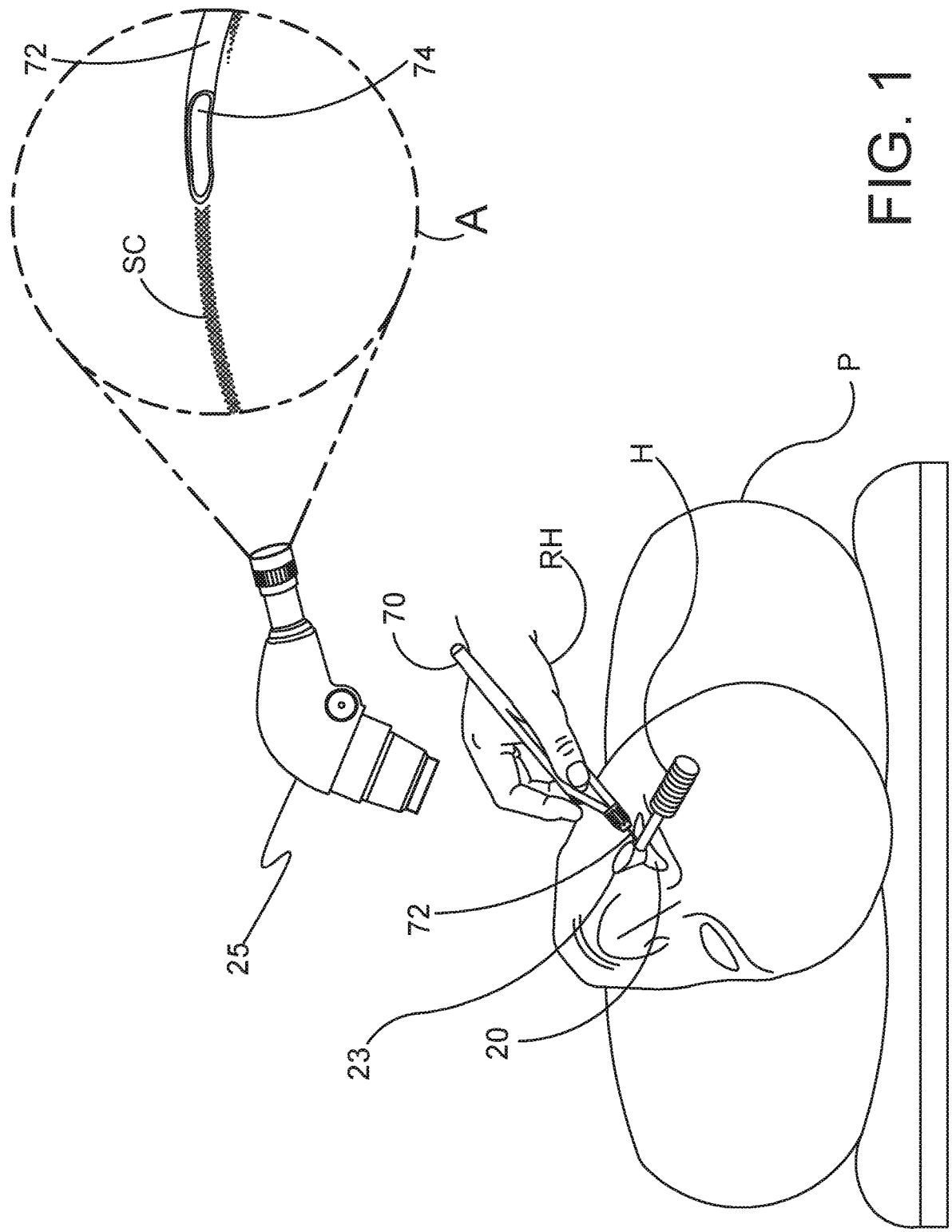
FIG. 1 is a stylized representation of a medical procedure in accordance with this detailed description.

FIG. 1 is a stylized representation of a medical procedure in accordance with this detailed description. In the procedure of FIG. 1, a physician is treating an eye 20 of a patient P. In the procedure of FIG. 1, the physician is holding a hand piece of a delivery system 70 in his or her right hand RH. The physician's left hand (not shown) may be used to hold the handle H of a gonio lens 23. Alternatively, some physicians may prefer holding the delivery system hand piece in the left hand and the gonio lens handle H in the right hand RH.

During the procedure illustrated in FIG. 1, the physician may view the interior of the anterior chamber using gonio lens 23 and a microscope 25. Detail A of FIG. 1 is a stylized simulation of the image viewed by the physician. A distal portion of a cannula 72 is visible in Detail A. A shadow-like line indicates the location of Schlemm's canal SC which is lying under various tissues (e.g., the trabecular meshwork) that surround the anterior chamber. A distal opening 74 of cannula 72 is positioned near Schlemm's canal SC of eye 20.

Methods in accordance with this detailed description may include the step of advancing the distal end of cannula 72 through the cornea of eye 20 so that a distal portion of cannula 72 is disposed in the anterior chamber of the eye. Cannula 72 may then be used to access Schlemm's canal of the eye, for example, by piercing the wall of Schlemm's canal with the distal end of cannula 72. Distal opening 74 of cannula 72 may be placed in fluid communication with a lumen defined by Schlemm's canal. The ocular implant may be advanced out of distal opening 74 and into Schlemm's canal. Insertion of the ocular implant into Schlemm's canal may facilitate the flow of aqueous humor out of the anterior chamber of the eye.

Figure 2:
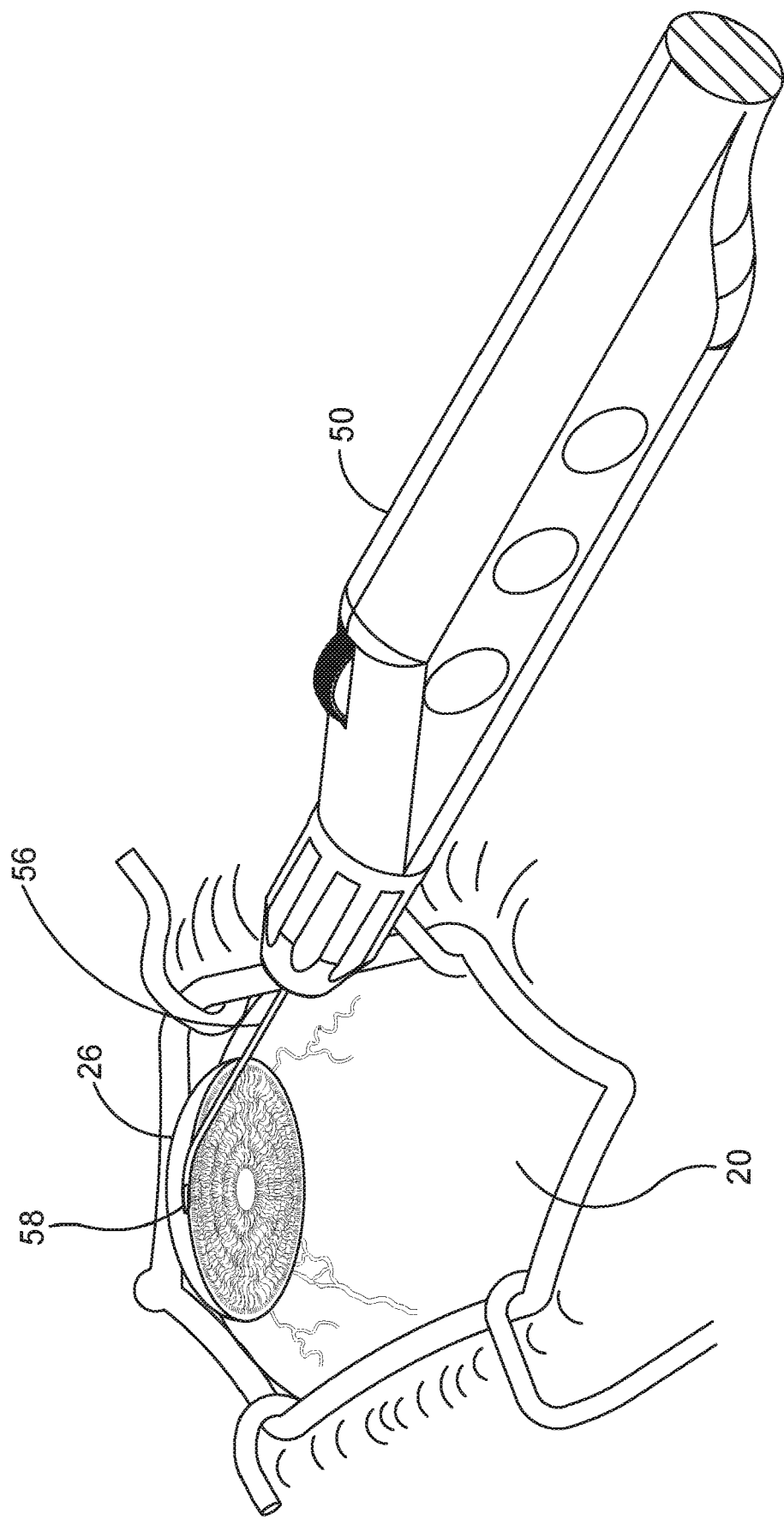
FIG. 2 is an enlarged perspective view further illustrating the delivery system and the eye shown in FIG. 1.

FIG. 2 is an enlarged perspective view further illustrating delivery system 50 and eye 20 shown in the previous figure. In FIG. 2, cannula 56 of delivery system 50 is shown extending through a cornea 26 of eye 20. A distal portion of cannula 56 is disposed inside the anterior chamber defined by cornea 26 of eye 20. In the embodiment of FIG. 2, cannula 56 is configured so that a distal opening 58 of cannula 56 can be placed in fluid communication with Schlemm's canal.

In the embodiment of FIG. 2, an ocular implant is disposed in a passageway defined by cannula 56. Delivery system 50 includes a mechanism that is capable of advancing and retracting the ocular implant along the length of cannula 56. The ocular implant may be placed in Schlemm's canal of eye 20 by advancing the ocular implant through the distal opening of cannula 56 while the distal opening is in fluid communication with Schlemm's canal.

Figure 3:
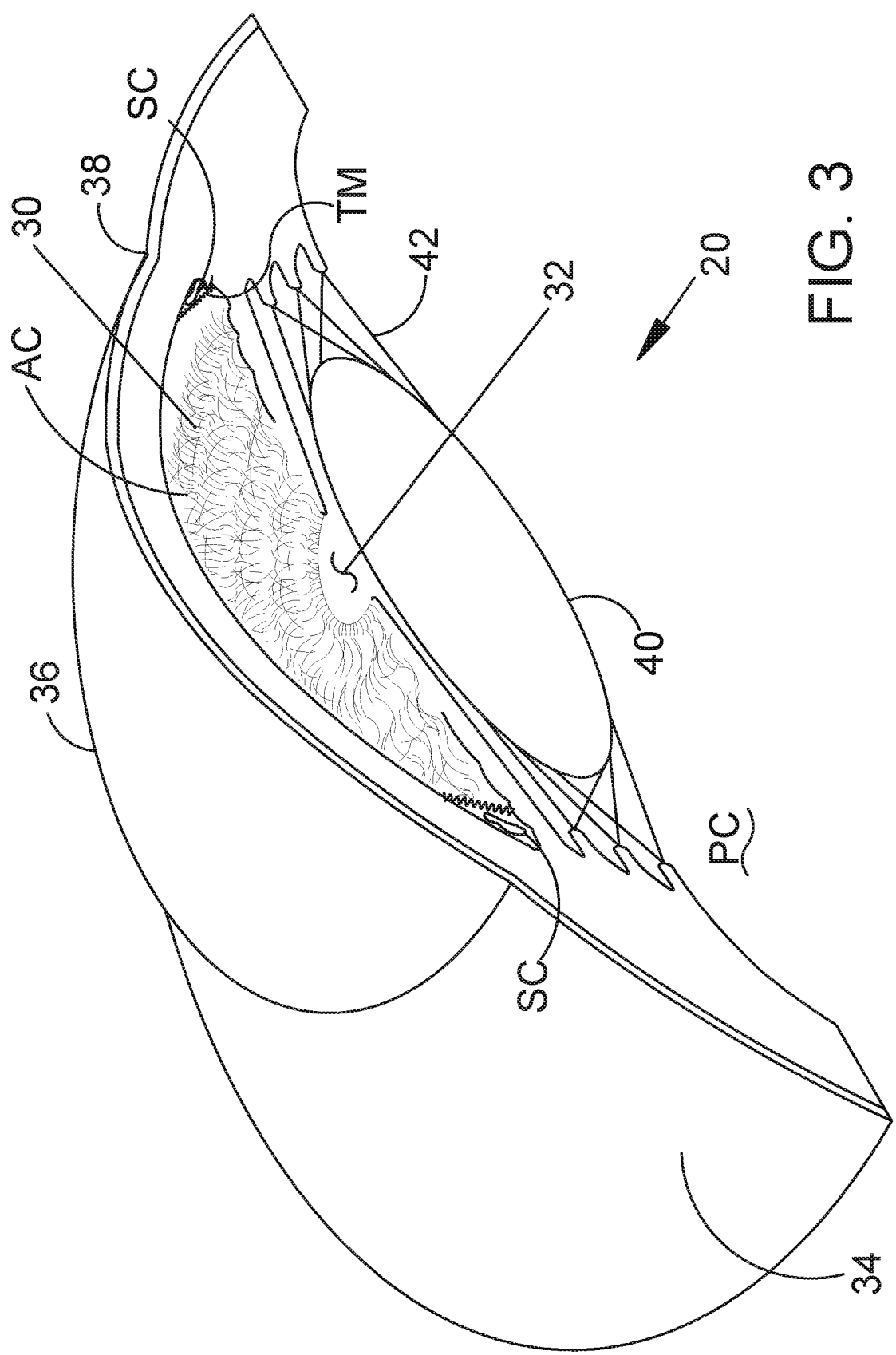
FIG. 3 is a stylized perspective view illustrating the anatomy of an eye.

FIG. 3 is a stylized perspective view illustrating a portion of eye 20 discussed above. Eye 20 includes an iris 30 defining a pupil 32. In FIG. 3, eye 20 is illustrated in a cross-sectional view created by a cutting plane passing through the center of pupil 32. Eye 20 can be conceptualized as a fluid filled ball having two chambers. Sclera 34 of eye 20 surrounds a posterior chamber PC filled with a viscous fluid known as vitreous humor. Cornea 36 of eye 20 encloses an anterior chamber AC that is filled with a fluid known as aqueous humor. The cornea 36 meets the sclera 34 at a limbus 38 of eye 20. A lens 40 of eye 20 is located between anterior chamber AC and posterior chamber PC. Lens 40 is held in place by a number of ciliary zonules 42.

Whenever a person views an object, he or she is viewing that object through the cornea, the aqueous humor, and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the eye as new aqueous humor is secreted by the epithelial cells of the ciliary body. This excess aqueous humor enters the blood stream and is carried away by venous blood leaving the eye.

Schlemm's canal SC is a tube-like structure that encircles iris 30. Two laterally cut ends of Schlemm's canal SC are visible in the cross-sectional view of FIG. 3. In a healthy eye, aqueous humor flows out of anterior chamber AC and into Schlemm's canal SC. Aqueous humor exits Schlemm's canal SC and flows into a number of collector channels. After leaving Schlemm's canal SC, aqueous humor is absorbed into the venous blood stream and carried out of the eye.

Figure 4:
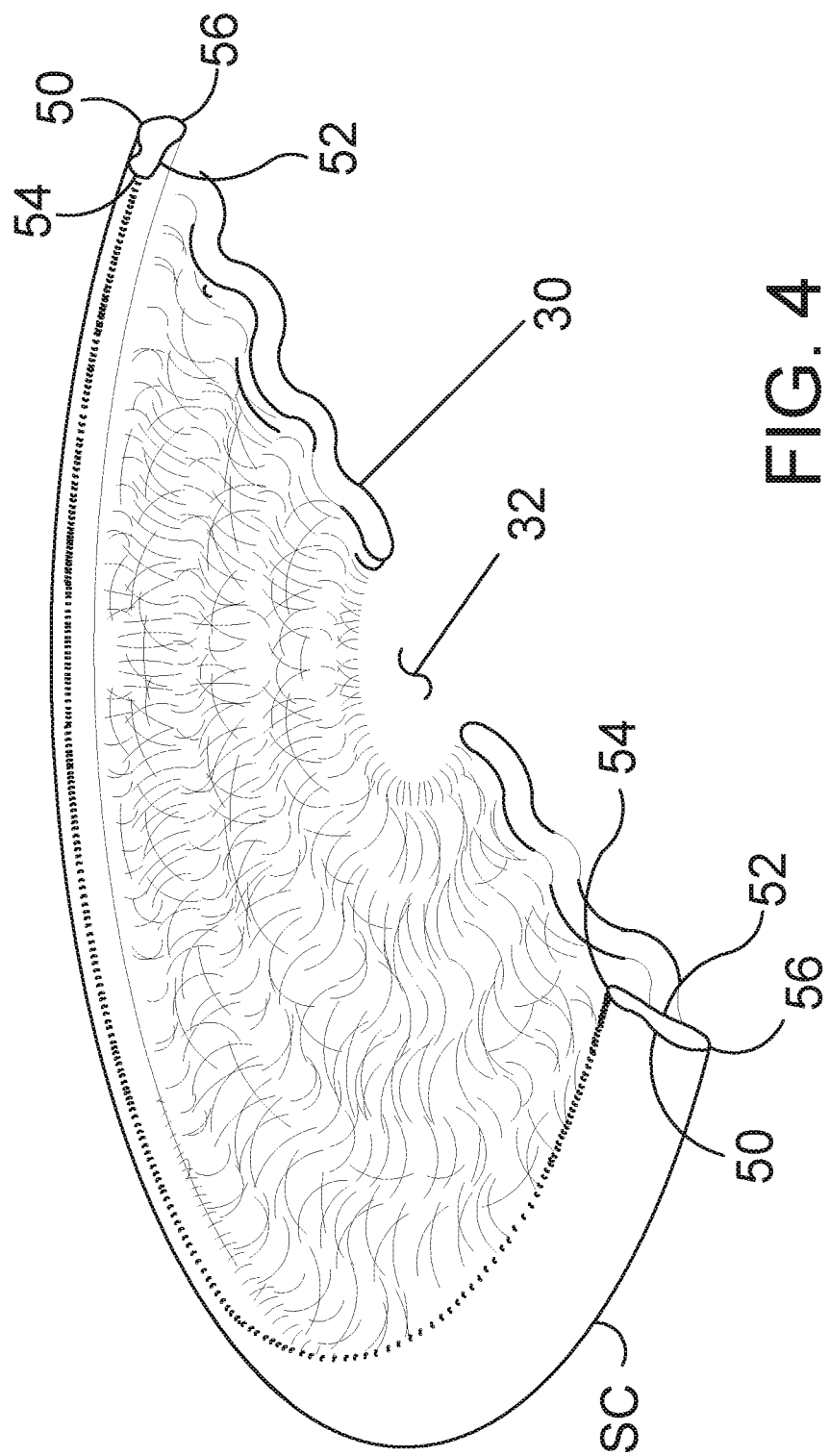
FIG. 4 is a stylized perspective view showing Schlemm's canal and an iris of the eye shown in the previous figure.

FIG. 4 is a stylized perspective view showing Schlemm's canal SC and iris 30 of eye 20 shown in the previous figure. In FIG. 4, Schlemm's canal SC is shown encircling iris 30. With reference to FIG. 4, it will be appreciated that Schlemm's canal SC may overhang iris 30 slightly. Iris 30 defines a pupil 32. In the embodiment of FIG. 4, Schlemm's canal SC and iris 30 are shown in cross-section, with a cutting plane passing through the center of pupil 32.

The shape of Schlemm's canal SC is somewhat irregular, and can vary from patient to patient. The shape of Schlemm's canal SC may be conceptualized as a cylindrical-tube that has been partially flattened. With reference to FIG. 4, it will be appreciated that Schlemm's canal SC has a first major side 50, a second major side 52, a first minor side 54, and a second minor side 56.

Schlemm's canal SC forms a ring around iris 30 with pupil 32 disposed in the center of that ring. With reference to FIG. 4, it will be appreciated that first major side 50 is on the outside of the ring formed by Schlemm's canal SC and second major side 52 is on the inside of the ring formed by Schlemm's canal SC. Accordingly, first major side 50 may be referred to as an outer major side of Schlemm's canal SC and second major side 52 may be referred to as an inner major side of Schlemm's canal SC. With reference to FIG. 4, it will be appreciated that first major side 50 is further from pupil 32 than second major side 52. The outer major wall of Schlemm's canal is supported by scleral tissue of the eye. Elevated pressure inside the eye of a patient suffering from glaucoma may cause the inside major wall of Schlemm's canal to be pressed against the outer major wall of the canal.

FIG. 5 is an enlarged cross-sectional view further illustrating Schlemm's canal SC shown in the previous figure. With reference to FIG. 5, Schlemm's canal SC comprises a wall W defining a lumen 58. The shape of Schlemm's canal SC is somewhat irregular and can vary from patient to patient. The shape of Schlemm's canal SC may be conceptualized as a cylindrical-tube that has been partially flattened. The cross-sectional shape of lumen 58 may be compared to the shape of an ellipse. A major axis 60 and a minor axis 62 of lumen 58 are illustrated with dashed lines in FIG. 5.

The length of major axis 60 and minor axis 62 can vary from patient to patient. The length of minor axis 62 is between one and thirty micrometers in most patients. The length of major axis 60 is between one hundred and fifty micrometers and three hundred and fifty micrometers in most patients.

With reference to FIG. 5, Schlemm's canal SC comprises a first major side 50, a second major side 52, a first minor side 54, and a second minor side 56. In the embodiment of FIG. 5, first major side 50 is longer than both first minor side 54 and second minor side 56. Also in the embodiment of FIG. 5, second major side 52 is longer than both first minor side 54 and second minor side 56.

Figure 6A:
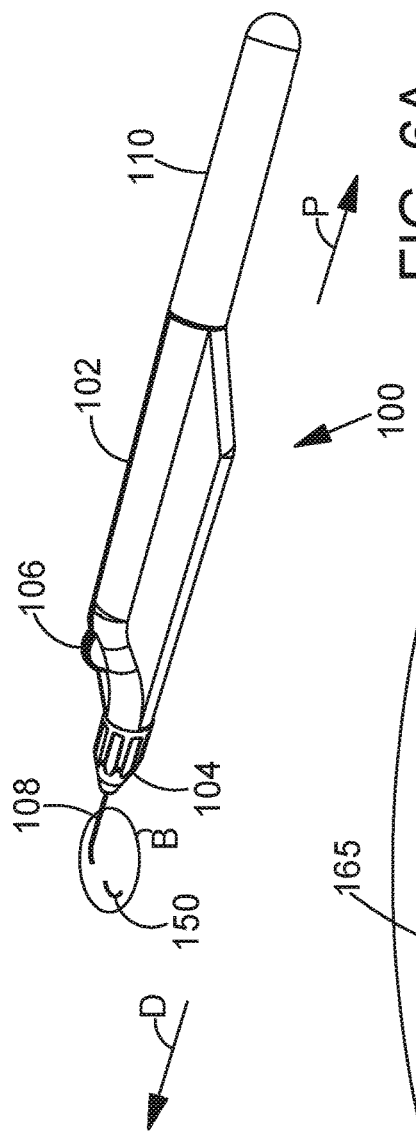
FIG. 6A is a perspective view showing a delivery system including an ocular implant and a cannula defining a passageway that is dimensioned to slidingly receive the ocular implant.
Figure 6B:
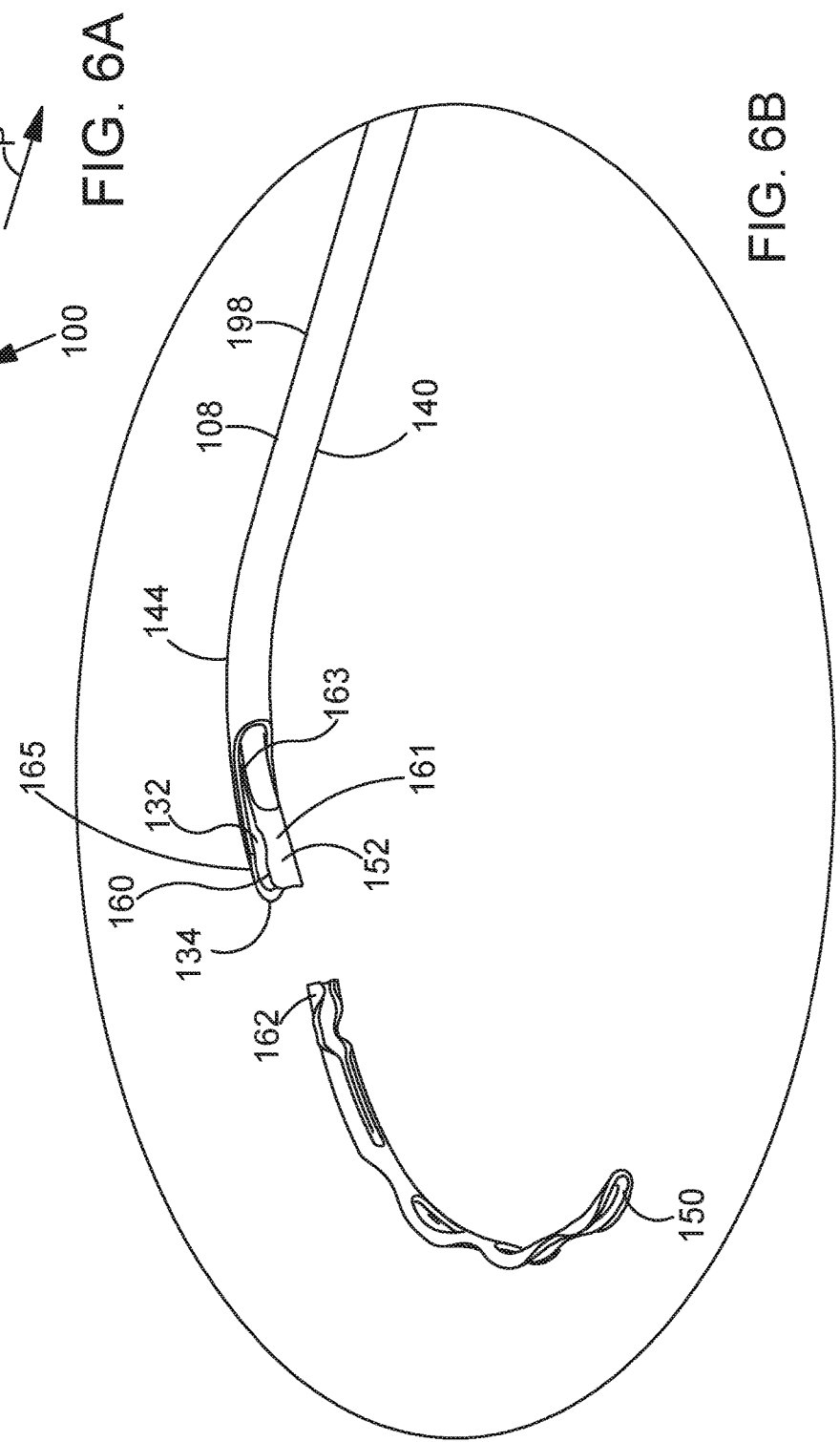
FIG. 6B is an enlarged detail view further illustrating the ocular implant and the cannula 108 shown in FIG. 6A.

FIG. 6A is a perspective view showing a delivery system 100 including an ocular implant 150 and a cannula 108 defining a passageway that is dimensioned to slidingly receive ocular implant 150. Delivery system 100 may be used to advance ocular implant 150 into a target location in the eye of a patient. Examples of target locations that may be suitable in some applications include areas in and around Schlemm's canal, the trabecular meshwork, the suprachoroidal space, and the anterior chamber of the eye. FIG. 6B is an enlarged detail view further illustrating ocular implant 150 and cannula 108 of delivery system 100.

Delivery system 100 of FIG. 6A is capable of controlling the advancement and retraction of ocular implant 150 within cannula 108. Ocular implant 150 may be placed in a target location (e.g., Schlemm's canal) by advancing the ocular implant through a distal opening 132 of cannula 108 while the distal opening is in fluid communication with Schlemm's canal. In the embodiment of FIG. 6A, ocular implant 150 has been advanced through distal opening 132 of cannula 108 for purposes of illustration.

Delivery system 100 of FIG. 6A includes a housing 102, a sleeve 104, and an end cap 110. A tracking wheel 106 extends through a wall of housing 102 in FIG. 6A. Tracking wheel 106 is part of a mechanism that is capable of advancing and retracting a delivery tool 152 of delivery system 100. The delivery tool 152 extends through a distal opening of cannula 108 of FIG. 6B. Rotating the tracking wheel will cause delivery tool 152 to move in an axial direction along a passageway defined by cannula 108. The axial direction may be in a distal direction D or a proximal direction P.

In the embodiment of FIG. 6A, housing 102 is configured to be gripped with one hand while providing control over the axial advancement and retraction of ocular implant via tracking wheel 106. The housing of delivery system 100 results in an advantageous ergonomic relationship of the fingers relative to the hand. This design provides a configuration that will allow a user, such as a physician, to stabilize the device using part of the hand, while leaving the middle or index finger free move independently from the remainder of the hand. The middle or index finger is free to move independently to rotate the wheel for advancing and/or retract the ocular implant.

FIG. 6B is an enlarged detail view further illustrating ocular implant 150 and a cannula 108 of delivery system 100. Cannula 108 comprises a generally tubular member 198 having proximal portion 140, a distal end 134, and a distal portion 144 extending between distal end 134 and proximal portion 140. In the embodiment of FIG. 6, distal portion 144 is curved. In some useful embodiments, distal portion 144 is dimensioned and configured to be received in the anterior chamber of the eye.

FIG. 6B shows delivery tool 152 of delivery system 100 extending through distal opening 132 of cannula 108. Delivery tool 152 includes an interlocking portion 160 that is configured to form a connection with a complementary interlocking portion 162 of ocular implant 150, as explained in more detail below. In the embodiment of FIG. 6, rotating the tracking wheel will cause delivery tool 152 and ocular implant 150 to move along a path defined by cannula 108. Cannula 108 is sized and configured so that the distal end of cannula 108 can be advanced through the trabecular meshwork of the eye and into Schlemm's canal. Positioning cannula 108 in this way places distal opening 132 in fluid communication with Schlemm's canal. Ocular implant 150 may be placed in Schlemm's canal by advancing the ocular implant through distal opening 132 of cannula 108 while the distal opening is in fluid communication with Schlemm's canal. The distal portion of the cannula may include a cutting portion configured to cut through the trabecular meshwork and the wall of Schlemm's canal, such as by providing distal end 134 with a sharp edge adapted to cut through such tissue.

Figure 7:
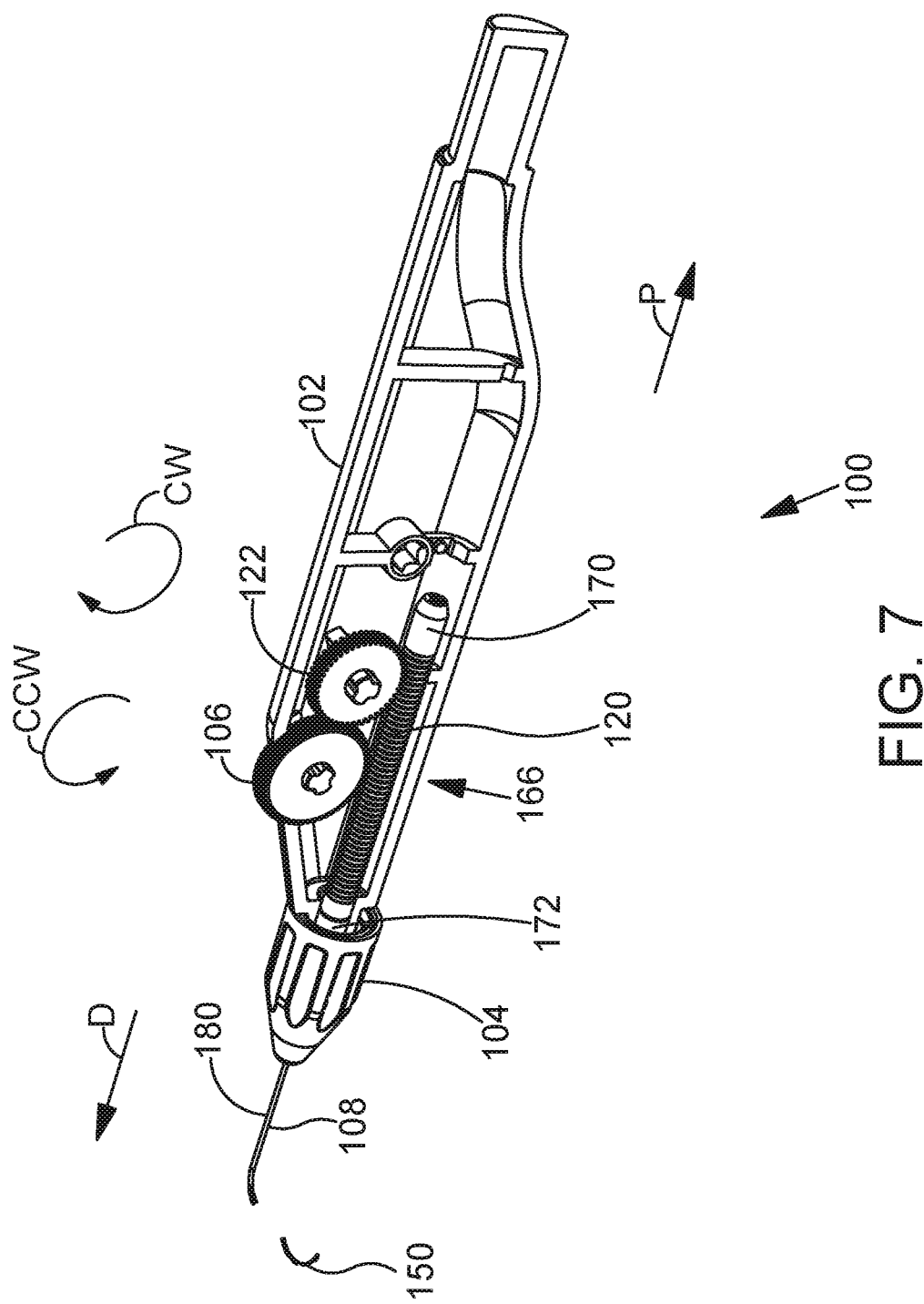
FIG. 7 is a perspective view further illustrating delivery system 100 shown in FIG. 6.

FIG. 7 is a perspective view further illustrating delivery system 100 shown in the previous figure. In FIG. 7, a portion of housing 102 has been removed for purposes of illustration. Delivery system 100 includes a delivery tool subassembly 170 and a cannula subassembly 180. Delivery tool subassembly 170 includes rotating rack gear 120 and a delivery tool (not shown). In the embodiment of FIG. 7, the delivery tool extends into a passageway defined by a cannula 108. Cannula 108 can be seen extending beyond sleeve 104 in FIG. 7. Cannula subassembly 180 includes cannula 108, a hub 172, and an extension tube (not shown). In the embodiment of FIG. 7, the extension tube of cannula subassembly 180 is disposed inside a lumen defined by rotating rack gear 120.

Delivery system 100 includes a mechanism 166 that controls the movement of delivery tool subassembly 170. Mechanism 166 includes a number of components that are located inside housing 102, including tracking wheel 106, an idler gear 122, and the rotating rack gear 120. In the embodiment of FIG. 7, tracking wheel 106 and idler gear 122 are both rotatably supported by housing 102. Gear teeth on tracking wheel 106 engage gear teeth on idler gear 122, which in turn engage gear teeth on the rotating rack gear 120. Rotating tracking wheel 106 in a counter clockwise direction CCW causes idler gear 122 to rotate in a clockwise direction CW, which in turn causes the rotating rack gear 120 to move in a distal direction D. Rotating tracking wheel 106 in a clockwise direction CW causes idler gear 122 to rotate in a counter clockwise direction CCW, which in turn causes the rotating rack gear 120 to move in a proximal direction P. In other embodiments, the idler gear may be eliminated from the device, which would cause counterclockwise movement of the tracking wheel to move the rack gear proximally.

In the embodiment of FIG. 7, a sleeve 104 is fixed to cannula subassembly 180. Sleeve 104 may be rotated by the user to change the orientation of cannula 108 with respect to housing 102. The sleeve 104 may include gripping features, such as grooves (as shown), a rubber coating, or other frictional surfaces to facilitate this use. In some applications, correct alignment between the cannula and iris is advantageous to ensure that the core tube and/or ocular implant is advanced at the correct trajectory relative to Schlemm's canal or other anatomy in the eye into which the ocular implant is to be implanted. The device is configured in a manner that keeps the ocular implant aligned within the device during rotation. Selected groups of components are keyed together to ensure that they rotate as a single body while simultaneously allowing axial movement of the ocular implant. In the embodiment of FIG. 7, cannula subassembly 180 and delivery tool subassembly 170 rotate in unison with sleeve 104 relative to housing 102.

In the embodiment of FIG. 7, rotating rack gear 120 is configured to rotate with sleeve 104 while maintaining the ability to move axially in the distal and proximal directions before, during, and after rotation. As the rotating rack gear 120 moves distally and/or proximally, it causes corresponding movement of the delivery tool relative to cannula 108. This movement is transferred to ocular implant 150 when delivery tool 152 is coupled to ocular implant 150. Delivery tool subassembly 170 and cannula subassembly 180 engage one another in a keyed arrangement, as described in more detail below. This keyed arrangement causes delivery tool subassembly 170 and cannula subassembly 180 to maintain a constant rotational orientation relative to each other while, at the same time, allowing delivery tool subassembly 170 to translate in a distal direction D and a proximal direction P relative to cannula subassembly 180.

Figure 8:
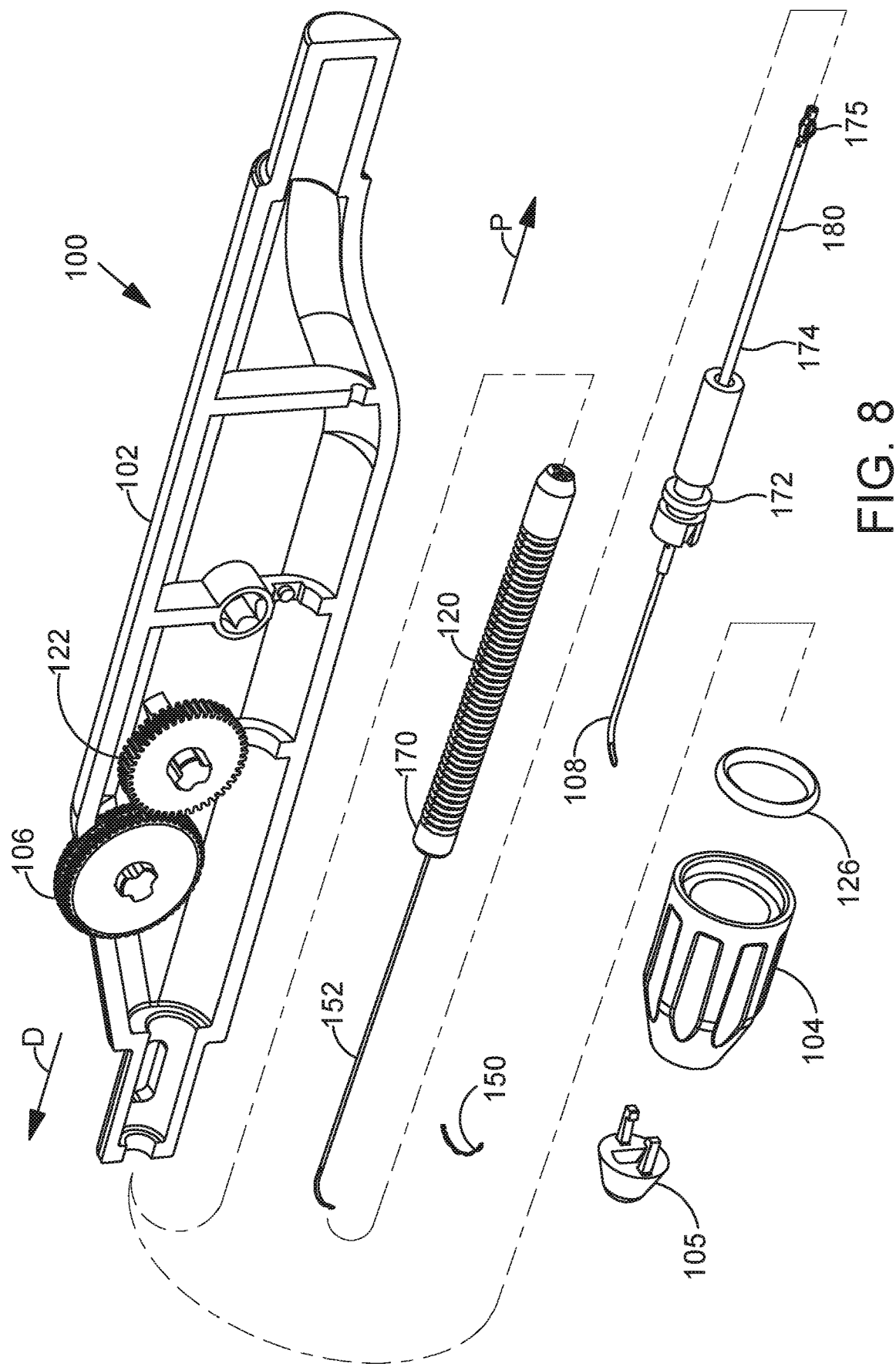
FIG. 8 is an exploded view illustrating various elements of a delivery system in accordance with the detailed description.

FIG. 8 is an exploded view illustrating various elements of delivery system 100. Cannula subassembly 180 includes a hub 172 and an extension tube 174 that are both fixed to cannula 108. Extension tube 174 includes a shaped portion 175 that is dimensioned and shaped to fit within a shaped through hole 177 (shown in FIGS. 8A and 11) within by rotating rack gear 120. This keyed arrangement causes delivery tool subassembly 170 and cannula subassembly 180 to maintain a constant rotational orientation relative to each other while, at the same time, allowing delivery tool subassembly 170 to translate in a distal direction D and a proximal direction P relative to cannula subassembly 180.

In some embodiments, delivery tool 152 is formed from shape memory material (such as, e.g., nitinol), and at least a portion of delivery tool 152 assumes a curved at-rest shape when no external forces are acting on it. Delivery tool 152 can be urged to assume a straightened shape, for example, by inserting delivery tool 152 through a straight portion of the passageway defined by cannula 108. When the delivery tool is confined, such as within cannula 108, the interlocking portion can engage the complementary interlocking portion to join the delivery tool and ocular implant together, and allow the delivery tool and ocular implant to move together through the cannula 108, as described in more detail below.

Delivery system 100 also includes an O-ring 126 disposed between sleeve and 104 and housing 102. O-ring 126 can provide friction and/or resistance between sleeve 104 and housing 102. This friction and/or resistance may be useful, for example, to hold the sleeve 104 in a desired orientation. A noseplug 105 snaps into the distal end of the delivery system.

Figure 9:
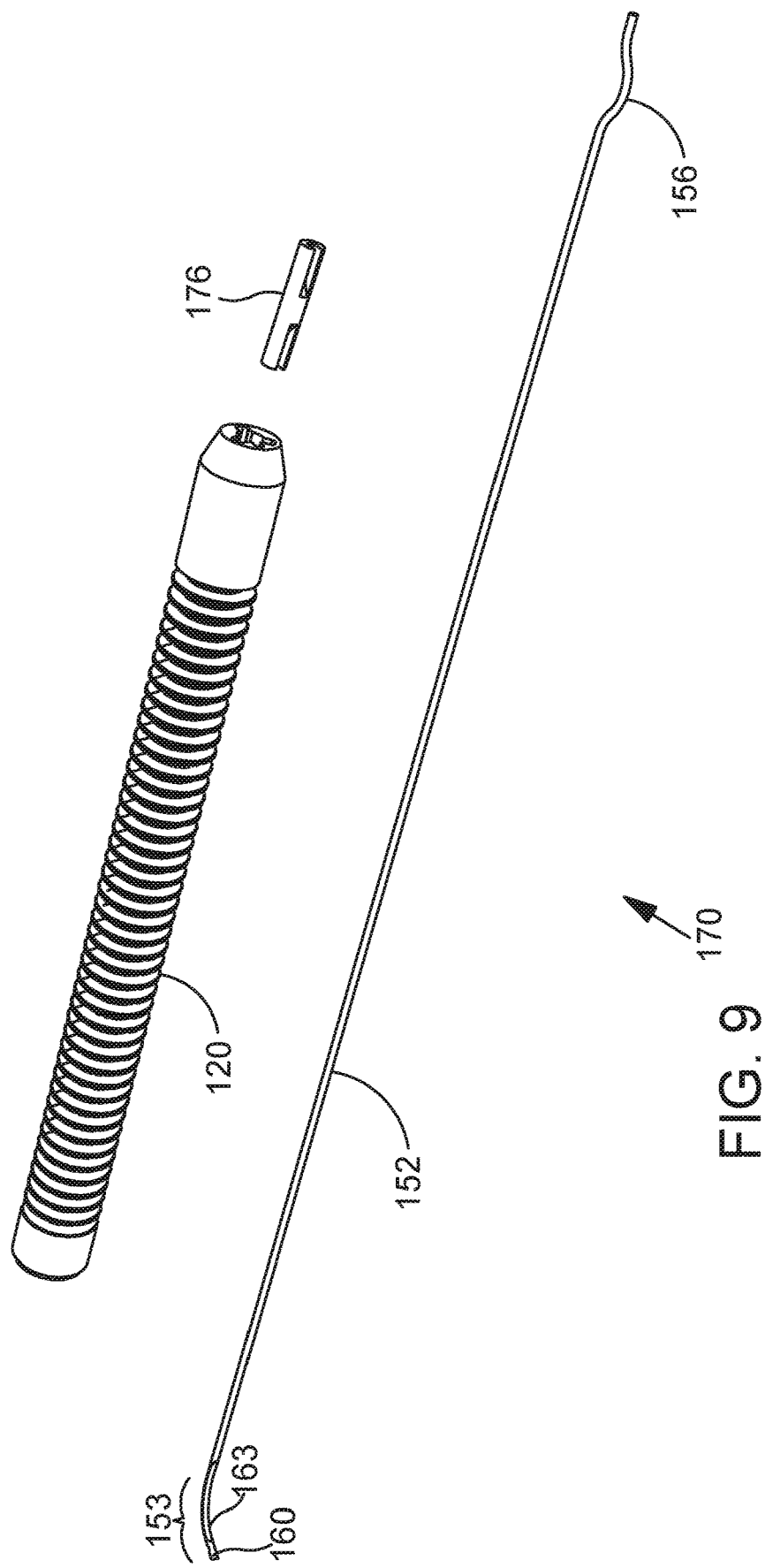
FIG. 9 is an exploded perspective view further illustrating the delivery tool subassembly shown in the exploded perspective view of FIG. 8.
Figure 11:
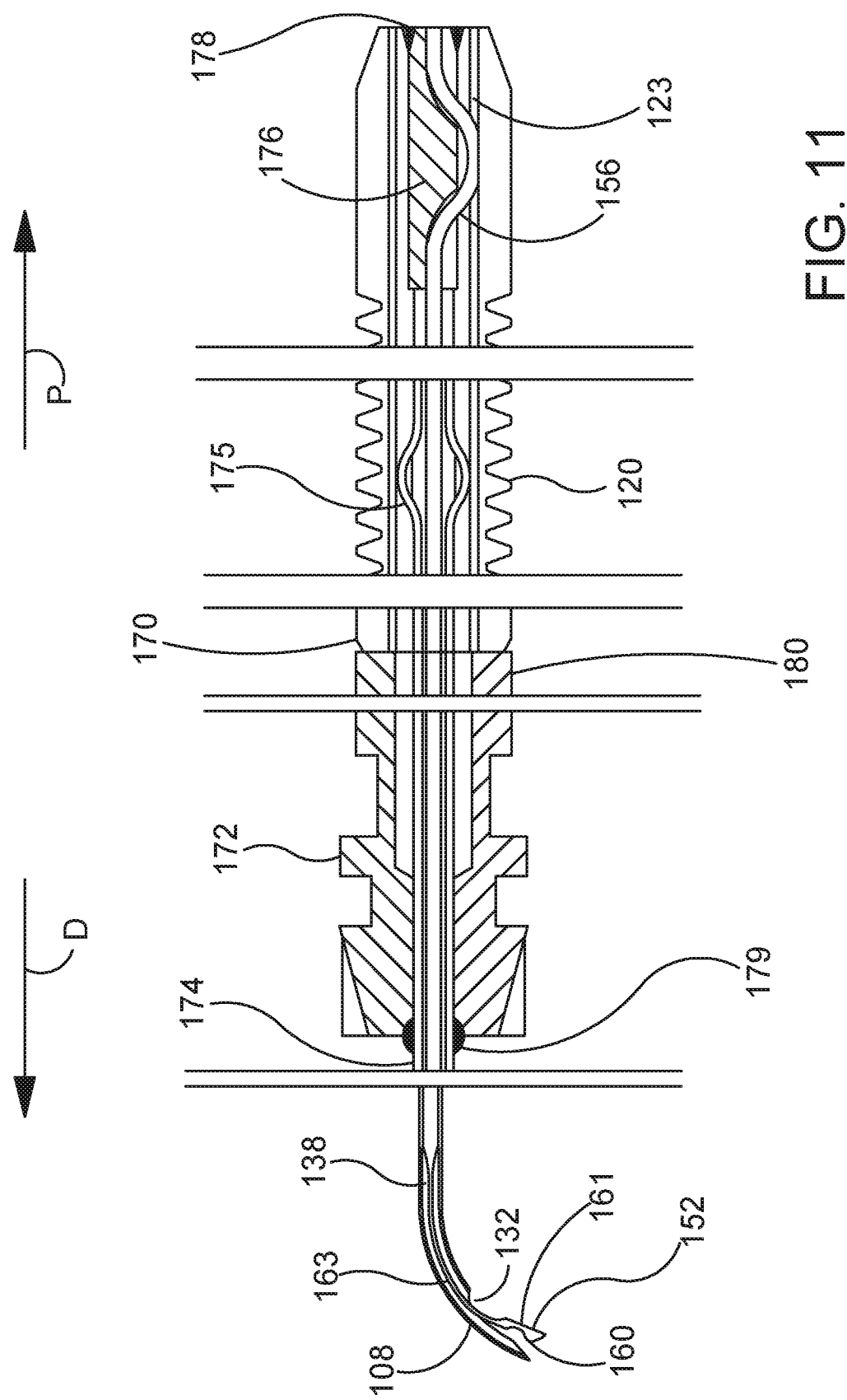
FIG. 11 is a cross-sectional view showing an assembly including both the delivery tool subassembly and the cannula subassembly shown in the exploded perspective view of FIG. 8.

FIG. 9 is an exploded perspective view of delivery tool subassembly 170 shown in the previous figure. Delivery tool subassembly 170 comprises a delivery tool 152, a rotating rack gear 120, and a spacer 176. Delivery tool 152 includes a shaped proximal portion 156, a curved distal portion 153, a distal cannula engagement surface 161 and a reduced diameter portion 163 proximal to the distal cannula engagement surface 161. Spacer 176 is interposed between rotating rack gear 120 and shaped proximal portion 156 of delivery tool 152 to hold delivery tool 152 and rotating rack gear 120 in a generally co-axial arrangement when delivery tool subassembly 170 is in an assembled state, as shown in FIG. 11. Distal cannula engagement surface 161 is adapted to slide along an inside surface of the cannula wall while the delivery tool 152 is engaged to ocular implant 150. Curved distal portion 153 of delivery tool 152 has an at rest curve that is greater (i.e., has a smaller radius of curvature) than the curved portion 144 of cannula 108.

Figure 10:
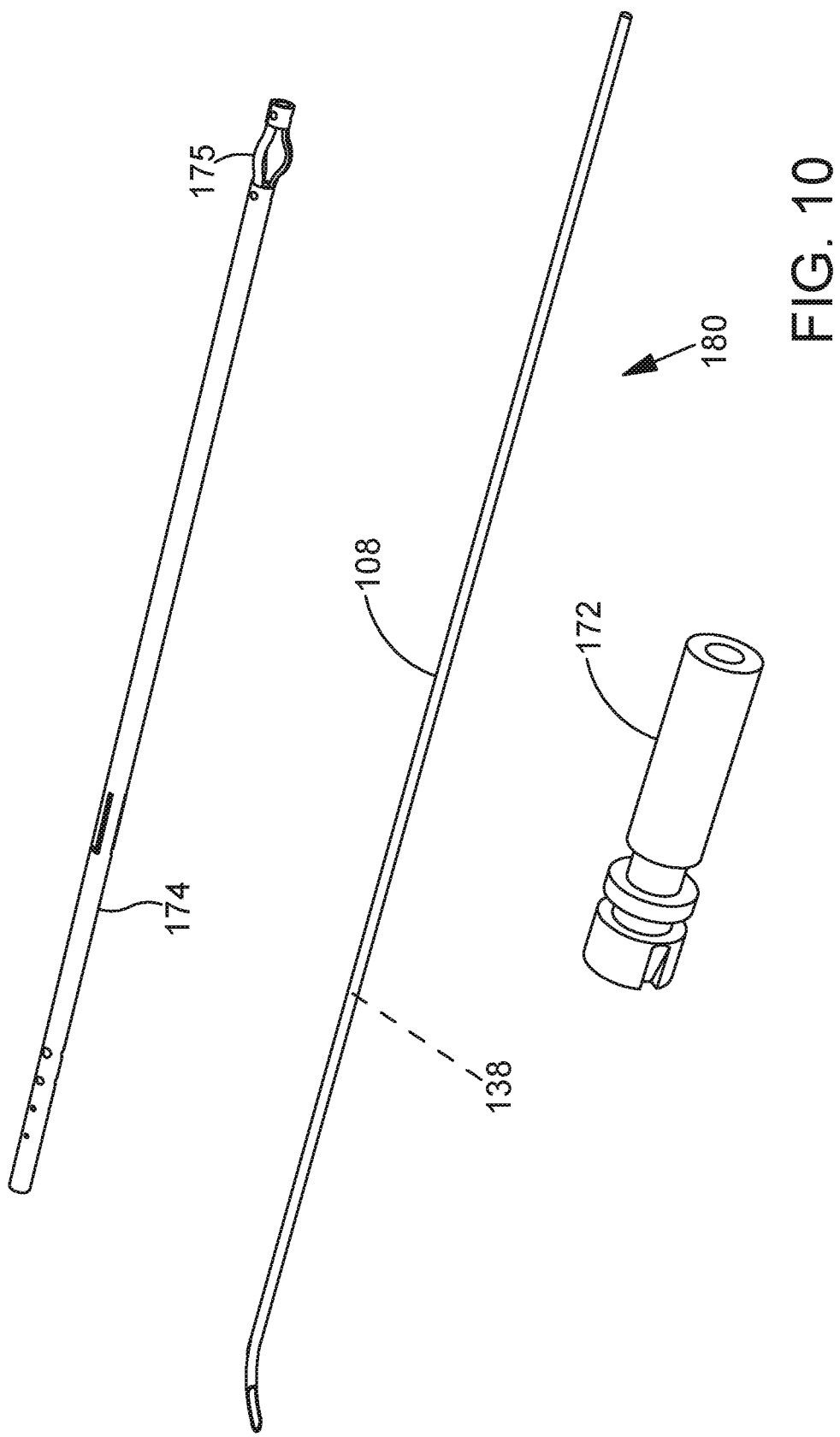
FIG. 10 is an exploded perspective view further illustrating the cannula subassembly shown in the exploded perspective view of FIG. 8.

FIG. 10 is an exploded perspective view of cannula subassembly 180. Cannula subassembly 180 comprises cannula 108, extension tube 174 and hub 172. In the embodiment of FIG. 10, cannula 108 defines a passageway 138 that is dimensioned to slidingly receive an ocular implant and the delivery tool shown in the previous figure. At the same time, extension tube 174 of cannula subassembly 180 may be received inside a lumen defined by the rotating rack gear shown in the previous figure.

Extension tube 174 includes a shaped portion 175 that is dimensioned and shaped to fit within a shaped through hole defined by rotating rack gear 120, as shown below in FIG. 11. This keyed arrangement causes delivery tool subassembly 170 and cannula subassembly 180 to maintain a constant rotational orientation relative to each other while, at the same time, allowing delivery tool subassembly 170 to translate in a distal direction D and a proximal direction P relative to cannula subassembly 180.

FIG. 11 is a cross-sectional view showing an assembly including delivery tool subassembly 170 and cannula subassembly 180 discussed above. Delivery tool subassembly 170 includes a delivery tool 152, a rotating rack gear 120 and a spacer 176. In the cross-sectional view of FIG. 11, a shaped portion 156 of delivery tool 152 can be seen extending into a slot 123 extending from a central portion 181 a through hole 177 formed in rotating rack gear 120. (FIG. 8A shows an end view of rotating rack gear 120 and through hole 177.) In the embodiment of FIG. 11, an interlocking portion 160 of delivery tool 152 is disposed in angular alignment with shaped portion 156. Spacer 176 is interposed between rotating rack gear 120 and delivery tool 152. In the exemplary embodiment of FIG. 11, spacer 176 is shaped and dimensioned to hold delivery tool 152 and rotating rack gear in a generally co-axial arrangement. This arrangement creates an advantageous oriented relationship of interlocking portion 160 with respect to the distal opening 132 of cannula 108 and ensures that interlocking portion 160 is unimpeded and readily disengages itself from the implant when it exits and flexes through distal opening 132. In the exemplary embodiment of FIG. 11, spacer 176 and rotating rack gear 120 are fixed to each other at a weld joint 178. Weld joint 178 may be formed, for example, using a laser welding process.

Cannula subassembly 180 includes cannula 108, a hub 172, and an extension tube 174. Extension tube 174 is disposed about cannula 108. Extension tube 174 and cannula 108 may be fixed to one another, for example, using a laser spot welding process. Hub 172 is fixed to an outer surface portion of extension tube 174 in the embodiment of FIG. 11. In FIG. 11, extension tube 174 of cannula subassembly 180 can be seen extending into a shaped through-hole defined by rotating rack gear 120 of delivery tool assembly 170.

In FIG. 11, delivery tool 152 can be seen extending into a passageway 138 defined by a cannula 108 of cannula subassembly 180. Passageway 138 defined by cannula 108 is sized to slidably enclose delivery tool 152 and an ocular implant that is coupled to delivery tool 152. Delivery tool 152 is configured to form a connection with the ocular implant, so that distal movement of the delivery tool can cause distal movement of the ocular implant within cannula 108. Delivery tool 152 may be used to advance the ocular implant through a distal opening 132 of cannula 108 in order to deliver the ocular implant into the eye. The assembly of FIG. 11 may be rotated by the user to change the orientation of the curved portion of cannula 108 with respect to the housing of the delivery system. The keyed relationship between delivery tool subassembly 170 and cannula subassembly 180 assures that the rotational orientation between cannula 108 and the ocular implant/delivery tool stays constant while at the same time, allowing ocular implant/delivery tool to translate in a distal direction D and a proximal direction P relative to cannula 108.

Figure 12:
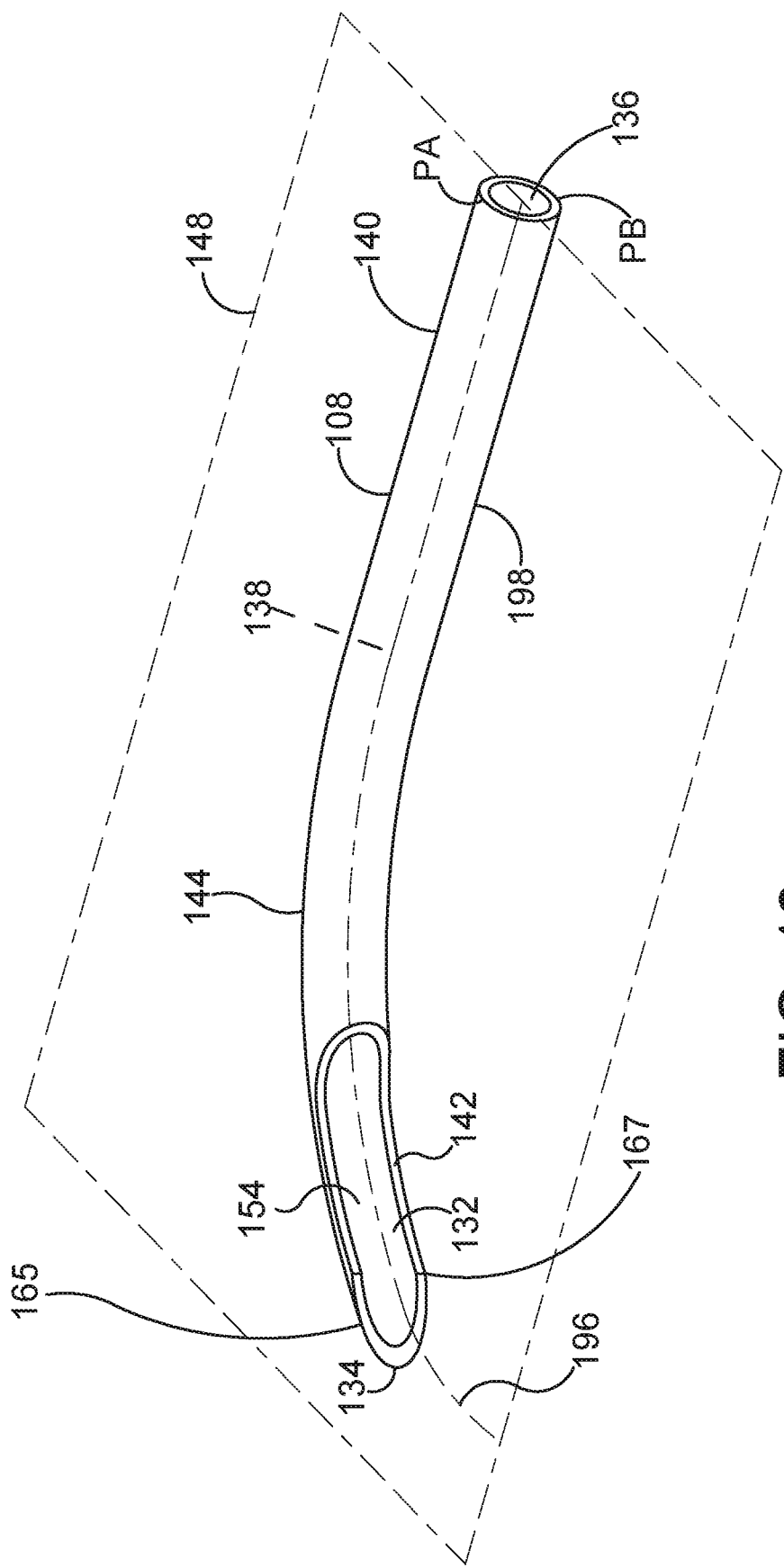
FIG. 12 is a perspective view of a cannula in accordance with the detailed description.

FIG. 12 is a perspective view of a cannula 108 in accordance with the present detailed description. Cannula 108 of FIG. 12 comprises a generally tubular member 198 having a central axis 196. Generally tubular member 198 of FIG. 12 comprises a proximal portion 140, a distal end 134, and a distal portion 144 extending between distal end 134 and proximal portion 140. A distal opening surface 142 surrounds a distal opening 132 extending through the distal end and through a side wall of cannula 108. A beveled edge 165 is disposed at the distal end of distal opening surface 142, extending from the distal end 134 to a proximal extent 167 of beveled edge 165. Tubular member 198 defines distal opening 132, a proximal opening 136, and a passageway 138 extending between proximal opening 136 and distal opening 132.

In the embodiment of FIG. 12, proximal portion 140 of cannula 108 is substantially straight, distal portion 144 of cannula 108 is curved, and central axis 196 defines a curvature plane 148. Curvature plane 148 may be referred to as a plane of curvature. Curvature plane 148 divides cannula 108 into a first portion PA and a second portion PB. In the embodiment of FIG. 12, second portion PB is substantially a mirror image of first portion PA. In FIG. 12, distal portion 144 is shown extending between distal end 134 and proximal portion 140 with no intervening elements. In the embodiment of FIG. 12, distal portion 144 is curved along its entire length.

A method in accordance with this detailed description may include the step of advancing the distal end 134 of cannula 108 through the cornea of a human eye so that distal end 134 is disposed in the anterior chamber of the eye. Cannula 108 may then be used to access Schlemm's canal of the eye, for example, by piercing the wall of Schlemm's canal with the distal end 134 of cannula 108. The beveled edge 165 may be inserted into Schlemm's canal to place at least part of distal opening 132 of cannula 108 in communication with Schlemm's canal, as discussed in more detail below. The ocular implant may be advanced out of a distal port of the cannula and into Schlemm's canal.

In the embodiment of FIG. 12, distal portion 144 of cannula 108 defines a trough 154. In some useful embodiments, trough 154 is configured to receive the entire external cross section of an ocular implant as the ocular implant is being advanced into Schlemm's canal. When this is the case, trough 154 may have a depth dimension that is deeper than a width of the ocular implant. This cannula configuration advantageously prevents the ocular implant from intersecting the layers of the trabecular meshwork as the ocular implant is advanced into Schlemm's canal. Trough 154 may also be configured to allow the proximal portion of the ocular implant to be released from the delivery tool, as discussed below.

Figure 13:
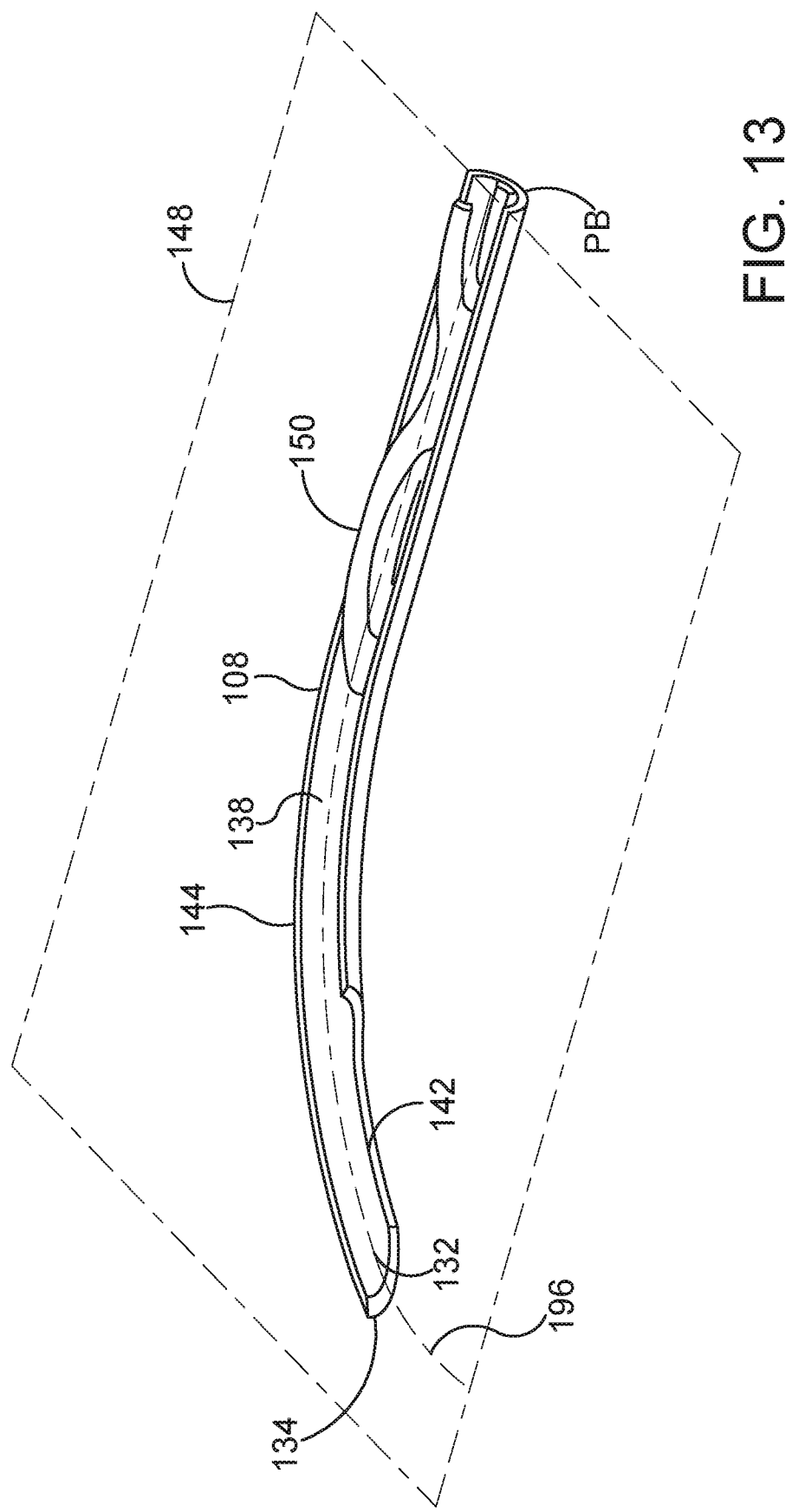
FIG. 13 is a perspective view of an assembly including the cannula shown in FIG. 12 and an ocular implant that is resting in a passageway defined by the cannula.

FIG. 13 is a perspective view of an assembly including cannula 108 shown in the previous figure. For purposes of illustration, cannula 108 is cross-sectionally illustrated in FIG. 13. In FIG. 13, an ocular implant 150 can be seen resting in a passageway 138 defined by cannula 108. With reference to FIG. 13, it will be appreciated that distal portion 144 of cannula 108 is curved so that central axis 196 of cannula 108 defines a curvature plane 148. With reference to FIG. 13, it will be appreciated that curvature plane 148 divides cannula 108 into a first portion and a second portion PB. Only second portion PB of cannula 108 is shown in the illustrative embodiment of FIG. 13.

Figure 14:
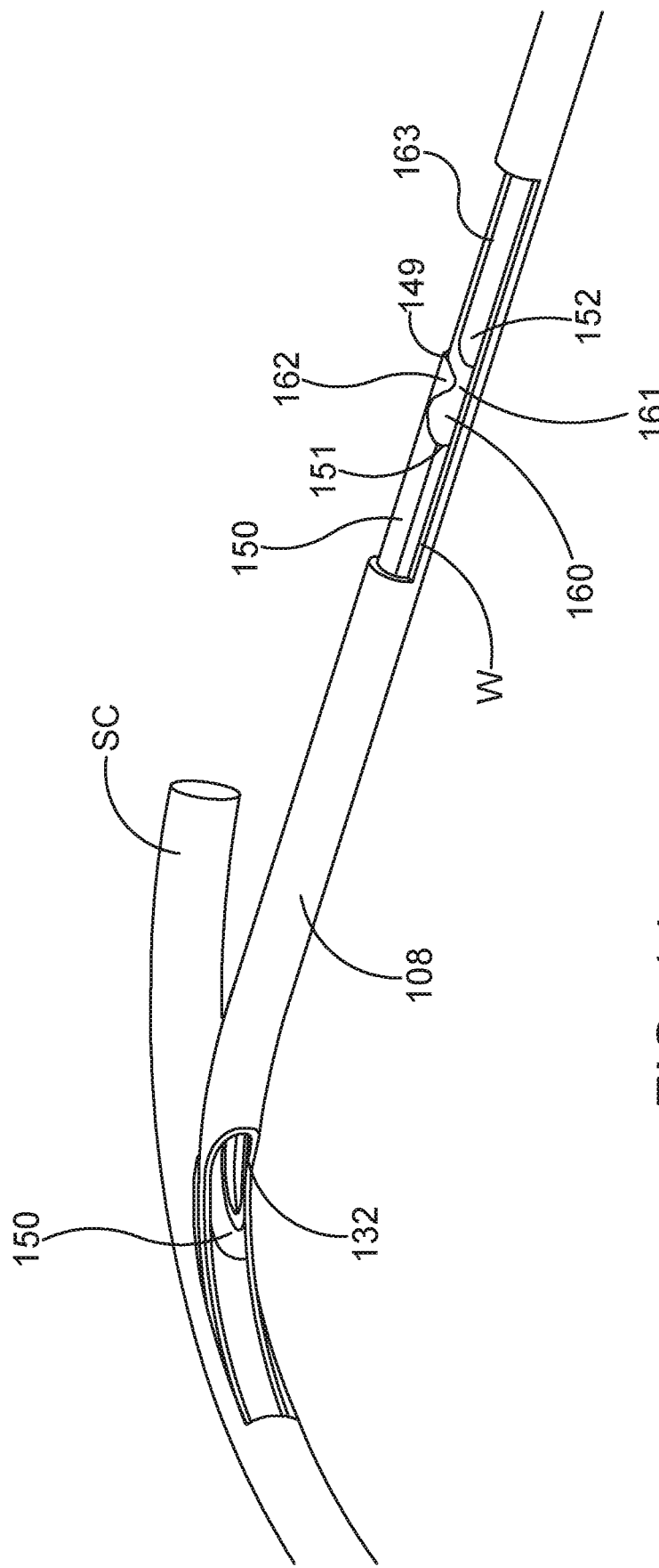
FIG. 14 is a stylized perspective view including the assembly shown in FIG. 13.

FIG. 14 is a stylized perspective view including the assembly shown in the previous figure. In the embodiment of FIG. 14, a distal portion of cannula 108 is shown extending through the wall of Schlemm's canal SC. The distal tip of cannula 108 may include a sharp portion configured for cutting and/or pierced the trabecular meshwork and the wall of Schlemm's canal so that the passageway defined by the cannula can be placed in fluid communication with the lumen defined by Schlemm's canal. With the passageway of the cannula placed in fluid communication with the lumen of Schlemm's canal, ocular implant 150 can be advanced out of the distal opening of the cannula and into Schlemm's canal. In FIG. 14, a distal portion of ocular implant 150 can be seen through distal opening 132 of cannula 108.

For purposes of illustration, a hypothetical window W is cut through the wall of cannula 108 in FIG. 14. An interlocking portion 160 of a delivery tool 152 and a complementary interlocking portion 162 of ocular implant 150 are visible through window W. In the embodiment of FIG. 14, interlocking portion 160 of delivery tool 152 and complementary interlocking portion 162 of ocular implant 150 are engaging each other so that a proximal end 149 of ocular implant 150 is proximal to the distal end 151 of delivery tool 152. Surface 161 of delivery tool 152 rests against the wall of cannula 108 to prevent interlocking portion 160 of delivery tool 152 and complementary interlocking portion 162 of ocular implant 150 from disengaging one another. When they are connected in this fashion, delivery tool 152 and ocular implant 150 move together as the delivery tool is advanced and retracted relative to cannula 108 by the delivery system mechanism.

Figure 15:
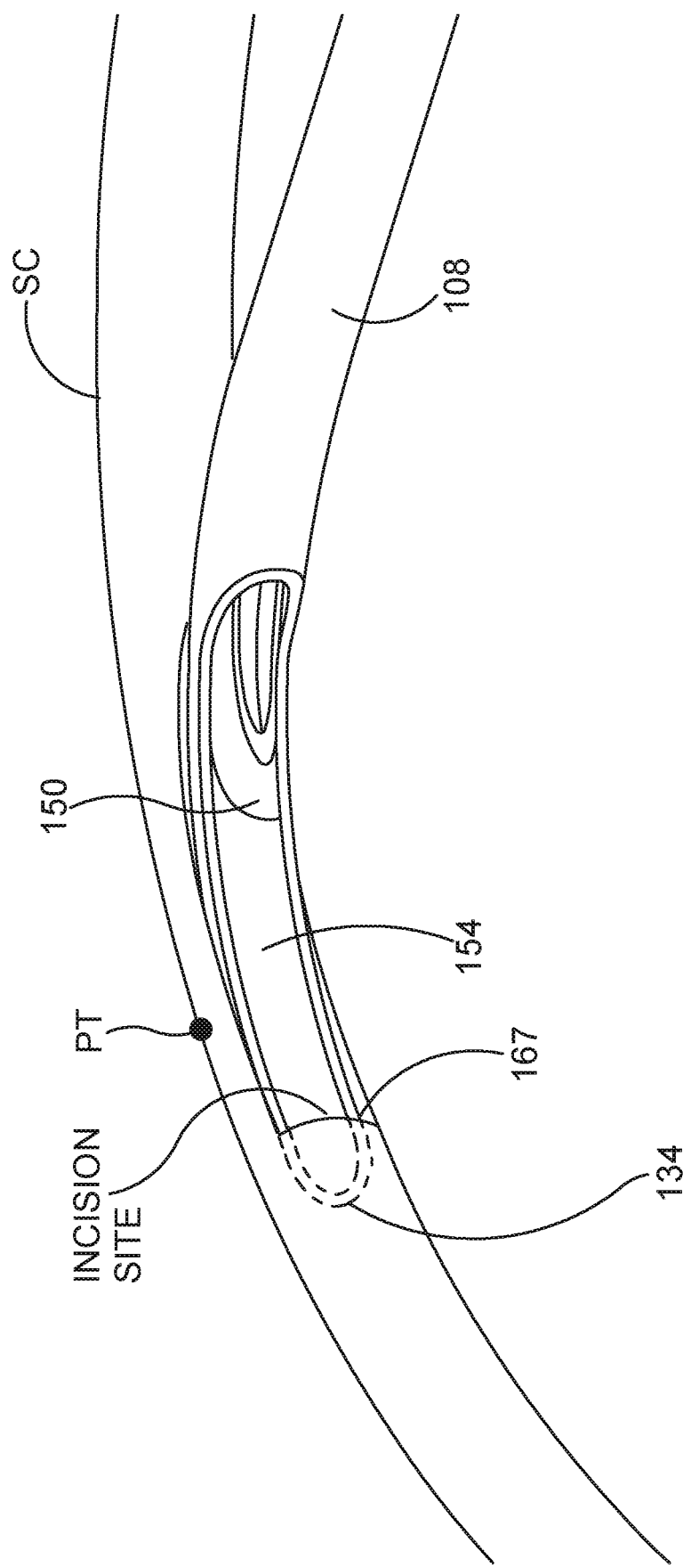
FIG. 15 is an enlarged perspective view showing a portion of the cannula shown in the assembly of FIG. 14.

FIG. 15 is an enlarged perspective view showing a portion of cannula 108 shown in the previous figure. In some useful embodiments, cannula 108 is curved to achieve substantially tangential entry into Schlemm's canal SC. In the embodiment of FIG. 15, cannula 108 is contacting an outer major wall of Schlemm's canal SC at a point of tangency PT. Also in the embodiment of FIG. 15, a curved distal portion of cannula 108 is dimensioned to be disposed within the anterior chamber of the eye.

As shown in FIG. 15, the distal tip 134 and beveled edge of the cannula 108 have been inserted into Schlemm's canal up to the proximal extent 167 of beveled edge 165. In this position, ocular implant 150 can be seen extending into trough 154. In some useful embodiments, the ocular implant has a radius of curvature that is larger than the radius of curvature of the cannula. This arrangement ensures that the ocular implant will track along trough 154 as the ocular implant is urged in a distal direction by delivery system 100.

Figure 16:
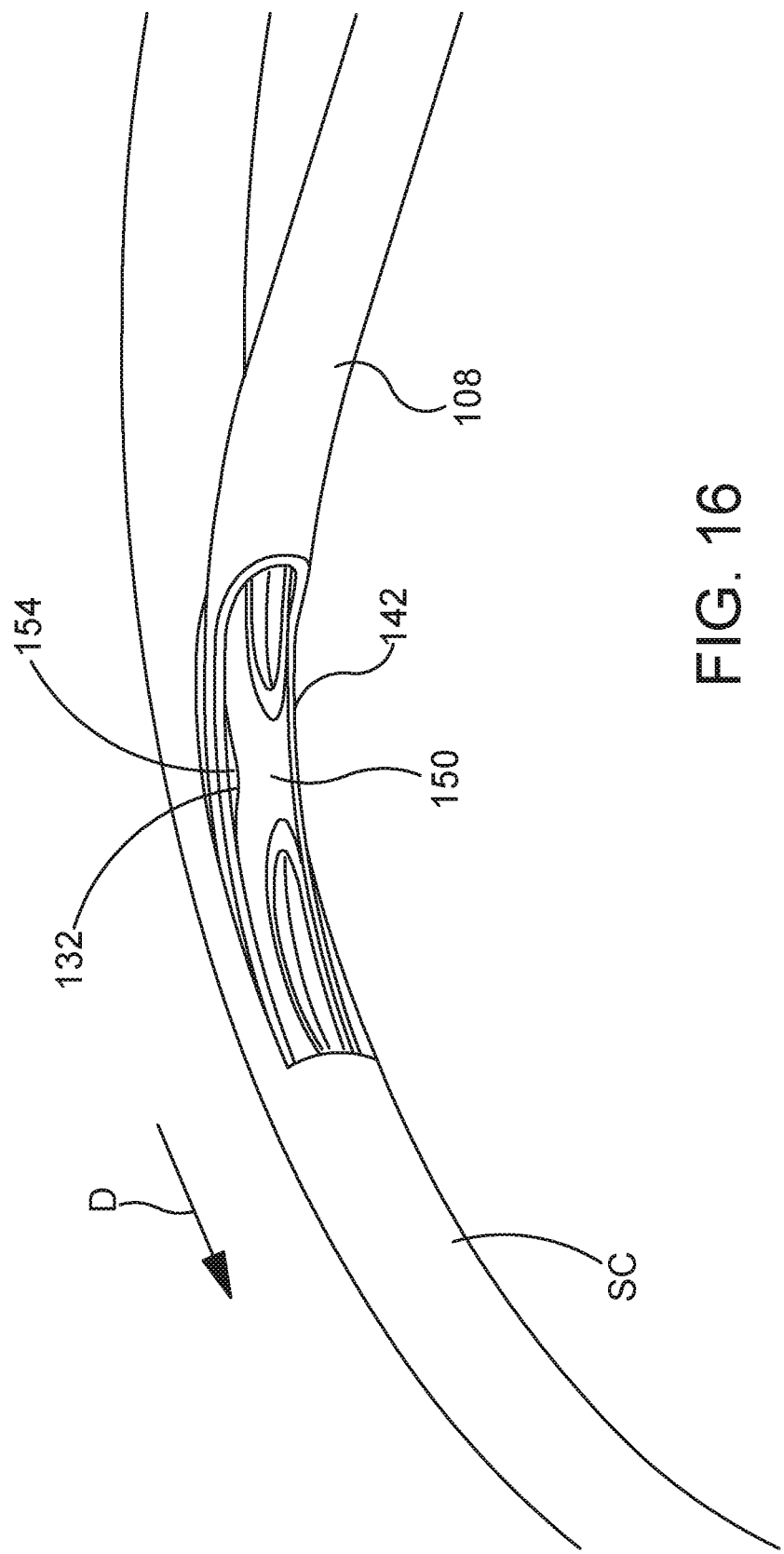
FIG. 16 is an additional perspective view showing the ocular implant and the cannula shown in the previous Figure.

FIG. 16 is an additional perspective view showing ocular implant 150 and cannula 108 shown in the previous figure. By comparing FIG. 16 with the previous figure, it will be appreciated that ocular implant 150 has been advanced in a distal direction D while cannula 108 has remained stationary so that a distal portion of ocular implant 150 is disposed inside Schlemm's canal SC. Trough 154 opens into an elongate opening 132 defined by edge 142 at the distal portion of cannula 108. In the embodiment of FIG. 16, the elongate opening defined by the cannula provides direct visualization of the ocular implant as it is advanced into Schlemm's canal. A configuration allowing direct visualization of the ocular implant has a number of clinical advantages. During a medical procedure, it is often difficult to monitor the progress of the implant by viewing the implant through the trabecular meshwork. For example, blood reflux may push blood into Schlemm's canal obstructing a physician's view the portion of the implant that has entered Schlemm's canal. With reference to FIG. 16, ocular implant 150 tracks along trough 154 as it is advanced distally along cannula 108. The trough opening allows the physician to monitor the progress of the implant by viewing the implant structures as they advance through the trough prior to entering Schlemm's canal. The trough opening also allows the physician to identify the position of the proximal end of the ocular implant with respect to the incision made by the cannula to access Schlemm's canal.

Figure 17:
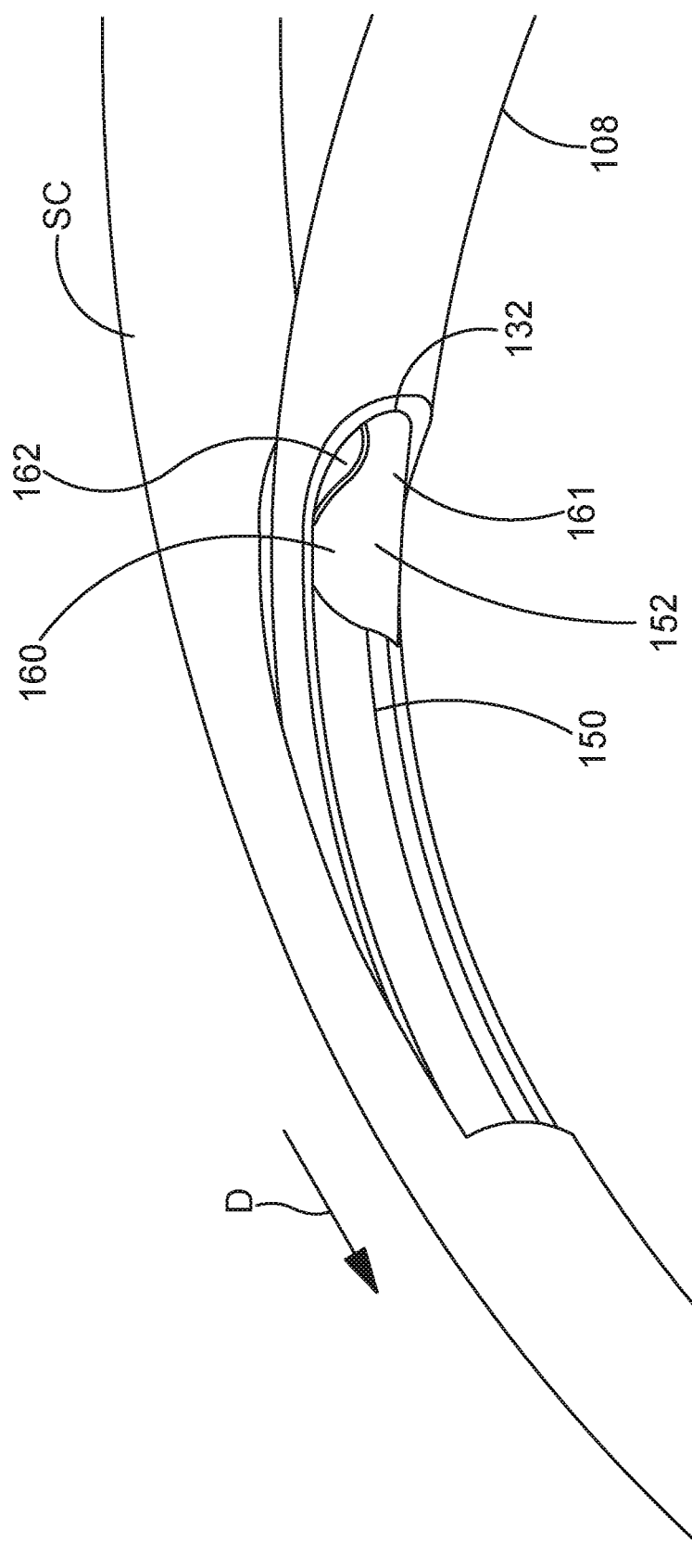
FIG. 17 is an additional perspective view showing the ocular implant and the cannula shown in FIG. 16.

FIG. 17 is an additional stylized perspective view showing ocular implant 150 and cannula 108. In the embodiment of FIG. 17, the interlocking portions 160 and 162 of the delivery tool 152 and ocular implant 150, respectively, can be seen entering the distal opening 132 defined by cannula 108. As shown, ocular implant 150 has been advanced in a distal direction D (relative to the embodiment shown in the previous figure) so that more of ocular implant 150 is disposed inside Schlemm's canal SC. Surface 161 opposite interlocking portion 160 of delivery tool 152 still rests against the inner wall of cannula 108 to keep the delivery tool interlocked with ocular implant 150.

Figure 18:
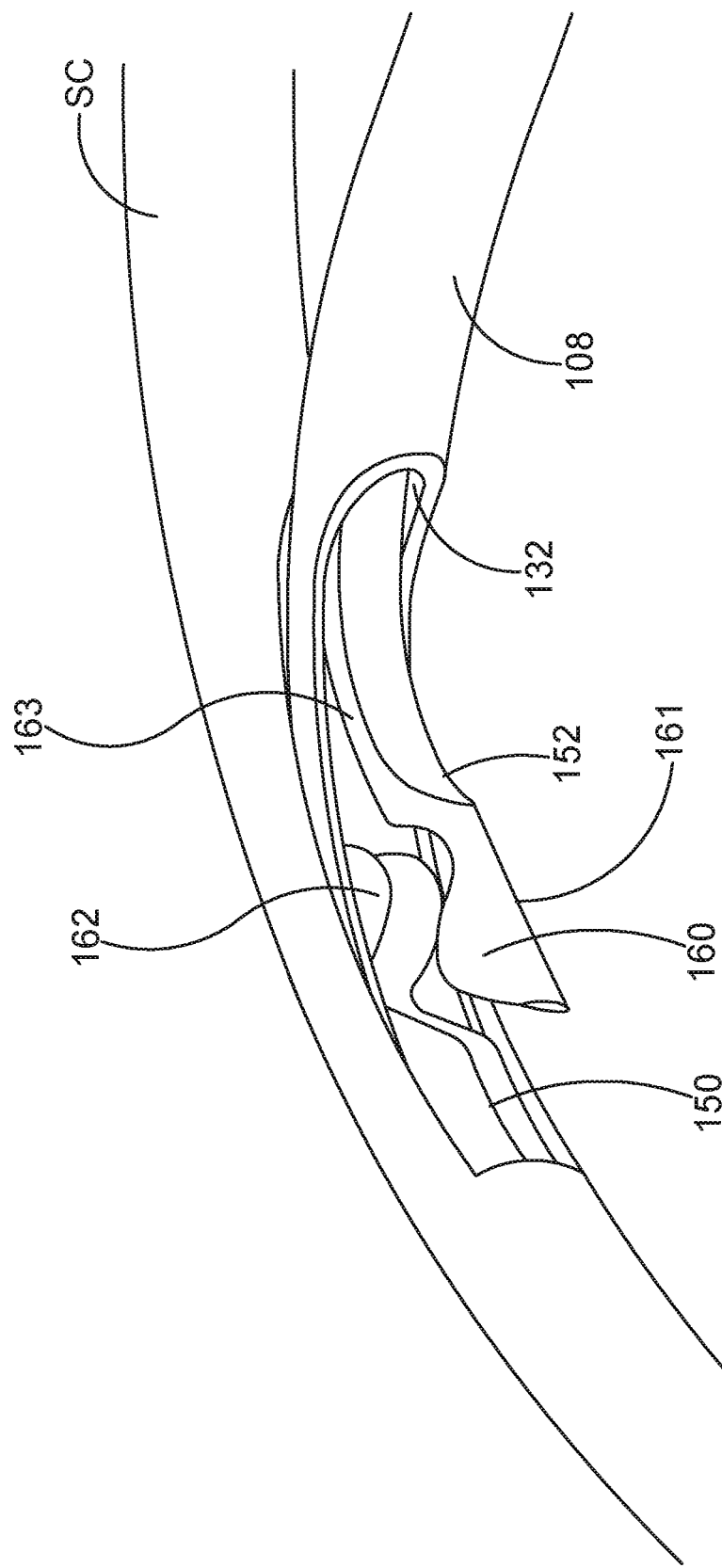
FIG. 18 is an additional perspective view showing the ocular implant and the cannula shown in FIGS. 16 and 17.

FIG. 18 is an additional stylized perspective view showing ocular implant 150 and cannula 108. As shown in FIG. 18, the ocular implant 150 and delivery tool 152 have advanced further distally so that delivery tool surface 161 and part of the reduced diameter portion 163 have now passed into opening 132, thereby permitting the delivery tool curved portion 153 to move toward its curved at-rest shape so that the delivery tool engagement surface 160 disengages and moves away from its complementary engagement surface 162 on the ocular implant 150.

In some useful embodiments, the delivery tool may be colored to provide visual differentiation from the implant. After the disengaging from the ocular implant, cannula 108 and delivery tool 152 can be withdrawn from Schlemm's canal SC leaving the ocular implant 150 in the fully deployed position shown in FIG. 18. After delivery of ocular implant 150 is complete, the delivery tool and the cannula may be removed from the eye, leaving at least a distal portion of the ocular implant in Schlemm's canal.

Figure 19:
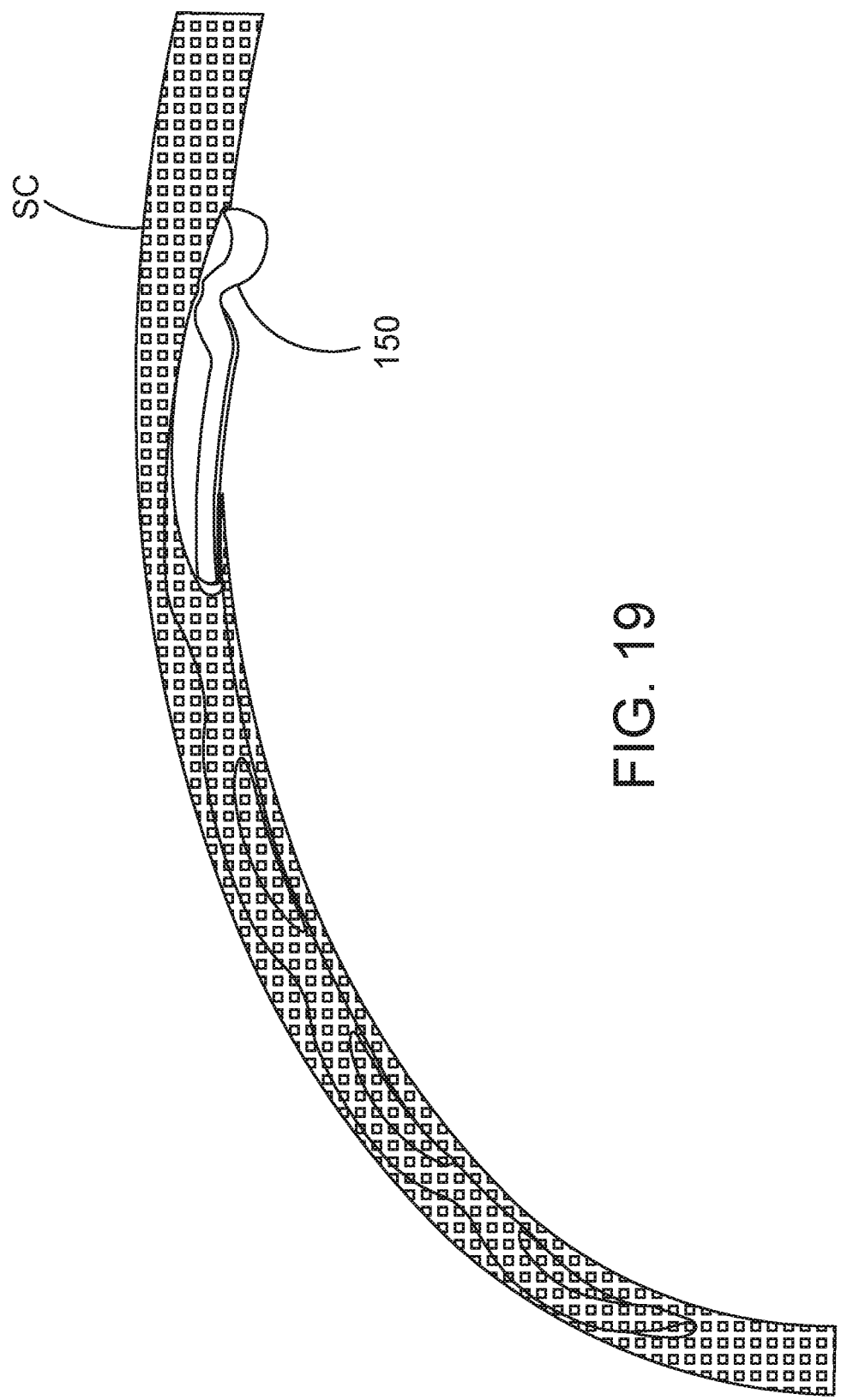
FIG. 19 is a perspective view of Schlemm's canal after the cannula shown in FIG. 18 has been withdrawn leaving an inlet portion of the ocular implant in the anterior chamber of the eye and the remainder of ocular implant in Schlemm's canal.

FIG. 19 is a perspective view of Schlemm's canal SC after the cannula (seen in the previous figure) has been withdrawn leaving an inlet portion of ocular implant 150 in the anterior chamber of the eye and the remainder of ocular implant 150 in Schlemm's canal. The presence of ocular implant 150 in Schlemm's canal may facilitate the flow of aqueous humor out of the anterior chamber. This flow may include axial flow along Schlemm's canal, flow from the anterior chamber into Schlemm's canal, and flow leaving Schlemm's canal via outlets communicating with Schlemm's canal. When in place within the eye, ocular implant 150 will support the trabecular meshwork and Schlemm's canal tissue and will provide for improved communication between the anterior chamber and Schlemm's canal (via the trabecular meshwork) and between pockets or compartments along Schlemm's canal.

FIG. 20A-FIG. 20H are a series of stylized plan views illustrating example methods in accordance with this detailed description and associated apparatus used while performing those methods. In FIG. 20A, a distal portion of cannula 108 is shown extending through the wall of Schlemm's canal SC. In the embodiment of FIG. 20A, cannula 108 includes a sharp portion at its distal end 134 configured for cutting and/or pierced the trabecular meshwork and the wall of Schlemm's canal SC. In the embodiment of FIG. 20A, the distal end of cannula 108 has been advanced through the trabecular meshwork and the wall of Schlemm's canal SC and a passageway defined by cannula 108 has been placed in fluid communication with the lumen defined by Schlemm's canal SC.

FIG. 20B is an additional stylized plan view showing cannula 108 shown in the previous figure. In the embodiment of FIG. 20B, an ocular implant 150 has been advanced out of a distal opening of cannula 108 and into Schlemm's canal SC. In FIG. 20B, a distal portion of ocular implant 150 is shown residing in a lumen defined by Schlemm's canal.

FIG. 20C is an additional stylized plan view showing ocular implant 150 and cannula 108. In the embodiment of FIG. 20C, an interlocking portion 160 of delivery tool 152 and complementary interlocking portion 162 of ocular implant 150 are both disposed near a trough portion of cannula 108. Ocular implant 150 has been advanced in a distal direction D (relative to the embodiment shown in the previous figure) so that more of ocular implant 150 is disposed inside Schlemm's canal SC. In FIG. 20C, ocular implant is shown residing in a fully deployed position. As shown in FIG. 20C, interlocking portion 160 of delivery tool 152 has disengaged from complementary interlocking portion 162 of ocular implant 150.

In the embodiment of FIG. 20C, distal opening 132 defined by cannula 108 is shaped and dimensioned so as to allow interlocking portion 160 of delivery tool 152 to extend therethrough when ocular implant 150 reaches the fully deployed position shown in FIG. 20C. When surface 161 has entered opening 132, a distal portion of delivery tool 152 is free to flex radially inward toward a curved, at-rest shape extending through distal opening 132 when ocular implant 150 reaches the fully deployed position shown in FIG. 20C to disengage from the ocular implant.

FIG. 20D is a plan view of Schlemm's canal SC after cannula 108 has been moved away from ocular implant 150. After moving cannula 108 away from ocular implant 150, a physician may visually inspect the present location of the ocular implant to determine whether that location is acceptable. If the physician determines that the present location is unacceptable, the physician may use the systems and methods described herein to recapture and reposition the ocular implant. The figures described below illustrate exemplary methods and apparatus for recapturing and repositioning the ocular implant.

In the embodiment of FIG. 20E, cannula 108 has been positioned so that the complementary interlocking portion 162 of ocular implant 150 is disposed between cannula 108 and the interlocking portion 160 of delivery tool 152. Further distal movement of cannula 108 will cause delivery tool surface 161 to re-engage with the inner wall of cannula 108, thereby moving the interlocking portion 160 of the delivery tool into re-engagement with the ocular implant. The delivery tool and ocular implant can thereafter be moved proximally, possibly together with the cannula, to reposition the implant for subsequent redeployment.

FIG. 20F is an additional stylized plan view showing ocular implant 150 and cannula 108 shown in the previous figure. By comparing FIG. 20F with the previous figure, it will be appreciated that delivery tool 152 and ocular implant 150 have been moved in a proximal direction P so that a portion of ocular implant 150 has been withdrawn from Schlemm's canal SC. In the embodiment of FIG. 20F, the complementary interlocking portion of ocular implant 150 and the interlocking portion of delivery tool 152 have both been drawn into the passageway defined by cannula 108. Also in the embodiment of FIG. 20F, the side wall of cannula 108 is holding the distal portion of delivery tool 152 in a deformed shape with the interlocking portion of delivery tool 152 engaging the complementary interlocking portion of ocular implant 150.

FIG. 20G is an additional stylized plan view showing ocular implant 150 and cannula 108 shown in the previous figure. In the embodiment of FIG. 20G, ocular implant 150 has been advanced out of a distal opening of cannula 108 and into Schlemm's canal SC. In FIG. 20G, a distal part of ocular implant 150 is shown residing in a lumen defined by Schlemm's canal. In the embodiment of FIG. 20G, interlocking portion 160 of delivery tool 152 and complementary interlocking portion 162 of ocular implant 150 are both once again located near a trough portion of cannula 108. In FIG. 20G, ocular implant is shown residing in a second fully deployed position. In the embodiment of FIG. 20G, the delivery tool 152 has once again disengaged from ocular implant 150 by permitting interlocking portion 160 of delivery tool 152 to move away from complementary interlocking portion 162 of ocular implant 150.

FIG. 20H is a stylized plan view showing ocular implant 150 and Schlemm's canal SC after the cannula (seen in the previous figure) has been withdrawn leaving an inlet portion of ocular implant 150 in the anterior chamber of the eye and the remainder of ocular implant 150 in Schlemm's canal. When in place within the eye, ocular implant 150 will support the trabecular meshwork and Schlemm's canal tissue and will provide for improved communication between the anterior chamber and Schlemm's canal (via the trabecular meshwork) and between pockets or compartments along Schlemm's canal. Accordingly, the presence of ocular implant 150 in Schlemm's canal will facilitate the flow of aqueous humor out of the anterior chamber.

With reference to the figures described above, it will be appreciated that methods in accordance with the present detailed description may be used to position at least a distal portion of an implant in Schlemm's canal of an eye. In some cases, a proximal inlet portion of the ocular implant may be left in the anterior chamber. An exemplary method in accordance with the present detailed description may include the step of advancing a distal end of a cannula through a cornea of the eye so that a distal portion of the cannula is disposed in the anterior chamber of the eye. The cannula may be used to access Schlemm's canal, for example, by cutting and/or piercing the wall of Schlemm's canal with a distal portion of the cannula. A distal opening of the cannula may be placed in fluid communication with Schlemm's canal. The distal end of the ocular implant may be advanced through the distal opening of the cannula and into Schlemm's canal.

After delivering an ocular implant into Schlemm's canal, a physician may visually inspect the present location of the ocular implant to determine whether that location is acceptable. If the physician determines that the present location is unacceptable, the physician may use the systems and methods described herein to recapture and redeliver the ocular implant. Recapturing and redelivering the ocular implant may include the steps of forming a second connection between the delivery tool and the ocular implant and moving the delivery tool and the ocular implant in a proximal direction so that at least a portion of the ocular implant is withdrawn from Schlemm's canal. A distal part of the ocular implant may be advanced into Schlemm's canal while the ocular implant is coupled to the delivery tool at the second connection. The second connection may be selectively broken to release the ocular implant from the delivery system while the distal part of the ocular implant is disposed in Schlemm's canal.

FIG. 21 is a perspective view showing a delivery tool subassembly 370 that may be part of a delivery system (e.g., delivery system 100 shown in FIG. 8). Delivery tool subassembly 370 of FIG. 21 comprises a rotating rack gear 320 that is fixed to a delivery tool 352. Delivery tool 352 includes an interlocking portion 360 and a curved distal portion 353. Curved distal portion 353 of delivery tool 352 is biased to assume the curved at-rest shape shown in FIG. 21 when no external forces are acting on it. Curved distal portion 353 of delivery tool 352 may be urged to assume a straightened shape, for example, when it is disposed in a straight portion of a passageway defined by a cannula. Optional cut-outs 351 may be formed in the wall of delivery tool 352 to reduce friction during tool advancement by reducing the bending force. The cannula wall may also hold interlocking portion 360 of delivery tool 352 into engagement with a complementary interlocking portion of an ocular implant to form a mechanically interlocking connection.

FIG. 22A is a stylized plan view showing delivery tool 352 shown in the previous figure. In the embodiment of FIG. 22A, delivery tool 352 is extending into a passageway 338 defined by a cannula 308. A distal portion of cannula 308 defines a trough 354 that communicates with the passageway 338 defined by the wall of cannula 308. Trough 354 opens out the distal end of cannula 308. Trough 354 also opens into an elongate opening 332 defined by the edge 342 of the cannula wall.

In FIG. 22A, cannula 308 is illustrated in partial cross section. Interlocking portion 360 of delivery tool 352 and a complementary interlocking portion 362 of an ocular implant 350 are visible in FIG. 22A. In the embodiment of FIG. 22A, interlocking portion 360 of delivery tool 352 and complementary interlocking portion 362 of ocular implant 350 are engaging each other to form a mechanically interlocking connection such that the implant's interlocking portion 362 is proximal to the delivery tool's interlocking portion 360. The delivery tool 352 and ocular implant 350 may be selectively disengaged when interlocking portion 360 of delivery tool 352 is allowed to move away from and disengage complementary interlocking portion 362 of ocular implant 350. In the embodiment of FIG. 22, the wall of cannula 308 is preventing interlocking portion 360 of delivery tool 352 from moving away from and disengaging complementary interlocking portion 362 of ocular implant 350. A surface 363 of delivery tool 352 can be seen contacting the wall of cannula 308 at a point S in FIG. 22.

In FIG. 22A, interlocking portion 360 of delivery tool 352 is shown disposed within cannula passageway 338 at a location proximal of trough 354 and distal opening 332. In some useful embodiments, opening 332 is dimensioned and positioned such that, when the ocular implant reaches a predefined location along the passageway, the distal portion of delivery tool 352 will be free to move toward a curved at-rest shape. When the delivery tool assumes a curved shape, the interlocking portion of the delivery tool moves away from and disengages the complementary interlocking portion of the ocular implant. In this way, delivery tool 352 and ocular implant 350 may be selectively disengaged as delivery tool 352 is moved distally along the passageway defined by the cannula from a starting location proximal of opening 332.

FIG. 22B is an additional stylized plan view illustrating cannula 308, ocular implant 350, and delivery tool 352 shown in the previous figure. By comparing FIG. 22B with FIG. 22A, it will be appreciated that delivery tool 352 has been advanced in a distal direction D so that delivery tool 352 is extending through opening 332 and ocular implant 350 is outside of cannula passageway 338. In the embodiment of FIG. 22B, interlocking portion 360 has moved away from complementary interlocking portion 362 and ocular implant 350 and delivery tool 352 have disengaged.

Figure 23:
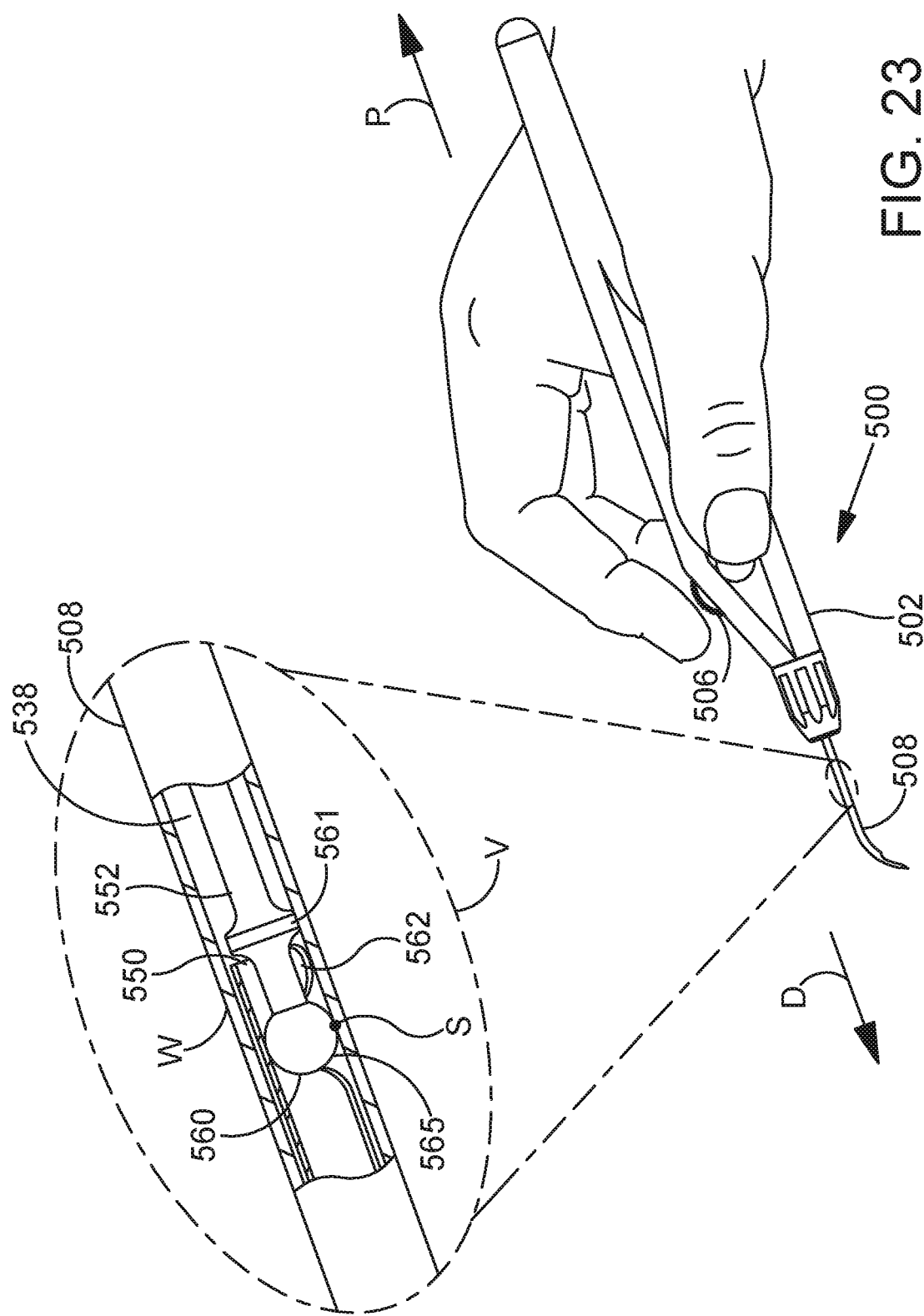
FIG. 23 is a stylized plan view showing a delivery system including an ocular implant disposed in a passageway defined by a cannula.

FIG. 23 is a stylized plan view showing a delivery system 500 including an ocular implant 550 disposed in a passageway 538 defined by a cannula 508. FIG. 23 includes an enlarged detail view V illustrating a portion of cannula 508. For purposes of illustration, a hypothetical window W is cut through the wall of cannula 508 in FIG. 23. An interlocking portion 560 of a delivery tool 552 and a complementary interlocking portion 562 of ocular implant 550 are visible through window W. In the embodiment of FIG. 23, interlocking portion 560 of delivery tool 552 and complementary interlocking portion 562 of ocular implant 550 are engaging each other to form a mechanically interlocking connection. When delivery tool 552 is confined, such as within cannula passageway 538, it can be held in mechanically interlocking engagement with ocular implant 550 so that these elements move together through passageway 538 of cannula 508. An optional ring 561 proximal to interlocking portion 560 and to the proximal end of implant 550 maintains the spacing between interlocking portion 560 and interlocking portion 562 so that they can be more easily disengaged. The wall of cannula 508 prevents interlocking portion 560 of delivery tool 552 and complementary interlocking portion 562 of ocular implant 550 from disengaging one another in the embodiment of FIG. 23. A surface 565 of delivery tool 552 can be seen contacting the wall of cannula 508 at a point S in FIG. 23.

Delivery system 500 of FIG. 23 may be used to advance ocular implant 550 into a target location in the eye of a patient. Delivery system 500 includes a housing 502 and a tracking wheel 506 that can be seen extending through the wall of housing 502 in FIG. 23. Tracking wheel 506 is part of a mechanism that is capable of advancing and retracting delivery tool 552 of delivery system 500. Rotating tracking wheel 506 will cause delivery tool 552 to move in an axial direction along a passageway 538 defined by cannula 508. The axial direction may be in a distal direction D or a proximal direction P. Ocular implant 550 moves along with delivery tool 552 as it is advanced and retracted relative to cannula 508 by the delivery system mechanism.

In the embodiment of FIG. 23, housing 502 is configured to be gripped with one hand while providing control over the axial advancement and retraction of the ocular implant via tracking wheel 506. The design of housing 502 results in an advantageous ergonomic relationship of the fingers relative to the hand. This design provides a configuration that will allow a user, such as a physician, to stabilize the device using part of the hand, while leaving the middle or index finger free move independently from the remainder of the hand. The middle or index finger is free to move independently to rotate tracking wheel 506 of delivery system 500 for advancing and/or retracting delivery tool 552.

Figure 24A:
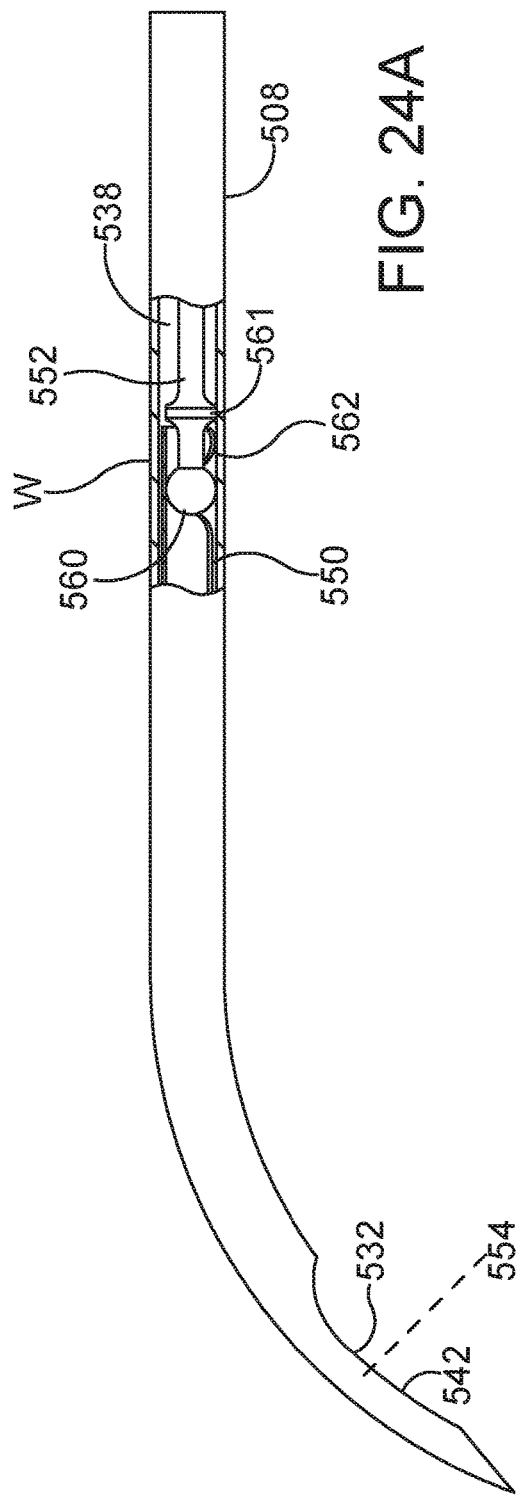
FIG. 24A is a stylized plan view further illustrating the cannula shown in FIG. 23.

FIG. 24A is a stylized plan view further illustrating cannula 508 shown in the previous figure. A distal portion of cannula 508 defines a trough 554 that communicates with a passageway 538 defined by the wall of cannula 508. Trough 554 opens out the distal end of cannula 508. Trough 554 also opens into an elongate opening 532 defined by the edge 542 of the cannula wall. An ocular implant 550 and a portion of a delivery tool 552 are disposed within cannula passageway 538. A distal portion of delivery tool 552 is biased to assume a curved at-rest shape when no external forces are acting on it. In the embodiment of FIG. 24A, the distal portion of delivery tool 552 is disposed in a straight portion of the cannula passageway 538 so that it is urged to assume a straightened shape.

Figure 24B:
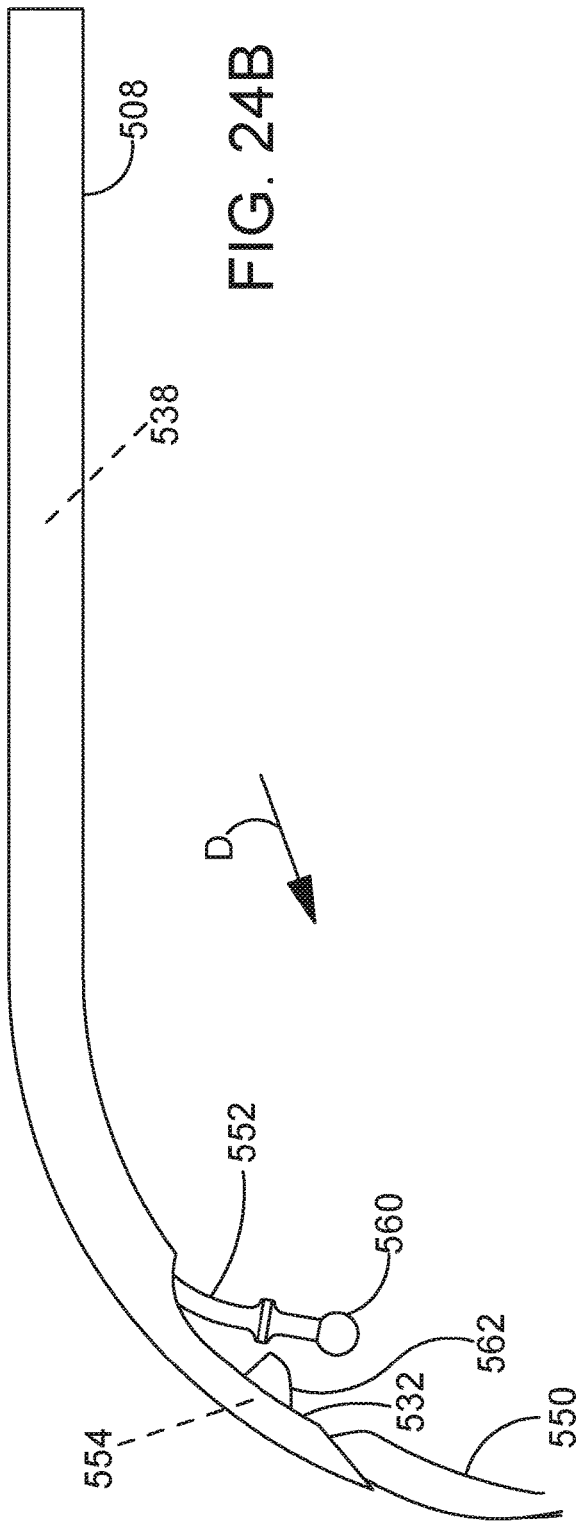
FIG. 24B is an additional stylized plan view illustrating the cannula, ocular implant, and delivery tool shown in FIG. 24A.

FIG. 24B is an additional stylized plan view illustrating cannula 508, ocular implant 550, and delivery tool 552 shown in the previous figure. In FIG. 24B, delivery tool 552 is shown extending through opening 532 and ocular implant 550 is shown in a location outside of cannula passageway 538. In FIG. 24B, a gap can be seen between interlocking portion 560 of delivery tool 552 and a complementary interlocking portion 562 of ocular implant 550 in FIG. 24B. Accordingly, it will be appreciated that ocular implant 550 and delivery tool 552 have disengaged. In the embodiment of FIG. 24B, the distal portion of delivery tool 552 has flexed through distal opening 532 as it has assumed a curved shape.

Reference is now made to both FIG. 24A and FIG. 24B which may be collectively referred to as FIG. 24. In the embodiment of FIG. 24A, the distal end of delivery tool 552 is disposed within cannula passageway 538 at a location proximal of trough 554 and distal opening 532. In the embodiment of FIG. 24B, delivery tool 552 has been advanced in a distal direction D so that delivery tool 552 is extending through opening 532. Opening 532 is dimensioned and positioned such that, when the ocular implant reaches a predefined location along the passageway, the distal portion of delivery tool 552 will be free to move toward a curved at-rest shape. When the delivery tool assumes a curved shape, the interlocking portion of the delivery tool moves away from and disengages the complementary interlocking portion of the ocular implant. In this way, delivery tool 552 and ocular implant 550 may be selectively disengaged as delivery tool 552 is moved distally along passageway 538 from the position shown in FIG. 24A to the position shown in FIG. 24B.

FIG. 25A is a perspective view showing a delivery tool subassembly 770 that may be part of a delivery system (e.g., delivery system 100 shown in FIG. 8). Delivery tool subassembly 770 of FIG. 25A comprises a rotating rack gear 720 that is fixed to a delivery tool 752 formed as a flat ribbon. FIG. 25B is enlarged perspective view showing a distal portion of delivery tool 752. FIG. 25A and FIG. 25B may be collectively referred to as FIG. 25. Delivery tool 752 of FIG. 25 includes an interlocking portion 760 and a curved distal portion 753. Curved distal portion 753 of delivery tool 752 is biased to assume the curved at-rest shape shown in FIG. 25 when no external forces are acting on it. Curved distal portion 753 of delivery tool 752 may be urged to assume a straightened shape, for example, when it is disposed in a straight portion of a passageway defined by a cannula. The cannula wall may also hold interlocking portion 760 of delivery tool 752 into engagement with a complementary interlocking portion of an ocular implant to form a mechanically interlocking connection.

Figure 26A:
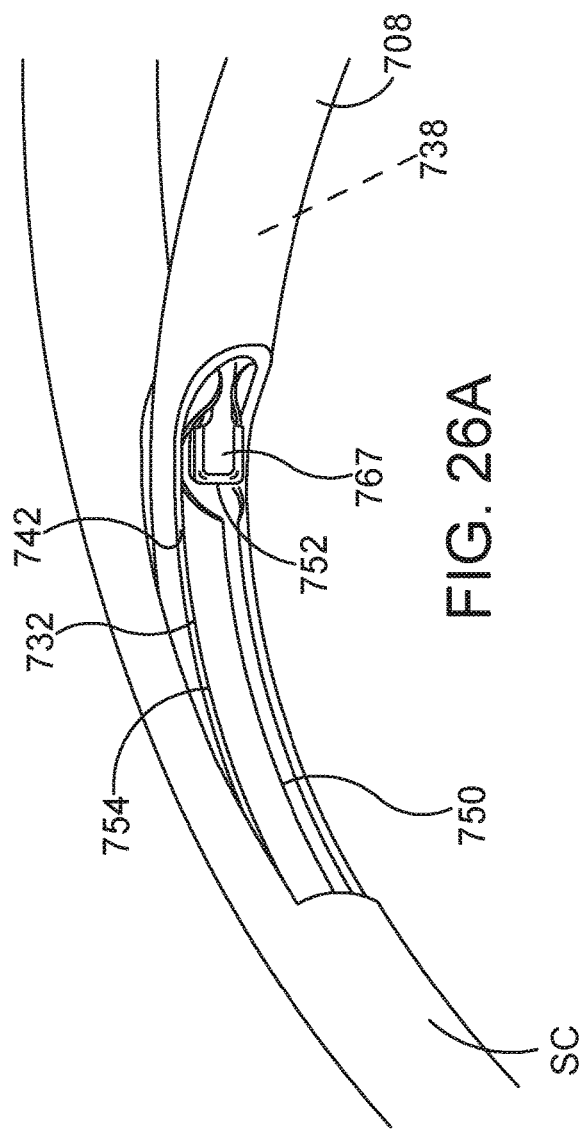
FIG. 26A is a stylized perspective view showing a cannula having a distal portion positioned so as to extend through the wall of Schlemm's canal. An ocular implant is shown extending out a distal opening of the cannula and into Schlemm's canal.

FIG. 26A is a stylized perspective view showing a cannula 708 having a distal portion positioned so as to extend through the wall of Schlemm's canal SC. The distal tip of cannula 708 may include a sharp portion configured for cutting and/or pierced the trabecular meshwork and the wall of Schlemm's canal so that a passageway 738 defined by the cannula can be placed in fluid communication with the lumen defined by Schlemm's canal. With the passageway of the cannula placed in fluid communication with the lumen of Schlemm's canal, an ocular implant 750 can be advanced out of the distal opening of the cannula and into Schlemm's canal. Insertion of the ocular implant into Schlemm's canal may facilitate the flow of aqueous humor out of the anterior chamber of the eye.

In FIG. 26A, delivery tool 752 is shown extending out of passageway 738 defined by a cannula 708. A surface 767 of delivery tool 752 rests against an inner wall surface of cannula 708 to keep delivery tool 752 interlocked with ocular implant 750. A distal portion of cannula 708 defines a trough 754 that communicates with passageway 738 defined by the cannula wall. Trough 754 opens out the distal end of cannula 708. Trough 754 also opens into an elongate opening 732 defined by the edge 742 of the cannula wall.

Figure 26B:
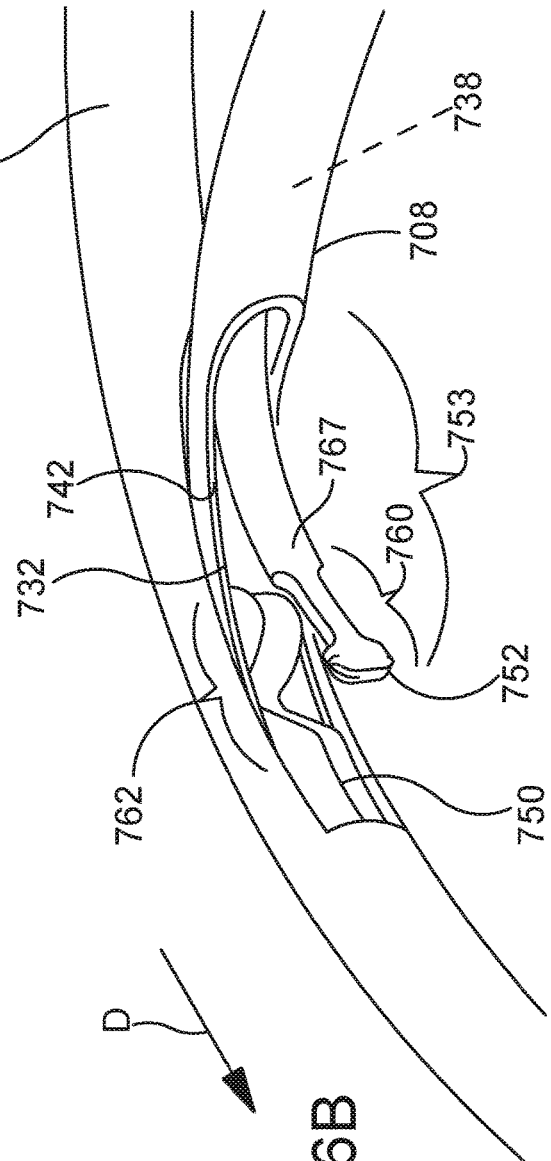
FIG. 26B is an additional perspective view showing the ocular implant and the cannula shown in FIG. 26A.

FIG. 26B is an additional perspective view showing ocular implant 750 and cannula 708 shown in the previous figure. By comparing FIG. 26B with the previous figure, it will be appreciated that ocular implant 750 and delivery tool 752 have advanced further distally so that part of delivery tool surface 767 and part of distal curved portion 753 have now passed through opening 732, thereby permitting the distal tool portion to move toward its curved at-rest shape so that the delivery tool interlocking portion 760 disengages and moves away from its complementary interlocking portion 762 on the ocular implant 750.

Reference is now made to both FIG. 26A and FIG. 26B which may be collectively referred to as FIG. 26. In the embodiment of FIG. 26, ocular implant 750 tracks along trough 754 as it is advanced distally along cannula 708. The trough opening allows the physician to monitor the progress of the implant by viewing the implant structures as they advance through the trough prior to entering Schlemm's canal. The trough opening also allows the physician to identify the position of the proximal end of the ocular implant with respect to the incision made by the cannula to access Schlemm's canal. Additionally, the trough opening allows the physician to see when the delivery tool is going to release the implant to monitor when he or she will lose the ability to retract the implant.

Figure 27A:
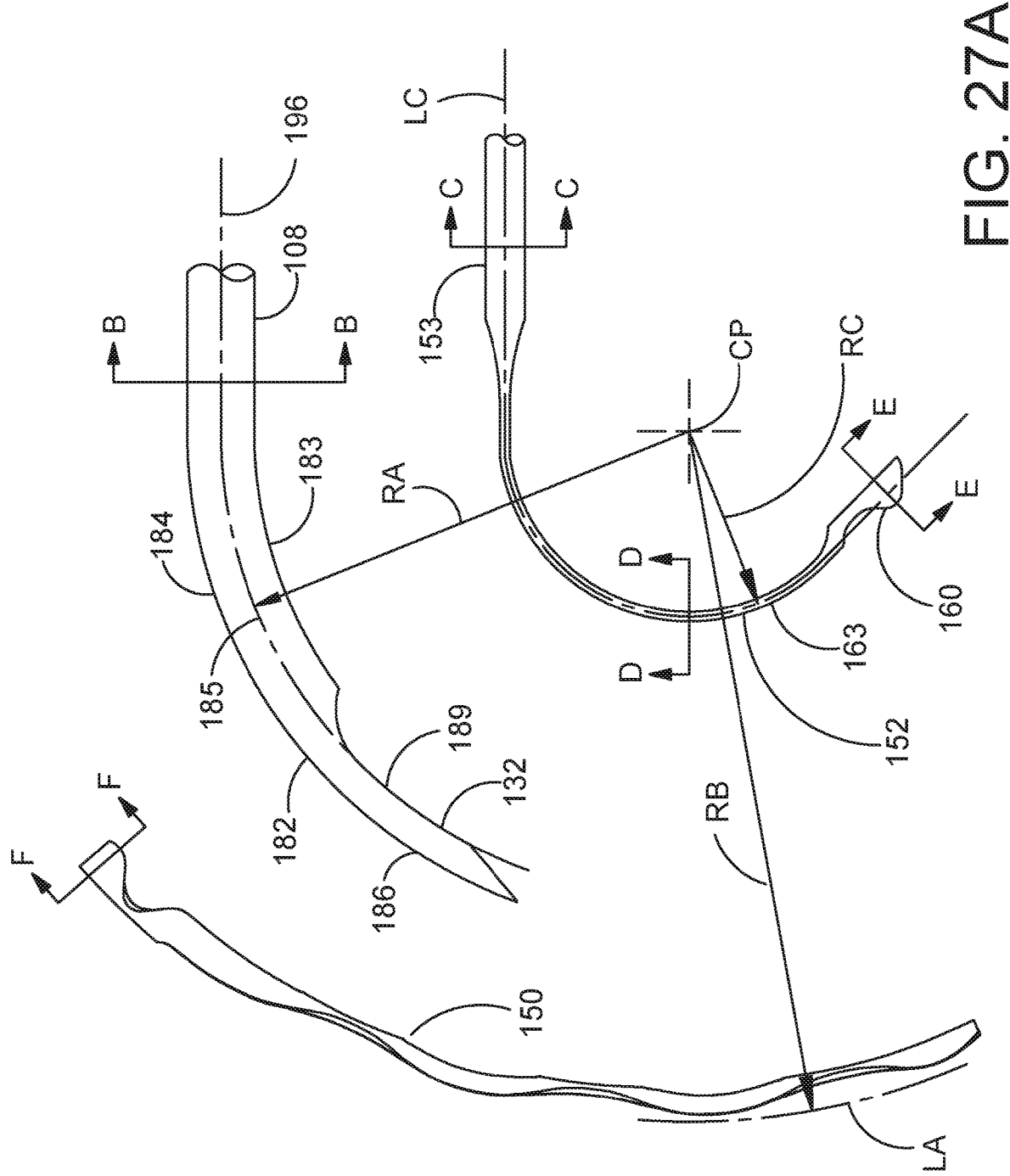
FIG. 27A is a top view showing a cannula and a delivery tool.

FIG. 27A is a top view showing a cannula 108 and a delivery tool 152. Cannula 108 and delivery tool 152 may form part of a delivery system for delivering an ocular implant 150 in the eye of a patient. The delivery tool 152 and/or the ocular implant can comprise an elastic or bendable material configured to assume a pre-determined shape, such as a shape memory material, for example. As shown in FIG. 27A, body 182 of cannula 108 comprises a first side 183 and a second side 184 that extend along opposite sides of a longitudinal center axis 196. Longitudinal center axis 196 includes a curved portion 185 having a radius RA. In FIG. 27A, radius RA can be seen extending from a curvature center point CP to longitudinal center axis 196.

Delivery tool 152 comprises a proximal portion 153, a distal interlocking portion 160, and a ribbon portion 163 that extends between proximal portion 153 and distal interlocking portion 160. In the embodiment of FIG. 27A, no external forces are acting on delivery tool 152 and ribbon portion 163 is free to assume a predetermined or unbiased and undeformed shape. In some embodiments, the predetermined shape can comprise a curved resting shape. With reference to FIG. 27A, delivery tool 152 has a radius of curvature RC when it is free to assume the undeformed shape. Radius RC can be seen extending from curvature center point CP to a longitudinal axis LC of delivery tool 152 in FIG. 27A. With reference to FIG. 27A, the radius RC of delivery tool 152 is smaller than the radius RA of cannula 108. As will be described in more detail below, the ocular implant 150 can be configured to engage the delivery tool 150 within a passageway of the cannula. In some embodiments, a trough portion 189 of distal opening 132 of cannula 108 is dimensioned and positioned such that, when ocular implant 150 reaches a predefined location along the passageway of the cannula, the distal portion of delivery tool 152 will be free to move toward a curved at-rest shape to release the ocular implant.

In the embodiment of FIG. 27A, no external forces are acting on the ocular implant and ocular implant 150 is free to assume an undeformed shape. With reference to FIG. 27A, ocular implant 150 has a radius of curvature RB when it is free to assume the undeformed shape. Radius RB of ocular implant 150 can be seen extending from a curvature center point CP to a longitudinal axis LA of ocular implant 150 in FIG. 27A. Ocular implant 150 may comprise, for example, the ocular implant disclosed in US Patent Publ. No. 2011/0009958.

With reference to FIG. 27A, the radius RA of cannula 108 is smaller than the radius RB of ocular implant 150. This arrangement allows the elastic behavior of the ocular implant to bias the ocular implant against an inner surface of cannula 108 as the distal end of ocular implant 150 travels through trough 186 of the cannula. Biasing the ocular implant against the inner surface of the trough helps assure that the distal end of the ocular implant travels between the inner surface of the trough and tissue covering a portion of the distal opening 132. This arrangement also helps assure that the distal end of the ocular implant follows the path defined by trough 186 as it is advanced in a distal direction through the cannula.

Ocular implant 150, delivery tool 152 and cannula 108 may be fabricated from various biocompatible materials possessing the necessary structural and mechanical attributes. Both metallic and non-metallic materials may be suitable. Examples of metallic materials include stainless steel, tantalum, gold, titanium, and nickel-titanium alloys known in the art as Nitinol. Nitinol is commercially available from Memory Technologies (Brookfield, Conn.), TiNi Alloy Company (San Leandro, Calif.), and Shape Memory Applications (Sunnyvale, Calif.). Nitinol is one advantageous material for ocular implant 150 and delivery tool 152 due to its super elastic properties. Stainless Steel can be used for cannula 108 due to its mechanical strength and ability to maintain its shape and cause ocular implant 150 and deliver tool 152 to conform within it.

FIG. 27B is a cross-sectional view of cannula 108 taken along section line B-B shown in FIG. 27A. As shown in FIG. 27B, cannula 108 has an inner diameter D1. Cannula 108 of FIG. 27B defines a lumen 187. In some embodiments, the cannula defines a trough and a lumen that define a pathway extending from a location outside of the eye to a location inside Schlemm's canal when a distal point of the cannula is inside Schlemm's canal of the eye. An ocular implant can be delivered into Schlemm's canal by advancing the ocular implant along the pathway defined by the lumen and the trough.

FIG. 27C, FIG. 27D and FIG. 27E are cross-sectional views of delivery tool 152 shown in the previous figure. These section views correspond to section lines shown in FIG. 27A. More particularly, FIG. 27C, FIG. 27D and FIG. 27E correspond to section line C-C, D-D, and E-E, respectively. FIGS. 27A through 27F may be collectively referred to as FIG. 27. In the embodiment of FIG. 27, proximal portion 153, distal interlocking portion 160, and ribbon portion 163 of delivery tool 152 can all have an outer diameter D2. In some useful embodiments, delivery tool 152 is fabricated by removing material from a wire having a generally cylindrical shape. As shown in FIG. 27D, ribbon portion 163 of delivery tool 152 has a thickness T that extends between a first major side 112 of ribbon portion 163 and a second major side 114 of ribbon portion 163.

In some embodiments, the outer diameter of the ribbon portion can be only slightly smaller than the inner diameter of the cannula so that the ribbon portion tracks along the widest part of the cannula lumen and so that support provided by the cannula wall makes it less likely that ribbon portion will buckle. The outer diameter of the ribbon portion may be designed to be smaller than the inner diameter of the cannula by a selected clearance value. In some useful embodiments, the clearance value is less than two times the wall thickness of the ocular implant. In some embodiments, a clearance value can be between about 0.0005 inches and about 0.0010 inches.

FIG. 27F is a cross-sectional view of an ocular implant 150 taken along section line F-F shown in FIG. 27A. With reference to FIG. 27, it will be appreciated that ocular implant 150 and distal interlocking portion 160 of delivery tool 152 both have an outer diameter D2. In some useful embodiments, the ocular implant and the distal interlocking portion of the delivery tool have an outer diameter designed to provide a carefully selected clearance between those elements and the inner diameter of the cannula. The clearance is large enough to allow the delivery tool and the ocular implant to slide along the lumen of the cannula. At the same time, the clearance is small enough to prevent unintentional release of the ocular implant, for example, when the complimentary interlocking portion of the ocular implant climbs over the interlocking portion of the delivery tool. The clearance is also small enough to reduce the likelihood that the ocular implant will become jammed, for example, when the wall of the ocular implant becomes lodged between the delivery tool and the inner diameter of the cannula. In some embodiments, the clearance value is less than two times the wall thickness of the ocular implant.

Figure 27H:
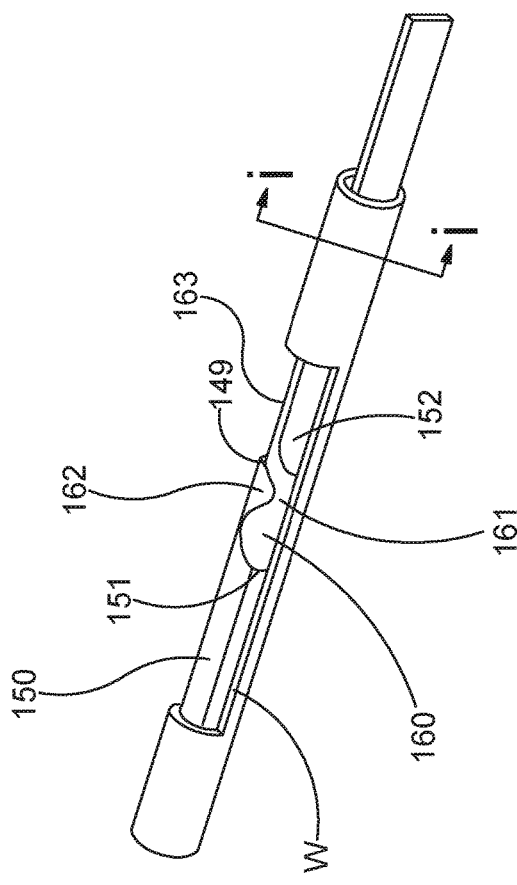
FIG. 27H is a perspective view of an assembly including a cannula, delivery tool and ocular implant.
Figure 27G:
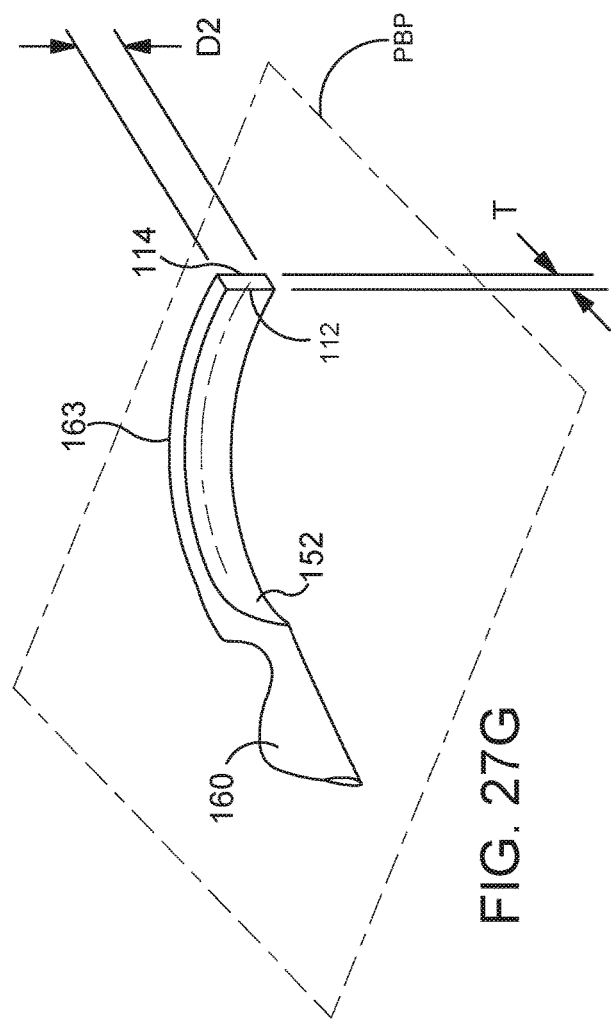
FIG. 27G is an isometric view showing a distal portion of the delivery tool.

FIG. 27G is an isometric view showing a distal portion of delivery tool 152. Delivery tool 152 comprises a proximal portion (not shown), a distal interlocking portion 160, and a ribbon portion 163 that extends between the proximal portion and distal interlocking portion 160. In the embodiment of FIG. 27A, no external forces are acting on delivery tool 152. As shown in FIG. 27G, ribbon portion 163 of delivery tool 152 can be biased to assume a curved resting shape when no external forces are acting on it (e.g., external forces from an interior surface of the cannula).

Ribbon portion 163 of delivery tool 152 has an outer diameter D2 and a thickness T. As shown in FIG. 27G, thickness T extends between a first major side 112 of ribbon portion 163 and a second major side 114 of ribbon portion 163. With reference to FIG. 27G, it will be appreciated that outer diameter D2 is greater than thickness T. In some useful embodiments, an aspect ratio of outer diameter to thickness is also selected so that the ribbon portion preferentially bends along a preferential bending plane. In the embodiment of FIG. 27G, the thickness of the ribbon portion is selected so that the ribbon portion preferentially bends along a preferential bending plane PBP.

Is some delivery system designs, the delivery tool is oriented within the cannula so that a preferential bending plane of the ribbon portion is co-planar with a curvature plane of the cannula. This coplanar orientation assures that when the ocular implant reaches a predefined location (e.g., the trough portion) along the passageway of the cannula, the distal portion of delivery tool 152 will be free to move toward a curved at-rest shape to release the ocular implant.

FIG. 27H is a perspective view of an assembly including cannula 108, delivery tool 152 and ocular implant 150. For purposes of illustration, a hypothetical window W is cut through the wall of cannula 108 in FIG. 27H. By comparing FIG. 27H with the previous figure, it can be seen how cannula 108 prevents ribbon portion 163 of delivery tool 152 from assuming its curved at rest shape when the ribbon portion of delivery tool 152 is inside the lumen of the cannula.

An interlocking portion 160 of a delivery tool 152 and a complementary interlocking portion 162 of ocular implant 150 are visible through window W. In the embodiment of FIG. 27H, interlocking portion 160 of delivery tool 152 and complementary interlocking portion 162 of ocular implant 150 are engaging each other so that a proximal end 149 of ocular implant 150 is proximal to the distal end 151 of delivery tool 152. Surface 161 of delivery tool 152 rests against the wall of cannula 108 to prevent interlocking portion 160 of delivery tool 152 and complementary interlocking portion 162 of ocular implant 150 from disengaging one another. When they are connected in this fashion, delivery tool 152 and ocular implant 150 move together as the delivery tool is advanced and retracted relative to cannula 108 by the delivery system mechanism.

In some embodiments, the ocular implant and the distal interlocking portion of the delivery tool have an outer diameter designed to provide a carefully selected clearance between those elements and the inner diameter of the cannula. The clearance is large enough to allow the delivery tool and the ocular implant to slide along the lumen of the cannula. At the same time, the clearance is small enough to prevent unintentional release of the ocular implant, for example, when the complimentary interlocking portion of the ocular implant climbs over the interlocking portion of the delivery tool. The clearance is also small enough to reduce the likelihood that the ocular implant will become jammed, for example, when the wall of the ocular implant becomes lodged between the delivery tool and the inner diameter of the cannula. In some useful embodiments, the clearance value is less than two times the wall thickness of the ocular implant.

Figure 27I:
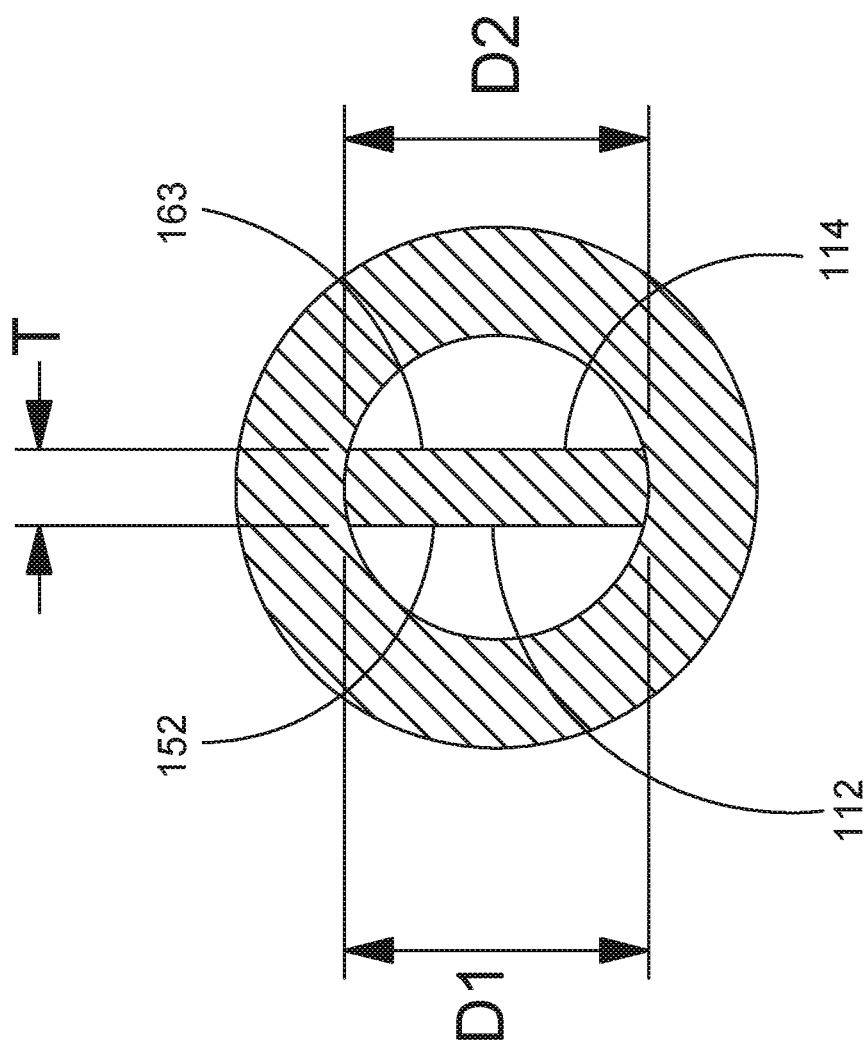
FIG. 27I is a cross-sectional view of a cannula and delivery tool taken along section line i-i shown in FIG. 27H.

FIG. 27I is a cross-sectional view of cannula 108 and delivery tool 152 taken along section line i-i shown in FIG. 27H. Ribbon portion 163 of delivery tool 152 has an outer diameter D2 and a thickness T. As shown in FIG. 27I, thickness T extends between a first major side 112 of ribbon portion 163 and a second major side 114 of ribbon portion 163. As shown in FIG. 27I, cannula 108 has an inner diameter D1. In some useful embodiments, the outer diameter of the ribbon portion is only slightly smaller than the inner diameter of the cannula so that the ribbon portion tracks along the widest part of the cannula lumen and so that support provided by the cannula wall makes it less likely that ribbon portion will buckle. The outer diameter of the ribbon portion may be designed to be smaller than the inner diameter of the cannula by a selected clearance value.

FIG. 27J is a perspective view showing an assembly including a cannula 108 and a distal portion of a delivery tool 152. In the embodiment of FIG. 27J, delivery tool 152 is assuming a somewhat curved shape in which the distal portion of the delivery tool extends through the trough portion 189 of distal opening 132. In the embodiment of FIG. 27J, trough portion 189 begins having a width equal to the inner diameter of cannula 108 at a point P. In some embodiments, the trough opening has a width that is substantially equal to an inner diameter of the cannula and both the ribbon portion and the distal interlocking portion of the delivery tool have an outer diameter slightly smaller than the inner diameter of the cannula so that a distal portion of the delivery tool can pass through the trough opening when the delivery tool reaches the predetermined location along the pathway defined by the cannula. When the distal interlocking portion of the delivery tool reaches the point P where the full trough width starts it is free to flex radially towards the trough opening through the distal opening of the cannula. The outer diameter of both the ribbon portion and the distal interlocking portion of the delivery tool may be designed to be smaller than the inner diameter of the cannula by a selected clearance value.

Figure 28:
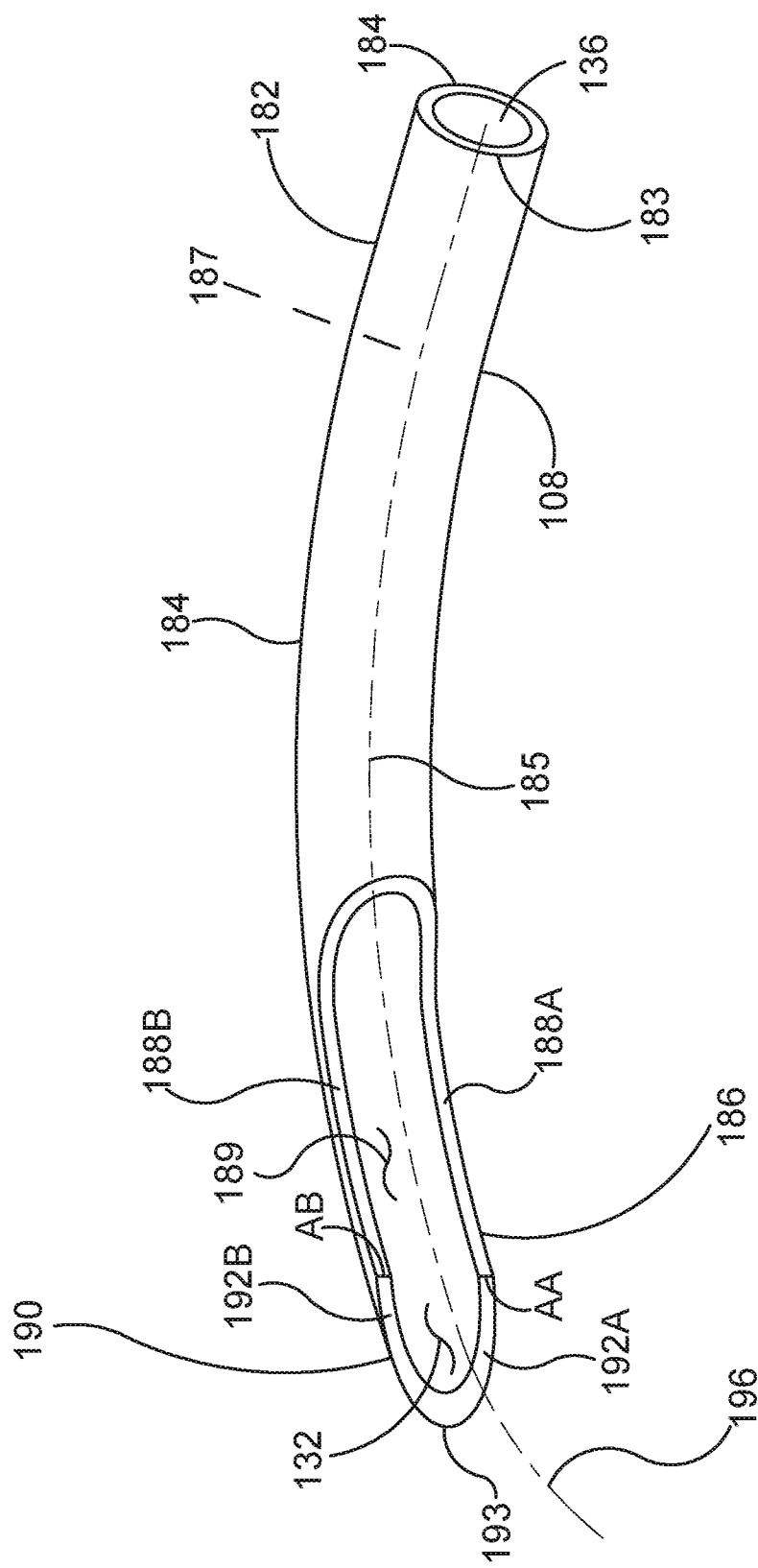
FIG. 28 is a perspective view of a cannula.

FIG. 28 is a perspective view of a cannula 108 in accordance with the present detailed description. Cannula 108 of FIG. 28 comprises a body 182 having a first side 183 and a second side 184. In FIG. 28, first side 183 and second side 184 can be seen extending along opposite sides of a longitudinal center axis 196 of cannula 108. Longitudinal center axis 196 includes a curved portion 185. In the embodiment of FIG. 28, first side 183 is disposed on a radially inward side of curved portion 185 of longitudinal center axis 196. Second side 184 is disposed on a radially outward side of curved portion 185 of longitudinal center axis 196 in the embodiment of FIG. 28.

Body 182 of FIG. 28 includes a trough 186 that opens through first side 183. The trough 186 can define an open groove portion of the cannula. Body 182 also defines a lumen 187 that extends from trough 186 to a proximal opening 136 of body 182. In some embodiments, the body is sized and configured so that the trough and the lumen define a pathway extending from a location outside of the eye to a location inside Schlemm's canal when a distal point of the cannula is inside Schlemm's canal of the eye. An ocular implant can be delivered into Schlemm's canal by advancing the ocular implant along the pathway defined by the lumen and the trough. Examples of ocular implants that may be delivered through the cannula of this invention may be found, e.g., in U.S. Pat. No. 7,740,604; US Patent Publ. No. 2009/0082860; US Patent Publ. No. 2009/0082862; US Patent Publ. No. 2009/0227934; and US Patent Publ. No. 2011/0009958.

Trough 186 comprises a first trough edge 188A, a second trough edge 188B, and an intermediate wall extending between first trough edge 188A and second trough edge 188B. In the embodiment of FIG. 28, the intermediate wall has a generally semi-circular transverse cross-sectional shape. A trough portion 189 of distal opening 132 extends between first trough edge 188A and second trough edge 188B opposite the intermediate wall.

In some useful embodiments, trough 186 is configured to receive the entire external cross section of an ocular implant as the ocular implant is being advanced into Schlemm's canal. When this is the case, trough 186 may have a depth dimension that is deeper than a height of the ocular implant. This cannula configuration allows the distal end of the ocular implant to be advanced under tissue that is covering the trough.

Cannula 108 and trough 186 include a tapered distal tip 190 extending distally from second side 184 of body 182. Tapered distal tip 190 comprises a first leading edge 192A, a second leading edge 192B, and an intermediate wall extending between first leading edge 192A and second leading edge 192B. In the embodiment of FIG. 28, the intermediate wall has a generally semi-circular transverse cross-sectional shape. First leading edge 192A and second leading edge 192B both distally converge toward a distal point 193 of tapered distal tip 190. In some useful embodiments, distal point 193 of tapered distal tip 190 is sufficiently blunt to slide along the outer major wall of Schlemm's canal without cutting the scleral tissue underlying the outer major wall of Schlemm's canal. A distal opening 132 extends between first leading edge 192A and second leading edge 192B of tapered distal tip 190 opposite the intermediate wall.

First leading edge 192A of tapered distal tip 190 meets first trough edge 188A at a first apex AA. Second leading edge 192B of tapered distal tip 190 meets second trough edge 188B at a second apex AB. During a delivery procedure, tapered distal tip 190 may be inserted into Schlemm's canal until first apex AA and second apex AB are aligned with the incision made to enter Schlemm's canal. It is an important aspect of this design that the apex points, the length of the trough opening 189 and the curve profile of the delivery tool are all configured to enable the delivery system to automatically deploy the ocular implant in the correct position when first apex AA and a second apex AB are aligned with the incision.

After the cannula is positioned properly in Schlemm's canal, the delivery tool can be advanced along the lumen of the cannula. When the distal interlocking portion of the delivery tool reaches the point where the full trough width starts, the delivery tool is free to flex radially towards the trough opening through the distal opening of the cannula. The ocular implant is automatically released from the delivery system as the distal interlocking portion of the delivery tool moves away for the trough of the cannula and away from the ocular implant. Automatically releasing the ocular implant from the delivery system causes the inlet portion of the ocular implant to be consistently placed in the correct position with respect to Schlemm's canal. Automatically placing the inlet of the ocular implant in the correct location eliminates any need to adjust the position of the ocular implant after deployment. Automatically placing the inlet of the ocular implant in the correct location also eliminates any possibility of inserting the inlet portion of the ocular implant into Schlemm's canal. The automatic placement of the inlet of the ocular implant is particularly beneficial when the physician's view of the ocular implant is obstructed at the time of release. The physician's view may be obstructed, for example, by blood reflux.

FIG. 29A and FIG. 29B are plan views of cannula 108 shown in the previous figure. FIG. 29A and FIG. 29B may be collectively referred to as FIG. 29. The plan views of FIG. 29 were created using a technique known in the field of engineering drawing as multiview projection. In engineering drawing it is customary to refer to multiview projections using terms such as front view, top view, and side view and the like. In accordance with this convention, FIG. 29A may be referred to as a top view of cannula 108 and FIG. 29B may be referred to as a side view of cannula 108. The terms top view, side view, and bottom view are used herein as a convenient method for differentiating between the views shown in FIG. 29. It will be appreciated that cannula 108 shown in FIG. 29 may assume various orientations without deviating from the spirit and scope of this detailed description. Accordingly, the terms top view, side view, and bottom view should not be interpreted to limit the scope of the invention recited in the attached claims.

As shown in FIG. 29A, body 182 of cannula 108 comprises a first side 183 and a second side 184 that extend along opposite sides of a longitudinal center axis 196. Longitudinal center axis 196 includes a curved portion 185. In the embodiment of FIG. 29, first side 183 is disposed on a radially inward side of curved portion 185 of longitudinal center axis 196. Second side 184 is disposed on a radially outward side of curved portion 185 of longitudinal center axis 196 in the embodiment of FIG. 29.

As shown in FIG. 29B, body 182 of cannula 108 includes a trough 186 that opens through first side 183. Trough 186 comprises a first trough edge 188A, a second trough edge 188B, and a trough portion 189 of distal opening 132 extending between first trough edge 188A and second trough edge 188B. The cannula body 182 also defines a lumen 187 that fluidly communicates with trough 186 and extends to a proximal end of body 182. In some useful embodiments, the body is sized and configured so that the trough and the lumen define a pathway extending from a location outside of the eye to a location inside Schlemm's canal when a distal point 193 of the tapered distal tip 190 is inside Schlemm's canal of the eye.

As shown in FIG. 29B, cannula 108 includes a tapered distal tip 190 extending distally from second side 184 of body 182. Tapered distal tip 190 comprises a first leading edge 192A and a second leading edge 192B. First leading edge 192A and second leading edge 192B both distally converge toward a distal point 193 of tapered distal tip 190. In some embodiments, distal point 193 of tapered distal tip 190 is sufficiently blunt to slide along the outer major wall of Schlemm's canal without cutting the scleral tissue underlying the outer major wall of Schlemm's canal. A distal opening 132 of cannula 108 extends between first leading edge 192A and second leading edge 192B of tapered distal tip 190.

First leading edge 192A of tapered distal tip 190 meets first trough edge 188A at a first apex AA. Second leading edge 192B of tapered distal tip 190 meets second trough edge 188B at a second apex AB. During a delivery procedure, tapered distal tip 190 may be inserted into Schlemm's canal until first apex AA and second apex AB are aligned with the incision made to enter Schlemm's canal. Aligning the apex points with the incision enables a delivery system in accordance with this detailed description to automatically deploy the ocular implant in the correct position.

Figure 30A:
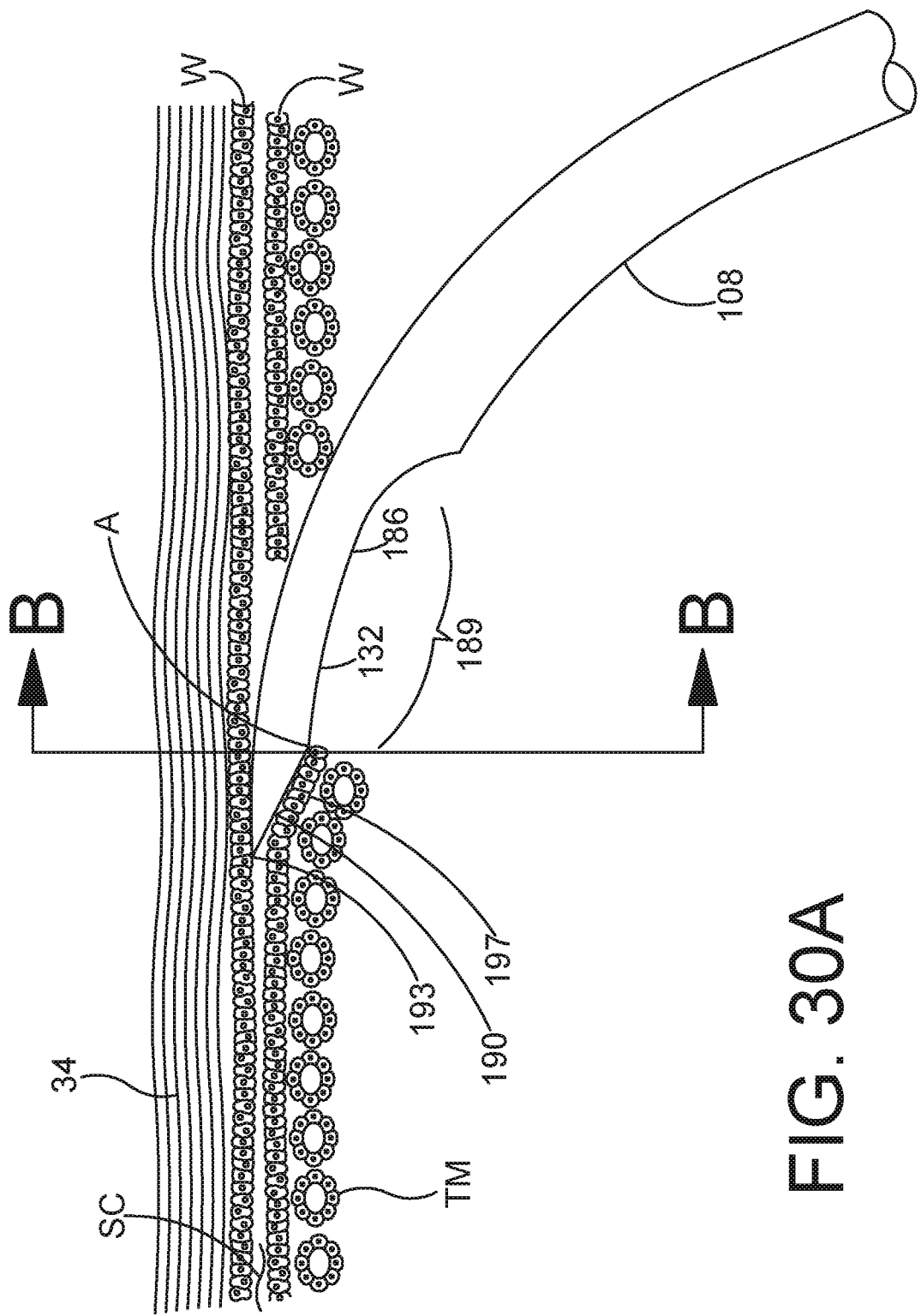
FIG. 30A is an additional top view of the cannula shown in the previous figure.

FIG. 30A is an additional top view of cannula 108 shown in the previous figure. In FIG. 30A, the distal point 193 of cannula 108 is shown having been advanced into and residing inside Schlemm's canal SC of a human eye. Schlemm's canal SC and various surrounding tissues are schematically illustrated in FIG. 30A. Schlemm's canal SC comprises a wall W that extends between scleral tissue 34 and the trabecular meshwork TM. As shown in FIG. 30A, a tissue tent 197 has been formed by lifting an inner portion of wall W away from an outer portion of wall W. Tissue tent 197 comprises tissues of Schlemm's canal wall W and trabecular meshwork TM that can be seen covering a portion of distal opening 132 in FIG. 30A.

With reference to FIG. 30A, the distal tip of cannula 108 has been inserted into Schlemm's canal SC up to the apex A of the distal tip at which tissue tent 197 intersects the trough portion 189 of distal opening 132. In some embodiments, the tapered distal tip 190 of cannula 108 is shaped and configured to lift and/or stretch trabecular meshwork TM and wall W over a portion of distal opening 132 as distal point 193 is advanced into Schlemm's canal. With reference to FIG. 30A, trough portion 189 of distal opening 132 is not covered by wall W and trabecular meshwork TM. The uncovered portion of distal opening 132 may allow a physician to see an ocular implant at it advances through trough 186.

Figure 30B:
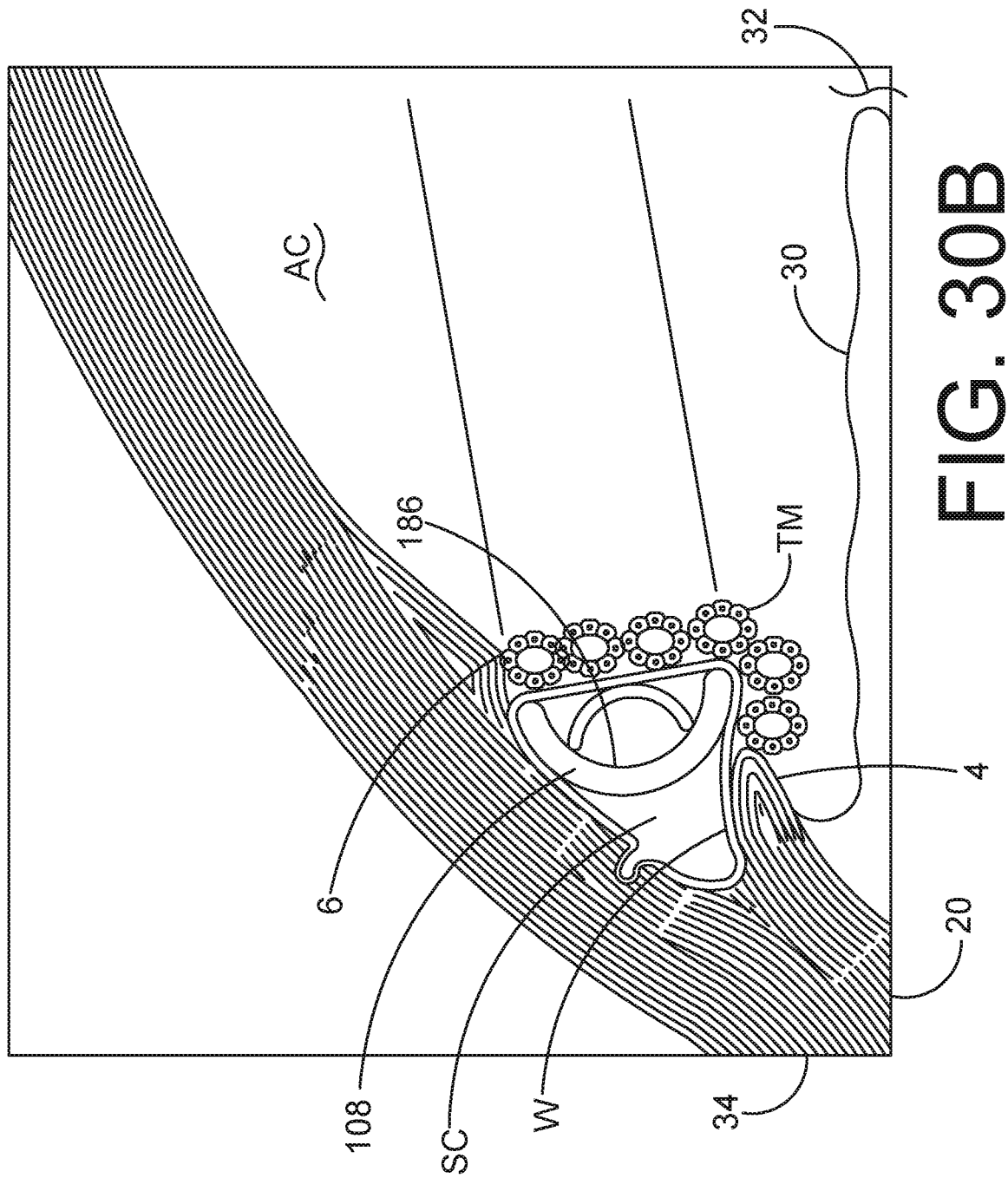
FIG. 30B is a stylized cross-sectional view taken along cutting plane B-B shown in FIG. 30A.

FIG. 30B is a stylized cross-sectional view taken along cutting plane B-B shown in FIG. 30A. The picture plane of FIG. 30B extends laterally across Schlemm's canal SC and trabecular meshwork TM of an eye 20. Additional ocular anatomy is shown in FIG. 30B to provide context and increase understanding. Eye 20 includes an iris 30 that defines a pupil 32 of the eye. Schlemm's canal SC may be conceptualized as a tube-like structure disposed between scleral tissue 34 and trabecular meshwork TM. Together, Schlemm's canal SC and trabecular meshwork TM extend along an outer edge of anterior chamber AC and encircle iris 30. As shown in FIG. 30B, Schlemm's canal wall W and trabecular meshwork TM are covering a portion of trough 186 of cannula 108. In FIG. 30B, trabecular meshwork TM is shown stretching between Schwalbe's line 6 and a scleral spur 4 of eye 20.

Figure 31:
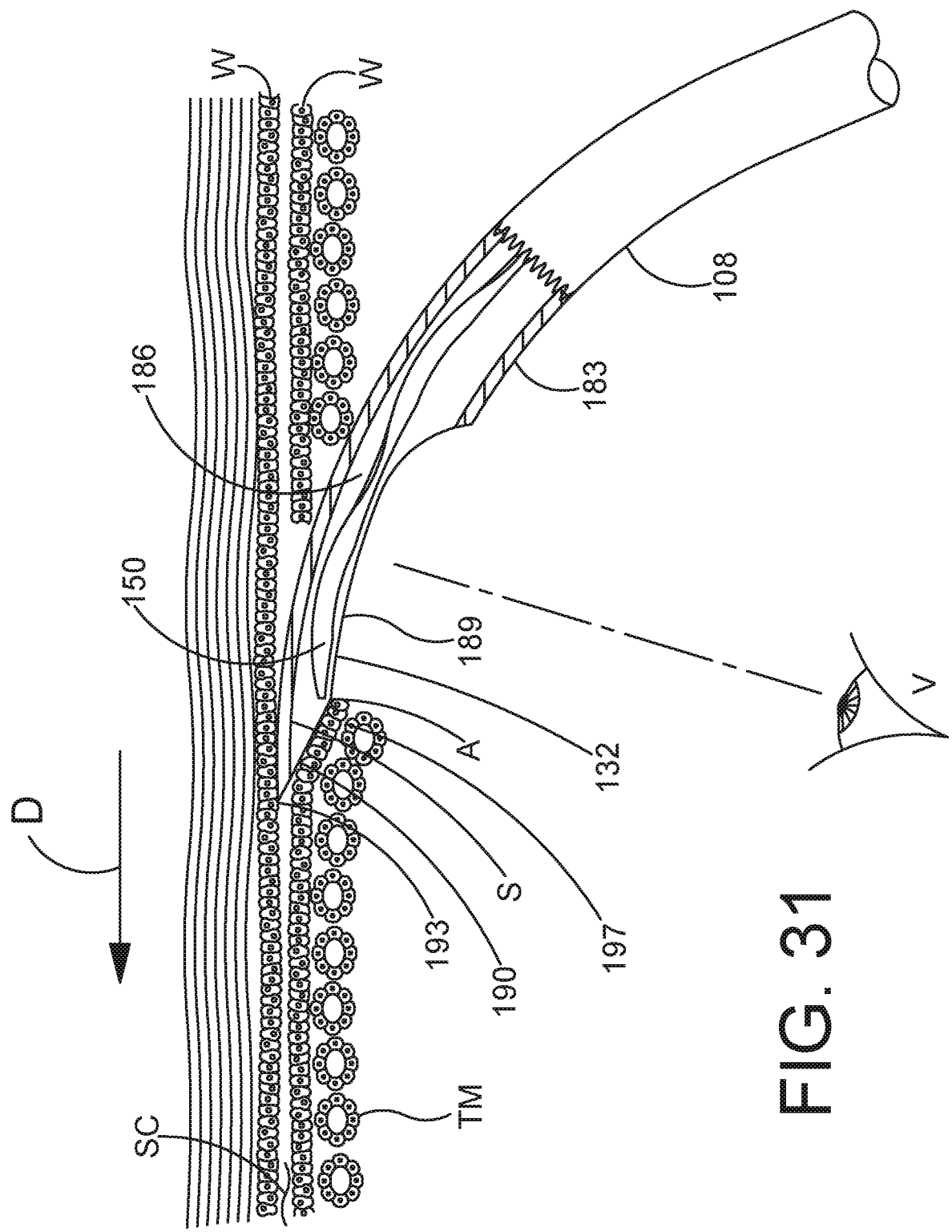
FIG. 31 is a cross-sectional view further illustrating the cannula shown in the previous figure.

FIG. 31 is a cross-sectional view further illustrating cannula 108 shown in the previous figure. In the cross-sectional view of FIG. 31, an ocular implant 150 can be seen advancing into trough 186 of cannula 108. The distal point 193 of tapered distal tip 190 is positioned inside Schlemm's canal SC of a human eye. In FIG. 31, tissues of Schlemm's canal wall W and trabecular meshwork TM can be seen extending over a distal portion of distal opening 132.

With reference to FIG. 31, trough 186 has a depth greater than the height of ocular implant 150 so that the distal end of the ocular implant will travel between an inner surface S of cannula 108 and the tissue covering the distal portion of distal opening 132 as ocular implant 150 moves in a distal direction D. Distal direction D is illustrated using an arrow in FIG. 31. This cannula configuration advantageously prevents the ocular implant from intersecting the layers of trabecular meshwork TM and wall W that are covering the distal portion of trough 186.

As shown in FIG. 31, trough 186 opens through a first side 183 of cannula 108. In the embodiment of FIG. 31, the length of trough portion 189 of distal opening 132 is selected to ensure correct positioning of the implant upon release and provide direct visualization of the ocular implant as it is advanced into Schlemm's canal SC. An exemplary line of sight used by a hypothetical viewer V is schematically illustrated using a dashed line in FIG. 31. A configuration allowing direct visualization of the ocular implant has a number of clinical advantages. During a medical procedure, it is often difficult to monitor the progress of the implant by viewing the implant through the trabecular meshwork. For example, blood reflux may push blood into Schlemm's canal obstructing a physician's view of the portion of the implant that has entered Schlemm's canal. With reference to FIG. 31, ocular implant 150 tracks along trough 186 as it is advanced distally along cannula 108. The trough portion of the distal opening allows the physician to release the implant such that the inlet extends into the AC a defined length; it also allows the user to monitor the progress of the implant by viewing the implant structures as they advance through the trough prior to entering Schlemm's canal. The trough portion of the distal opening also allows the physician to identify the position of the proximal end of the ocular implant with respect to the incision made by the cannula to access Schlemm's canal. Additionally, the trough portion of the distal opening allows the physician to see when the delivery tool is going to release the implant to monitor when he or she will lose the ability to retract the implant.

With reference to FIG. 31, tapered distal tip 190 of cannula 108 has been inserted into Schlemm's canal SC up to the apex A of the distal tip at which tissue tent 197 intersects the trough portion 189 of distal opening 132. During some delivery procedures, the physician's view through trough portion 189 may be obstructed by blood reflux. Accordingly, it is an important aspect of this design that the apex of the tapered distal tip, the length of trough opening 189 and the curved profile of the delivery tool are all configured to enable the delivery system to automatically deploy the ocular implant in the correct position when the apex of the tapered distal tip is aligned with the incision made to access Schlemm's canal. When the distal interlocking portion of the delivery tool reaches to the trough portion of the cannula, it will be free to flex radially towards the trough opening through the distal opening of the cannula. The ocular implant is automatically released from the delivery system as the distal interlocking portion of the delivery tool moves away for the ocular implant. Automatically releasing the ocular implant from the delivery system causes the inlet portion of the ocular implant to be consistently placed in the correct position with respect to Schlemm's canal. Automatically placing the inlet of the ocular implant in the correct location eliminates any need to adjust the position of the ocular implant after deployment. Automatically placing the inlet of the ocular implant in the correct location also eliminates any possibility of inserting the inlet portion of the ocular implant into Schlemm's canal.

Figure 32:
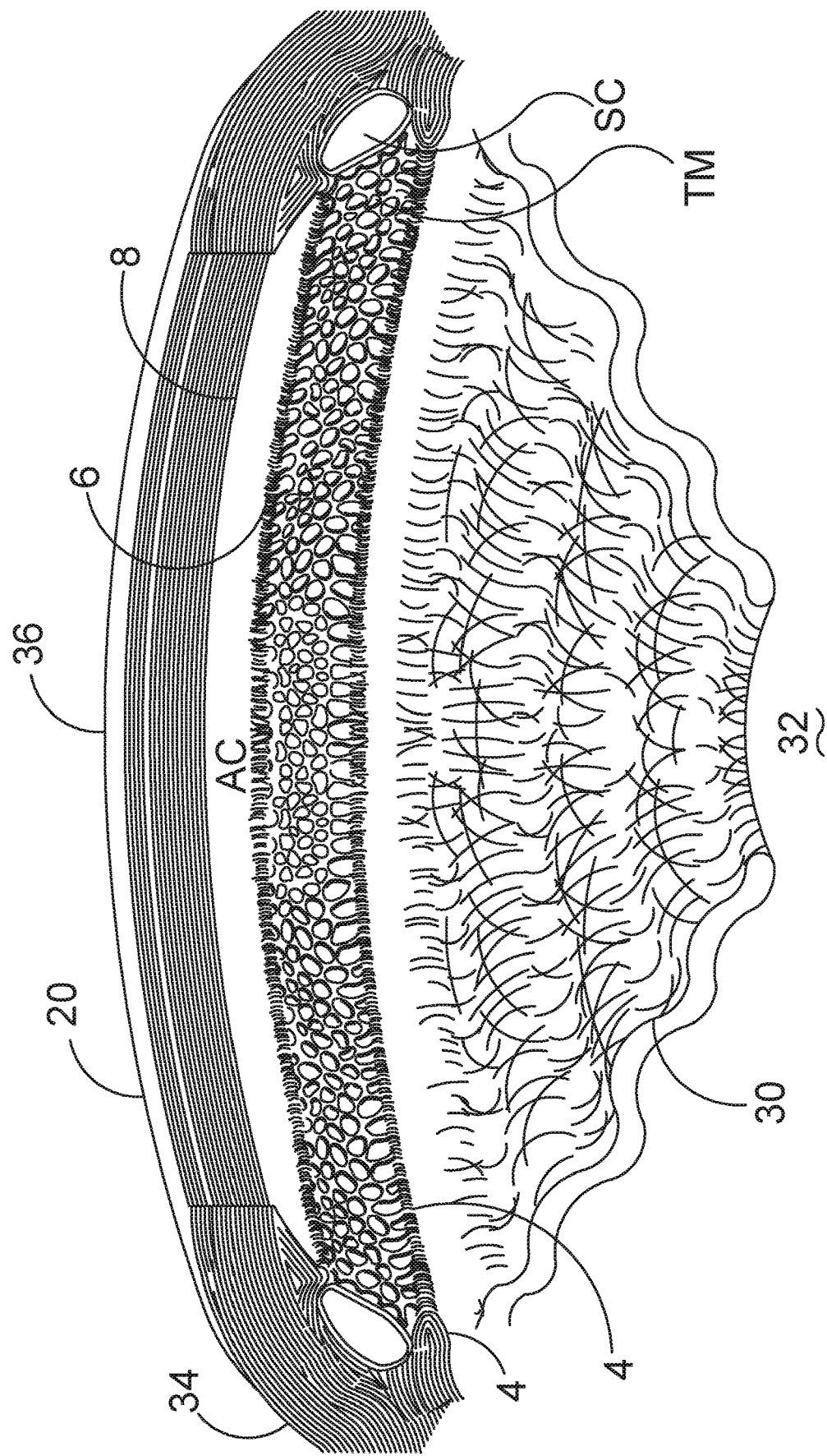
FIG. 32 is perspective view further illustrating the anatomy of the eye.

FIG. 32 is perspective view further illustrating the anatomy of eye 20. Eye 20 includes a dome-shaped wall that defines and encloses the anterior chamber AC. The dome-shaped wall of the eye comprises a cornea 36 and scleral tissue 34. The scleral tissue 34 meets the cornea 36 at a limbus of eye 20. The dome shaped wall includes a scleral spur 4 comprising scleral tissue 34. Schlemm's canal SC resides in a shallow depression in the scleral tissue located near scleral spur 4. The trabecular meshwork TM is fixed to scleral spur 4 and extends over Schlemm's canal SC. Together, Schlemm's canal SC, trabecular meshwork TM, and scleral spur 4 encircle anterior chamber AC along the dome shaped wall. Iris 30 of eye 20 is disposed inside the anterior chamber AC. Iris 30 defines a pupil 32. Descemet's membrane 8 is one of the inner-most layers of cornea 36. Descemet's membrane extends across cornea 36 toward Schlemm's canal SC and terminates at Schwalbe's line 6 near the upper edge of Schlemm's canal SC.

Figure 33:
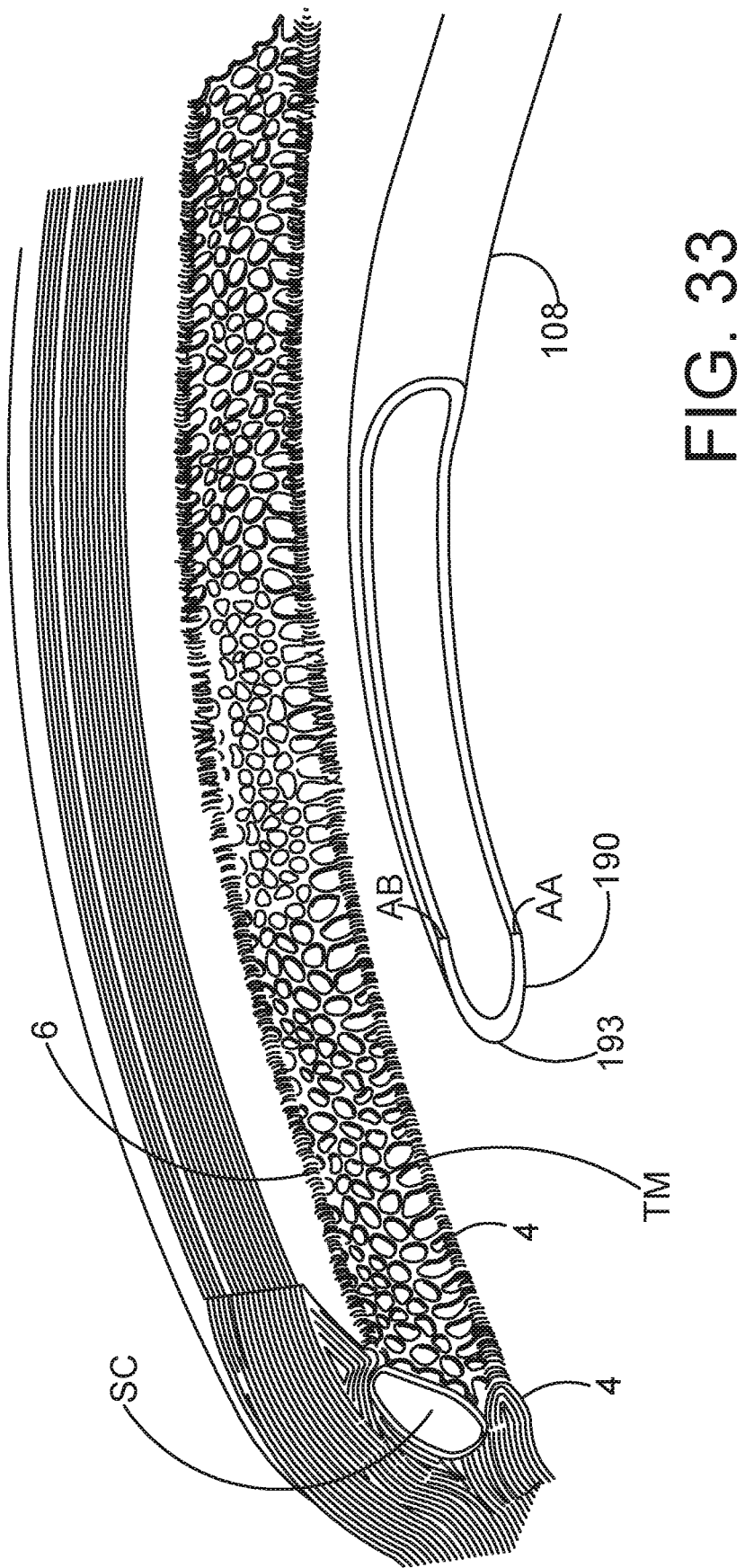
FIG. 33 is a perspective view showing selected structures from the eye shown in the previous figure.

FIG. 33 is a perspective view showing selected structures from the eye shown in the previous figure. In FIG. 33, a distal portion of cannula 108 can be seen residing in the anterior chamber of the eye. One function of cannula 108 is to delivery an ocular implant into Schlemm's canal SC. During a delivery procedure, distal point 193 of tapered distal tip 190 of cannula 108 may be advanced through trabecular meshwork TM and into Schlemm's canal. In some particularly useful methods, taper distal tip 190 is inserted into Schlemm's canal SC up to a first apex AA and a second apex AB of cannula 108. When distal point 193 is disposed in Schlemm's canal, cannula 108 will define a pathway extending from a location outside of the eye to a location inside Schlemm's canal. The ocular implant can be advanced along the pathway defined by cannula 108 inserted into Schlemm's canal.

In some embodiments, cannula 108 includes a curved distal portion that is dimensioned to be received within the anterior chamber of the eye. This curved portion may be configured to provide a pathway entering Schlemm's canal in a substantially tangential direction. When a physician is attempting to insert tapered distal tip 190 of cannula 108 into Schlemm's canal under gonio lens visualization, the physician may refer to anatomical landmarks of the eye. One convenient landmark is scleral spur 4 which has the appearance of a white line encircling the anterior chamber. Another convenient landmark is a pigment line centered on Schlemm's canal SC. An additional convenient landmark is Schwalbe's line 6.

Figure 34:
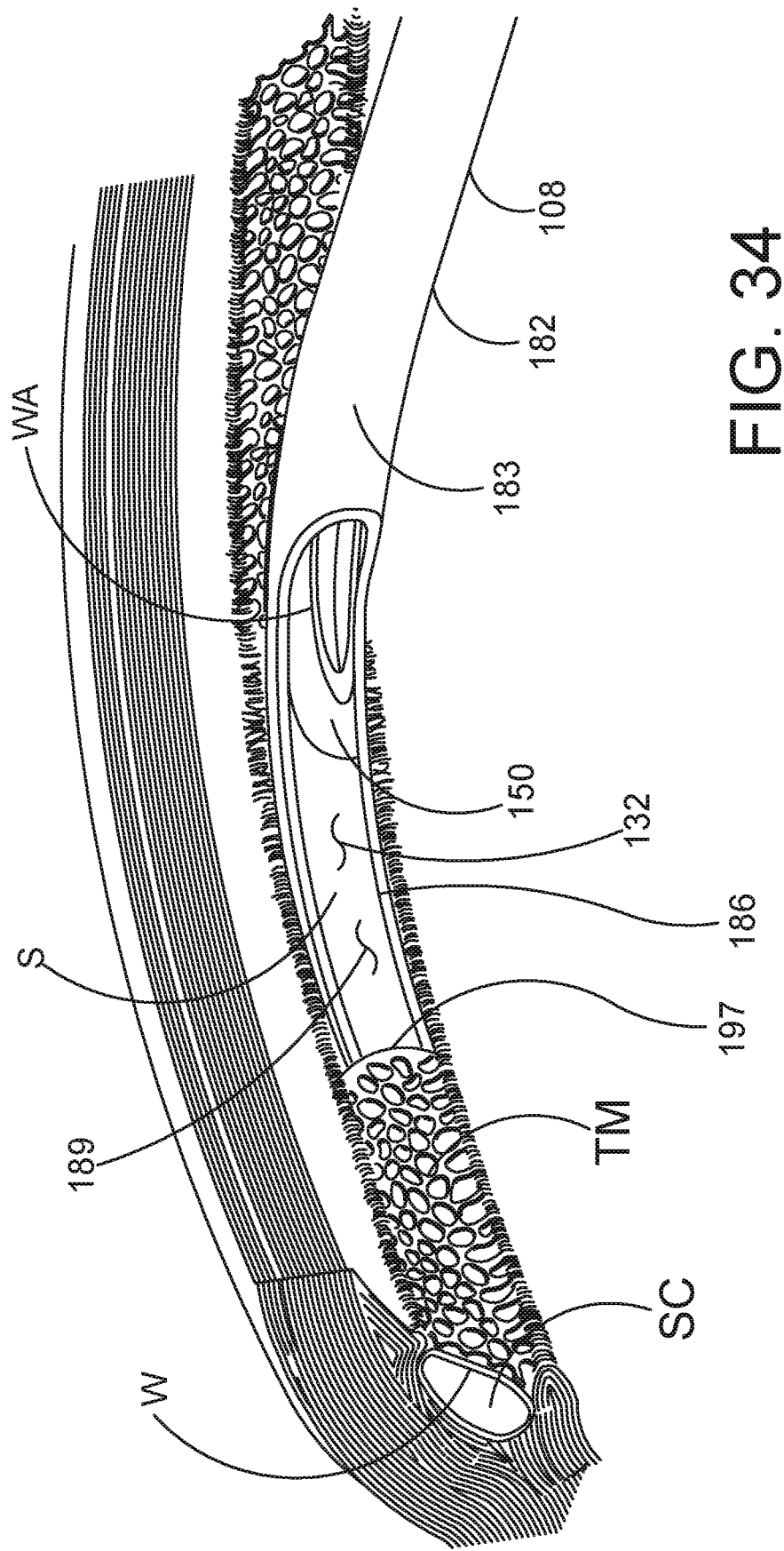
FIG. 34 is an additional perspective view of the ocular structures shown in the previous figure.

FIG. 34 is an additional perspective view of the ocular structures shown in the previous figure. In the embodiment of FIG. 34, the tapered distal tip of cannula 108 has been advanced into Schlemm's canal SC. A tissue tent 197 can be seen arching over a distal portion of cannula 108 in FIG. 34. With reference to FIG. 34 it will be appreciated that the distal tip of cannula 108 has been inserted into Schlemm's canal SC up to the first apex and the second apex of cannula 108 at which tissue tent 197 intersects the trough portion 189 of distal opening 132. In some useful embodiments, the tapered distal tip of cannula 108 is configured to lift a portion of Schlemm's canal wall W and trabecular meshwork TM away from the scleral tissue enclosing the anterior chamber of the eye.

The tissue tent 197 created by cannula 108 may facilitate delivery of an ocular implant 150 into Schlemm's canal SC. In FIG. 34, ocular implant 150 can be seen extending from the lumen of cannula 108 into its trough 186. During a delivery procedure, the distal end of ocular implant 150 may be advanced through tissue tent 197 and the distal opening of cannula 108 as it is inserted into Schlemm's canal. It is important to note that maintaining the relationship of the cannula apex A and the Schlemm's canal entry point will enable a delivery system in accordance with this detailed description to automatically and predictably release the implant in the correct location. The predictability of the resulting implant delivery location has far reaching benefits. If the field of view becomes compromised (e.g., filled with blood) during implant delivery and the user has maintained the position of cannula with respect to the Schlemm's canal entry point he or she can deliver ocular implant with a high degree of confidence that the delivery system in accordance with this detailed description will automatically release the ocular implant in the correct location.

Trough 186 of cannula opens through a first side 183 of the cannula body 182. As shown in FIG. 34, a first window WA of ocular implant 150 can be seen through trough portion 189 of distal opening 132. Windows and other structures of ocular implant can be observed through trough portion 189 of distal opening 132 to provide visual feedback regarding the movement of ocular implant 150 during a delivery procedure.

Figure 35:
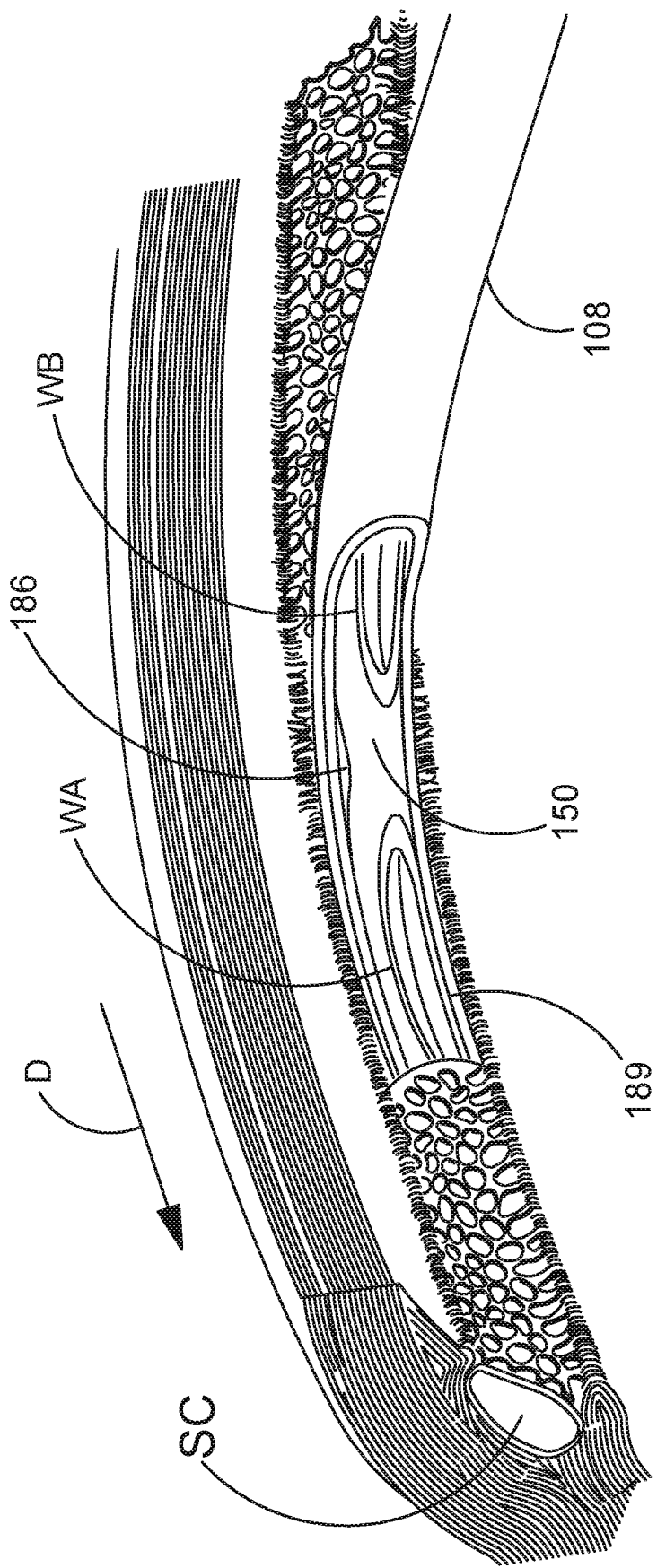
FIG. 35 is an additional perspective view showing the ocular implant and cannula shown in the previous figure.

FIG. 35 is an additional perspective view showing ocular implant 150 and cannula 108 shown in the previous figure. When comparing FIG. 35 with the previous figure, ocular implant 150 has been advanced in a distal direction D while cannula 108 has remained stationary so the distal end of ocular implant 150 is disposed inside Schlemm's canal SC. Because ocular implant 150 can be seen through trough portion 189 of distal opening 132, it will be appreciated that first window WA is now extending into Schlemm's canal and a second window WA of ocular implant 150 has come into view.

In the embodiment of FIG. 35, trough portion 189 of distal opening 132 has a length selected to provide direct visualization of ocular implant 150 while the first apex and the second apex of cannula 108 are aligned with the incision that provides entry into Schlemm's canal SC. A cannula configuration allowing direct visualization of the ocular implant has a number of clinical advantages. During a medical procedure, it is often difficult to monitor the progress of the implant by viewing the implant through the trabecular meshwork. For example, heavy pigmentation and/or blood reflux may push blood into Schlemm's canal obstructing a physician's view of the portion of the implant that has entered Schlemm's canal. With reference to FIG. 35, ocular implant 150 tracks along trough 186 as it is advanced distally along cannula 108. The trough portion of the distal opening allows the physician to monitor the progress of the implant by viewing the implant structures as they advance through the trough prior to entering Schlemm's canal. The trough portion of the distal opening also allows the physician to identify the position of the proximal end of the ocular implant with respect to the incision made by the cannula to access Schlemm's canal. Additionally, the trough portion of the distal opening allows the physician to see when the delivery tool is going to release the implant to monitor when he or she will lose the ability to retract the implant.

Figure 36:
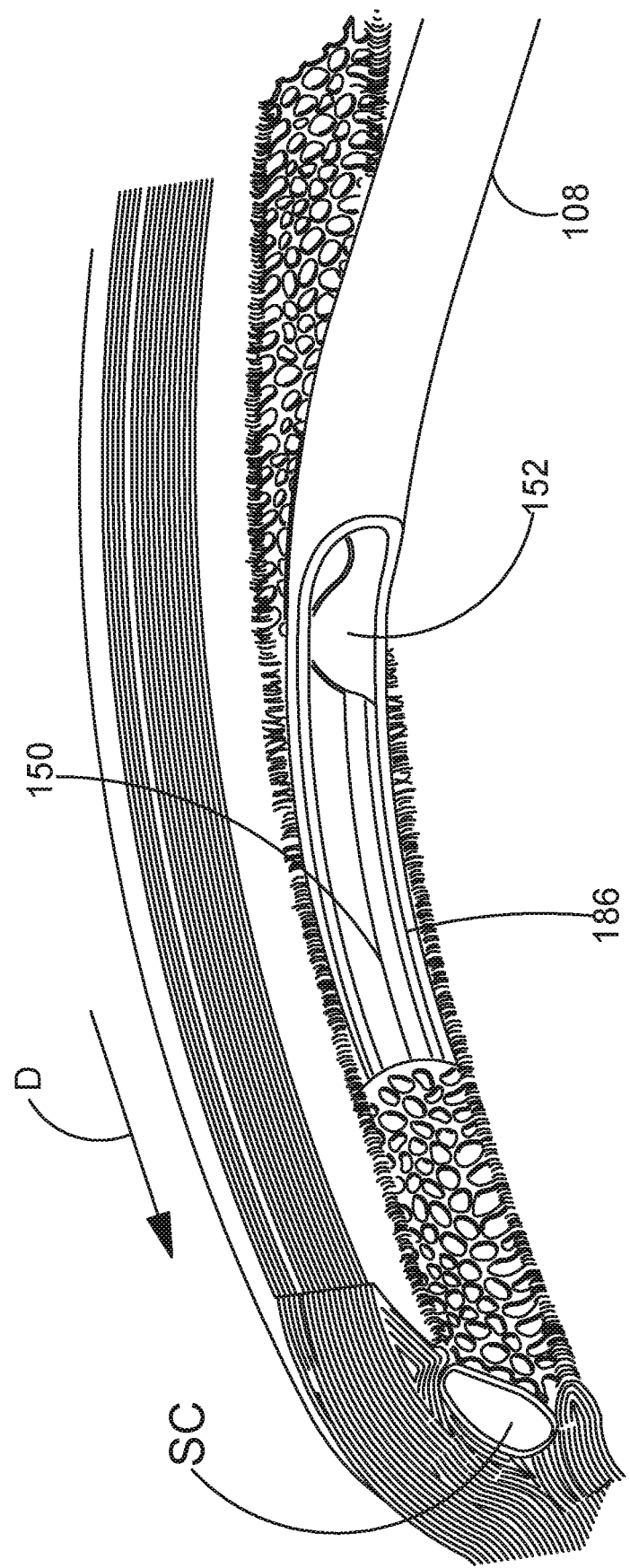
FIG. 36 is an additional stylized perspective view showing the ocular implant and cannula.

FIG. 36 is an additional stylized perspective view showing ocular implant 150 and cannula 108. In FIG. 36, mechanically interlocking portions of ocular implant 150 and a delivery tool 152 can be seen entering trough 186 of cannula 108. As shown in FIG. 36, ocular implant 150 has been advanced in a distal direction D (relative to the position shown in the previous figure) so that more of ocular implant 150 is disposed inside Schlemm's canal SC. An outer surface of delivery tool 152 is resting against an inner surface of cannula 108 to keep the delivery tool interlocked with ocular implant 150 in the embodiment of FIG. 36.

Figure 37:
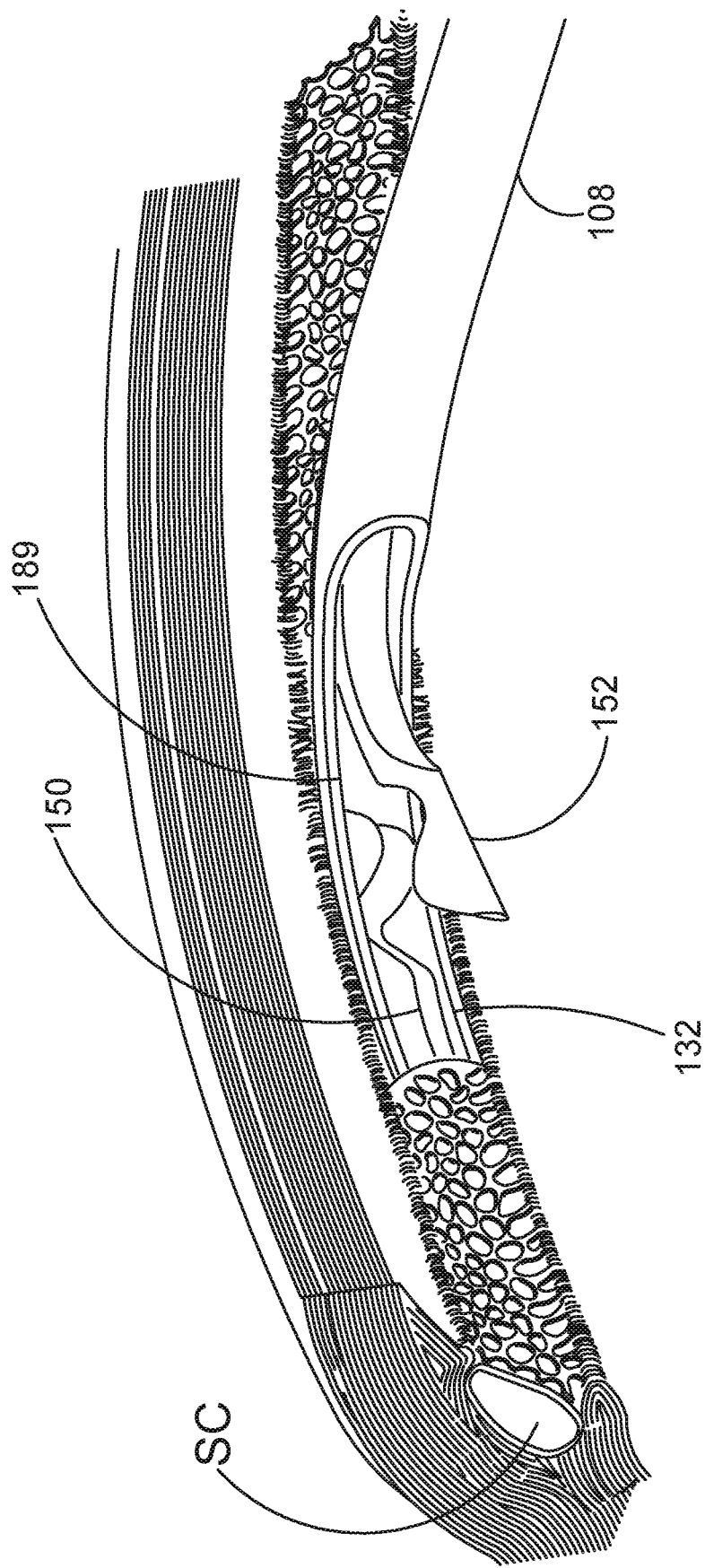
FIG. 37 is an additional stylized perspective view showing the ocular implant and cannula.

FIG. 37 is an additional stylized perspective view showing ocular implant 150 and cannula 108. In the embodiment of FIG. 37, the connection previously formed between the interlocking portions of delivery tool 152 and ocular implant 150 has been broken, since the distal portion of the delivery tool been advanced into the trough portion of the cannula and flexed towards the trough opening away from the implant and cannula. With reference to FIG. 37, it will be appreciated that a distal portion of delivery tool 152 has moved radially away from ocular implant 150.

In the embodiment of FIG. 37, trough portion 189 of distal opening 132 is shaped and dimensioned so as to allow a distal portion of delivery tool 152 to extend therethrough when ocular implant 150 reaches the fully deployed position shown in FIG. 37. With reference to FIG. 37, it will be appreciated that when the distal portion of delivery tool 152 reaches the point at which the full trough width begins, it is free to assume a curved, unstressed shape extending through the trough portion 189 of distal opening 132. In this manner, the delivery system releases ocular implant 150 when the ocular implant reaches the fully deployed position. In some useful embodiments, the delivery tool may be colored to provide visual differentiation from the implant. Flexing radially through the trough opening to assume the curved shape causes the distal portion of delivery tool 152 to disengage from the ocular implant. When the delivery tool disengages from the ocular implant, the connection between these two elements is broken. When the connection is broken, the ocular implant is released from the delivery system. Releasing the ocular implant from the delivery system in this manner causes the inlet portion of the ocular implant to be consistently placed in the correct position with respect to Schlemm's canal. Placing the inlet of the ocular implant in the correct location using this delivery system eliminates any need to adjust the position of the ocular implant after deployment. This delivery system is particularly beneficial when the physician's view of the ocular implant is obstructed at the time of release. The physician's view may be obstructed, for example, by blood reflux.

FIG. 38A is a plan view showing a delivery system housing 102 held in a left hand LH. FIG. 38B is a plan view showing delivery system housing 102 held in a right hand RH. In the embodiment of FIG. 38A, cannula 108 is disposed in a left handed position. In the embodiment of FIG. 38B, cannula 108 is disposed in a right handed position. The right handed position and the left handed position are rotated about one hundred and eighty degrees from each other causing trough portion 189 of distal opening 132 of cannula 108 to be visible in both FIG. 38A and FIG. 38B.

As shown in FIGS. 38A-38B, the body of cannula 108 extends along a longitudinal center axis 196. Longitudinal center axis 196 includes a curved portion so that longitudinal center axis 196 defines a curvature plane 148. In some embodiments, trough portion 189 of distal opening 132 is symmetrical about curvature plane 148. A tapered distal tip of cannula 108 is also symmetrical about the curvature plane 148. The symmetrical design of cannula 108 allows both left handed users and right handed users to use the cannula in substantially the same way.

While exemplary embodiments of the present invention have been shown and described, modifications may be made, and it is therefore intended in the appended claims to cover all such changes and modifications which fall within the true spirit and scope of the invention.

What is claimed is:

1. A method of delivering an ocular implant into Schlemm's canal of an eye, the method comprising:
    inserting a distal portion of a cannula into an anterior chamber of the eye, the cannula distal portion comprising an opening a beveled edge portion, and a curved trough extending from a proximal extent of the beveled edge portion;
    inserting the beveled edge portion into Schlemm's canal;
    advancing the ocular implant distally through the cannula into the trough and into Schlemm's canal, wherein the ocular implant is advanced using a delivery tool having a first interlocking portion engaged with a complementary second interlocking portion of a proximal end of the ocular implant;
    ceasing advancement of the ocular implant through the cannula when the proximal end of the ocular implant is disposed in the trough;
    disengaging the delivery tool from the ocular implant when the proximal end of the ocular implant is positioned in the trough; and
    removing the cannula while leaving at least a distal portion of the ocular implant in Schlemm's canal.

2. The method of claim 1, wherein the delivery tool has a curved at-rest shape, the disengaging step comprising permitting the delivery tool to assume its at-rest shape when the first interlocking portion is disposed in the trough.

3. The method of claim 1, wherein the beveled edge portion extends from the distal end of the cannula to two apexes at the distal end of the trough.

* * * * *